United States Patent
Eggers et al.

[19]

[11] Patent Number: 5,928,155
[45] Date of Patent: Jul. 27, 1999

[54] CARDIAC OUTPUT MEASUREMENT WITH METABOLIZABLE ANALYTE CONTAINING FLUID

[75] Inventors: Philip E. Eggers, Dublin, Ohio; Scott P. Huntley, Danville, Calif.; Gamal Eddin Khalil, Redmond, Wash.

[73] Assignee: Cardiox Corporation, Menlo Park, Calif.

[21] Appl. No.: 09/040,167

[22] Filed: Mar. 17, 1998

Related U.S. Application Data

[63] Continuation-in-part of application No. 08/792,967, Jan. 24, 1997, Pat. No. 5,788,647.

[51] Int. Cl.$^6$ .................................................... A61B 5/028
[52] U.S. Cl. ......................... 600/526; 600/341; 600/479
[58] Field of Search ..................................... 600/322, 341, 600/342, 368, 478, 479, 481, 508, 526, 486; 604/20

[56] References Cited

U.S. PATENT DOCUMENTS

| | | |
|---|---|---|
| 3,269,386 | 8/1966 | Sherman . |
| 3,304,413 | 2/1967 | Lehmann et al. . |
| 3,359,974 | 12/1967 | Khalil . |

(List continued on next page.)

FOREIGN PATENT DOCUMENTS

| | | |
|---|---|---|
| 235811 | 9/1987 | European Pat. Off. . |
| WO 8806426 | of 1988 | WIPO . |

OTHER PUBLICATIONS

"A New Technique for Measurement of Cardiac Output by Thermodilution in Man" Ganz, M.D., et al.
"Intravascular and Intracardiac Blood Temperatures in Man" Afonso, et al.
"Instantaneous and Continuous Cardiac Output Obtained With a Doppler Pulmonary Artery Catheter" Segal, et al.
"Transtracheal Doppler: A New Procedure for Continous Cardiac Output Measurement" Abrams, et al.
"Continuous Cardiac Output Monitoring During Cardiac Surgery" Schreuder, et al.
"Alternatives to Swan–Ganz Cardiac Output Monitoring" Morre, M.D., et al.
"Continuous Measurement of Blood Oxygen Saturation In the High Risk Patient" Schweiss, M.D., 1983.
"Electrochemical Performance, Biocompatibility, and Adhesion of New Polymer Matrices for Solid–State Ion Sensors" Cha, et al., Analytical Chemistry, pp. 1666–1672, 1991.
"Exercise–Induced Hyperammonemia: Peripheral and Central Effects" Banister, et al., International Journal of Sports Medicine, pp. S129–S142, 1990.

(List continued on next page.)

*Primary Examiner*—Cary O'Connor
*Assistant Examiner*—Eric F. Winakur
*Attorney, Agent, or Firm*—Mueller and Smith, LPA

[57] ABSTRACT

Cardiac output is measured utilizing a catheter in conjunction with the indicator dilution technique. Non-thermal analyte-containing fluid is used as the injectate. This fluid is biocompatible with and metabolizable within the body of the patient. An analyte concentration sensor is mounted upon the catheter and located downstream within the bloodstream from the port from which the analyte-containing fluid is expressed. Because of the matching of rapid concentration sensor response with an analyte-containing fluid which is metabolizable, the measurement of cardiac output may be carried out as often as about one to three minutes in conjunction with an infusion interval substantially less than the measurement frequency interval. The analyte-containing fluids are selected from a group consisting of ammoniacal fluid, heparin, ethanol, a carbon dioxide releasing fluid, glucose, and anesthesia agent. The system performs in conjunction with a microprocessor-driven controller which automates the measurement procedure and provides a display of cardiac output and various cardiovascular parameters.

62 Claims, 25 Drawing Sheets

U.S. PATENT DOCUMENTS

| | | |
|---|---|---|
| 3,433,935 | 3/1969 | Sherman . |
| 3,618,591 | 11/1971 | Bradley et al. . |
| 3,670,715 | 6/1972 | Perilhou et al. . |
| 3,678,922 | 7/1972 | Philips et al. . |
| 3,820,530 | 6/1974 | Gilford et al. . |
| 4,015,593 | 4/1977 | Klings et al. . |
| 4,217,910 | 8/1980 | Khalil . |
| 4,236,527 | 12/1980 | Newbower et al. . |
| 4,240,441 | 12/1980 | Khalil . |
| 4,316,391 | 2/1982 | Tickner . |
| 4,507,974 | 4/1985 | Yelderman . |
| 4,572,206 | 2/1986 | Geddes et al. . |
| 4,595,015 | 6/1986 | Jansen et al. . |
| 4,597,848 | 7/1986 | Oka et al. . |
| 4,671,295 | 6/1987 | Abrams et al. . |
| 4,685,470 | 8/1987 | Sekii et al. . |
| 4,722,347 | 2/1988 | Abrams et al. . |
| 4,733,669 | 3/1988 | Segal . |
| 4,785,823 | 11/1988 | Eggers et al. . |
| 4,791,935 | 12/1988 | Baudino et al. . |
| 4,807,629 | 2/1989 | Baudino et al. . |
| 4,819,655 | 4/1989 | Webler . |
| 4,841,981 | 6/1989 | Tanabe et al. . |
| 4,869,263 | 9/1989 | Segal et al. . |
| 4,949,724 | 8/1990 | Mahutte et al. . |
| 5,046,505 | 9/1991 | Sekii et al. . |
| 5,088,491 | 2/1992 | Schaldach . |
| 5,092,339 | 3/1992 | Geddes et al. . |
| 5,383,468 | 1/1995 | Nakayama et al. . |
| 5,395,505 | 3/1995 | Band et al. . |
| 5,413,592 | 5/1995 | Schroeppel . |
| 5,435,308 | 7/1995 | Gallup et al. . |
| 5,443,074 | 8/1995 | Roelandt et al. . |
| 5,458,128 | 10/1995 | Polanyi et al. . |
| 5,464,434 | 11/1995 | Alt . |
| 5,611,338 | 3/1997 | Gallup et al. . |
| 5,647,359 | 7/1997 | Kohno et al. . |

OTHER PUBLICATIONS

"When and How should We measure Plama Ammonia?" Green, Annals of Clinical Biochemistry, pp. 199–209, 1988.

"A polypyrrole–based Amperometric Ammonia Sensor" Lahdesmaki, et al., Talanta, pp. 125–134, 1996.

"Intergrated–circuit–compatible design and technology of acoustic–wave–based microsensors", Vellekoop et al., Sensors and Actuators A, pp. 249–263, 1994.

"Interaction of Planar polymer Schottky barrier diodes with gaseous substances", Assadi et al., Sensors and Actuators B, pp. 71–77, 1994.

"Electrode Systems For Continuous Monitoring in Cardiovascular Surgery" Clerk, et al.

"A Novel Electrochemical Heparin Sensor" Yang, et al., ASAIO Journal, pp. M195–M201, 1993.

"A Distribution of Ammonia Between Extracellular and intracellular Compartment of the Rat Brain" Hindfelt, Clinical Science and Molecular Medicine, pp. 33–37, 1975.

"The Dynamics of Ammonia Metabolism in Man" Lockwood, et al., Journal of Clinical Investigation, pp. 449–460, 1979.

"Nitrogen Balance after Intravenous and Oral Administration of Ammonium Salts to Man" Furst, et al., Journal of Applied Physiology, pp. 13–22, 1969.

"Ferrocene–Medicated Enzyme Electrode for Amperometric Determination of Gluscose" Cass, et al., Analytical Chemistry, pp. 667–671, 1984.

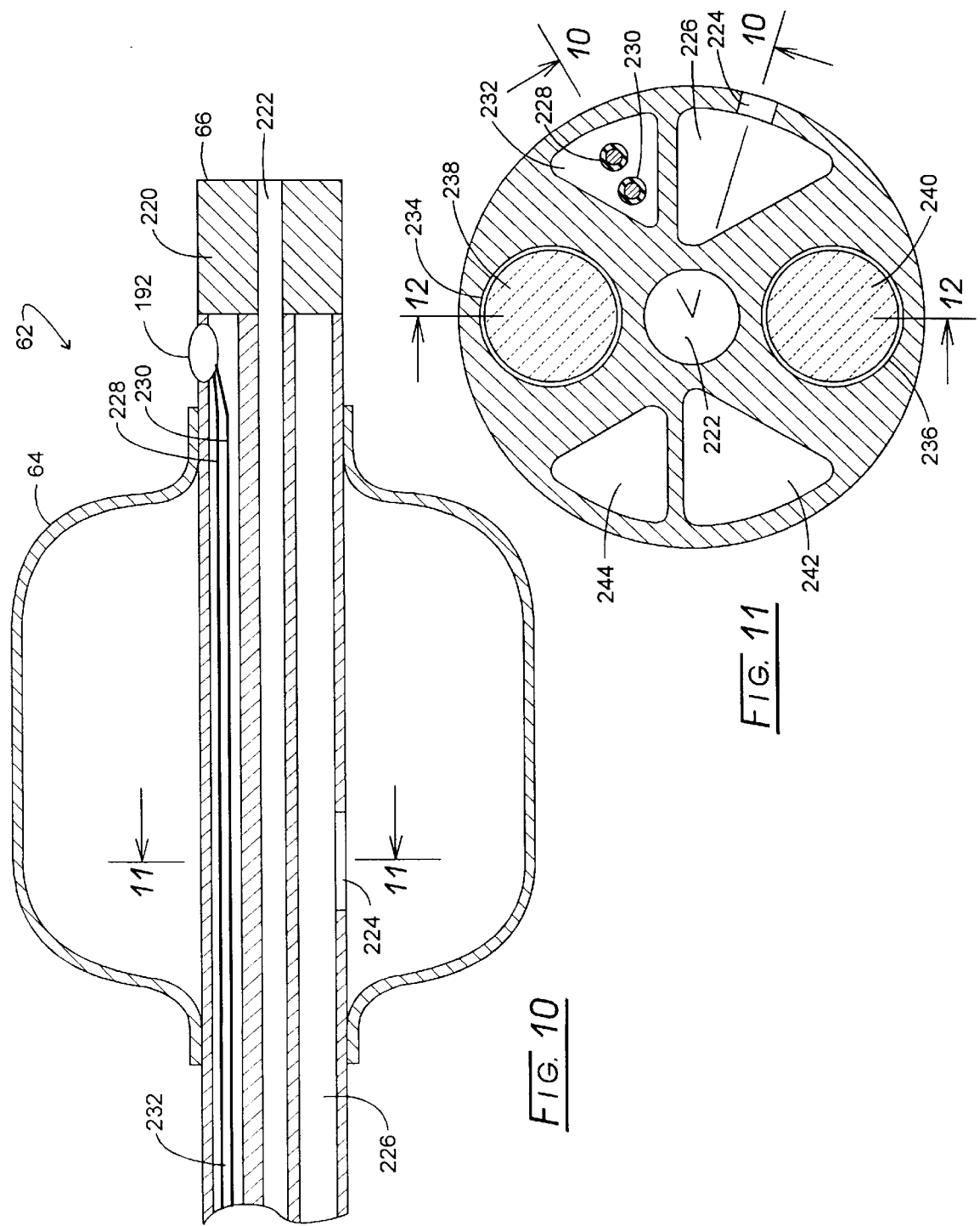

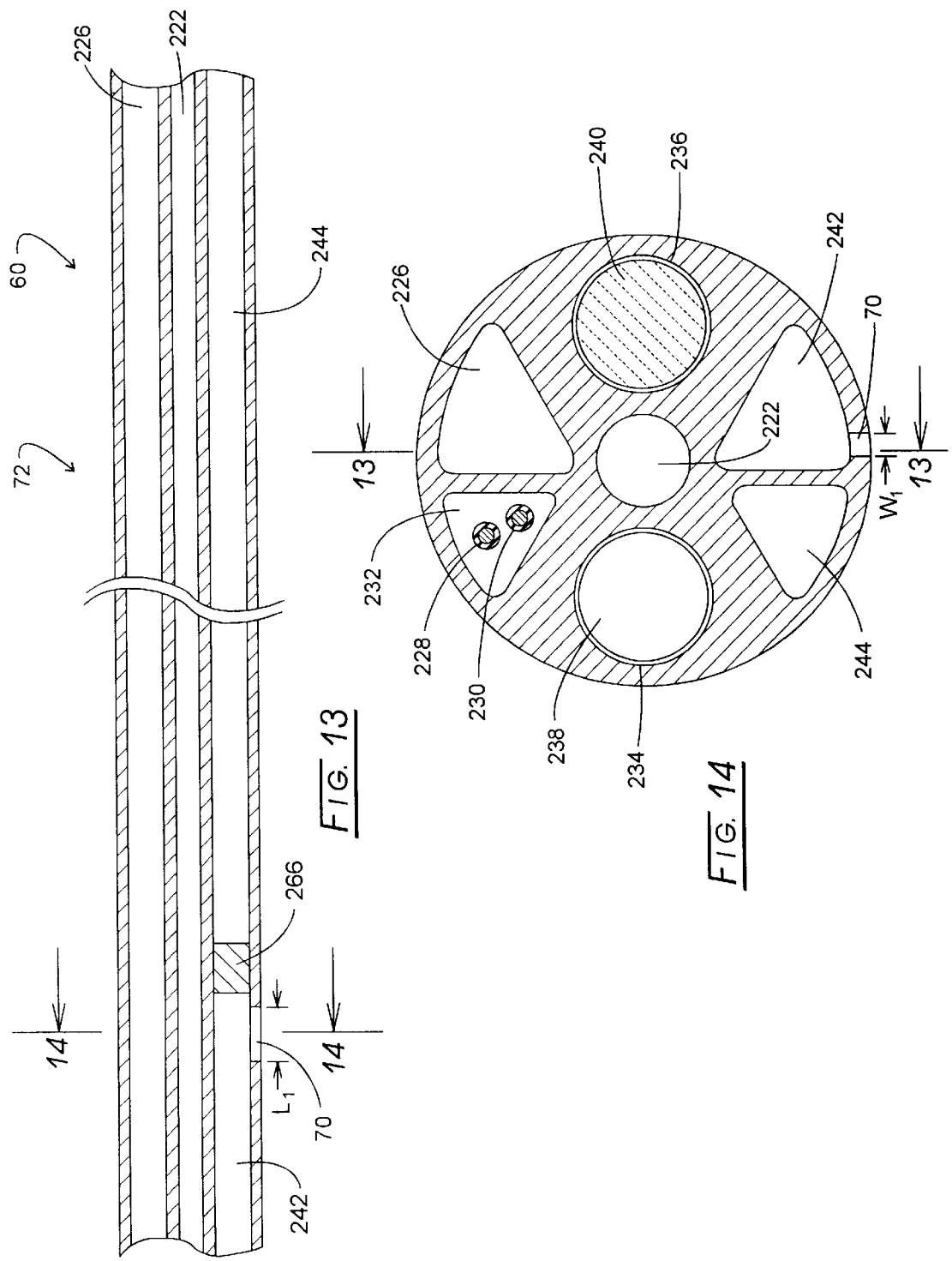

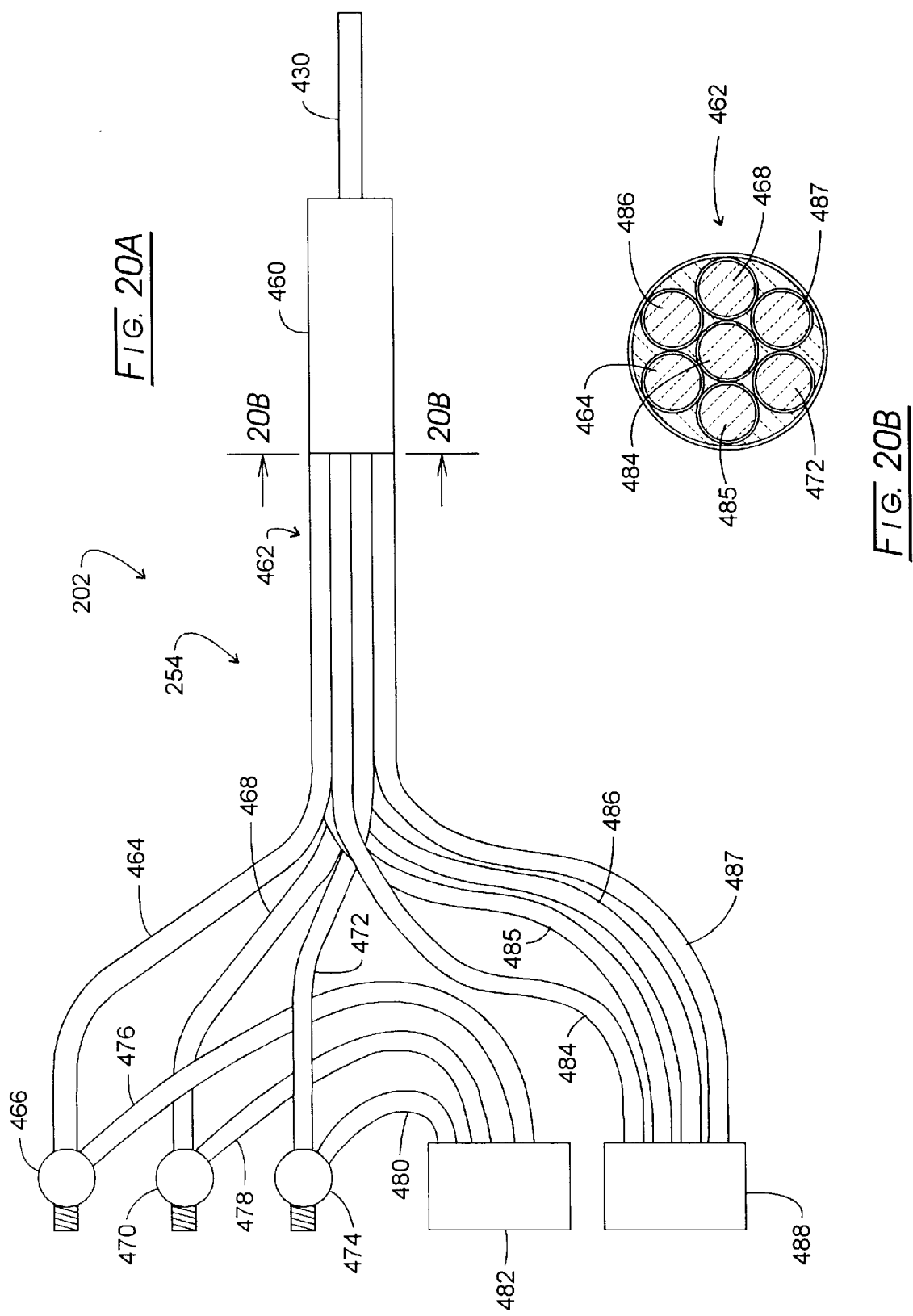

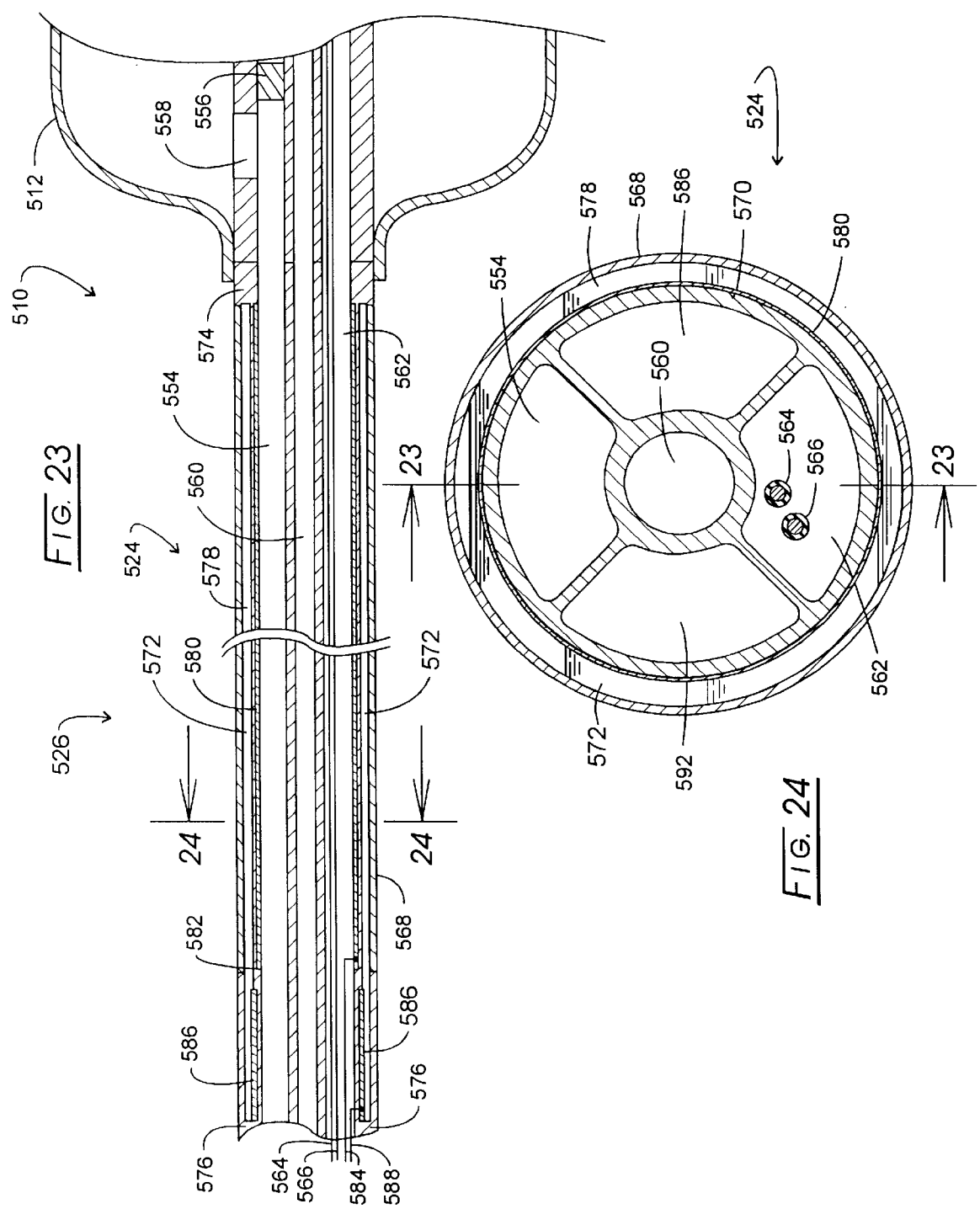

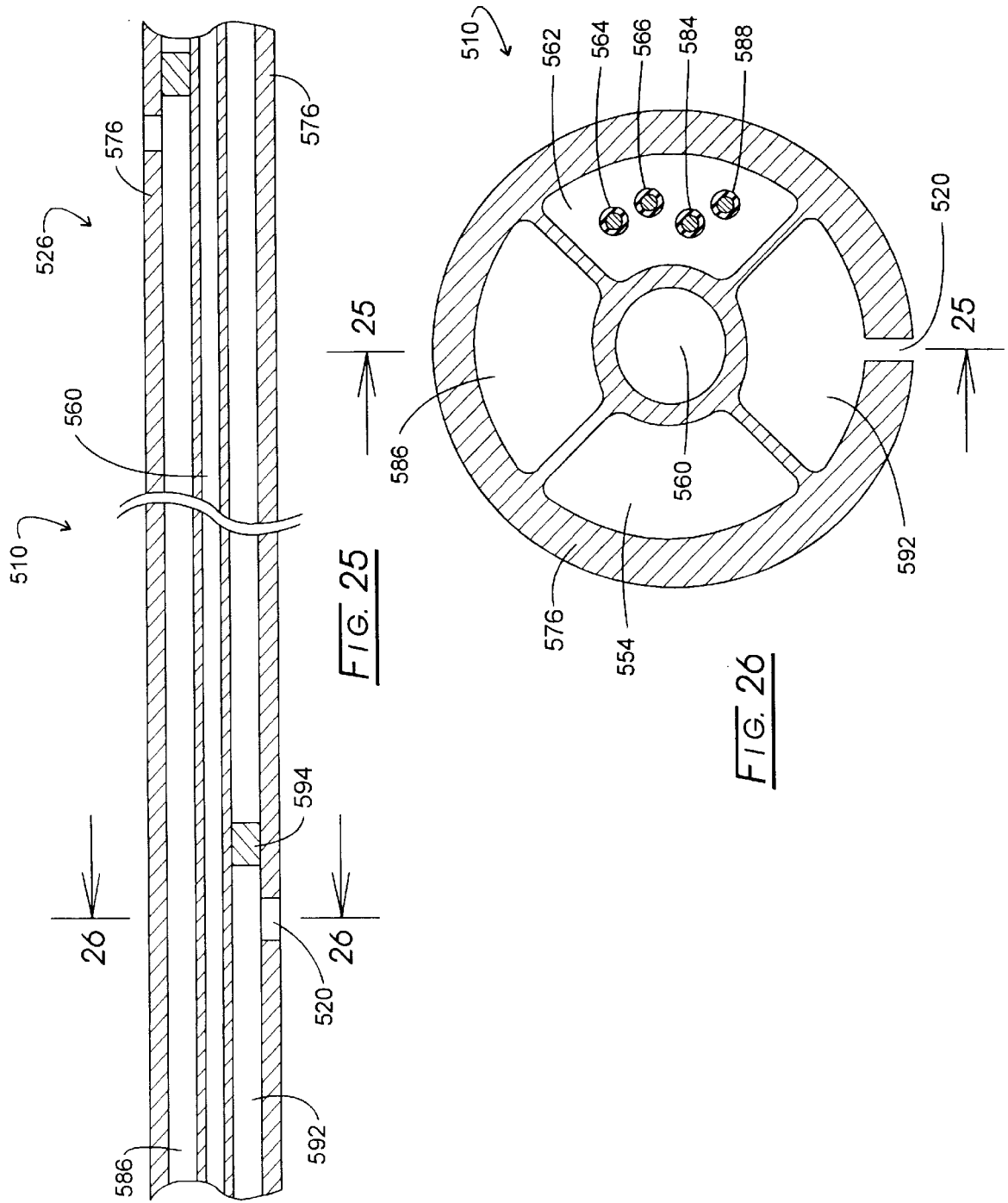

CARDIAC OUTPUT MEASUREMENT WITH METABOLIZABLE ANALYTE CONTAINING FLUID

CROSS-REFERENCE TO RELATED APPLICATIONS

This application is a continuation-in-part of U.S. application Ser. No. 08/792,967 filed Jan. 24, 1997 now U.S. Pat. No. 5,788,647.

STATEMENT REGARDING FEDERALLY SPONSORED RESEARCH

Not applicable.

BACKGROUND OF THE INVENTION

The determination of cardiac output, or measurement of the blood volumetric output of the heart is of substantial importance for a variety of medical situations. Intensivists utilize such information along with a number of additional pulmonary factors to evaluate heart patients within intensive care units. A variety of approaches have been developed for measuring this output, all of which exhibit certain limitations and/or inaccuracies. In effect, the volumetric aspect of cardiac output provides information as to the sufficiency of oxygen delivery to the tissue or the oxygenation of such tissue. When combined with other measurements, an important evaluation of the status of the cardiovascular system of a patient may be achieved.

Currently, the more accepted approach for deriving cardiac output values is an indicator dilution technique which takes advantage of refinements made earlier in pulmonary catheter technology. With the indicator dilution approach, a signal is inserted into the blood upstream from the pulmonary artery, and the extent of signal dilution can then be correlated with stroke volume or volumetric output of the heart. Of these indicator dilution methods, thermodilution is the present technique of choice, and in particular, that technique employing a cold liquid injectate as the signal. This approach is invasive, requiring placement of a Swan-Ganz pulmonary artery catheter such that its tip or distal end functions to position a temperature sensor just beyond the right ventricle within the pulmonary artery. The indicator employed is a bolus of cold isotonic saline which is injected from the indwelling catheter into or near the right atrium. Downstream blood temperature then is monitored to obtain a dilution curve relating temperature deviation to time, such curves sometimes being referred to as "wash out" curves. Combining the area under this thermodilution curve with the amount of energy subtracted by cooling of the blood provides a measure of the rate at which the heart is pumping blood, such rate usually being expressed in liters per minute. If cardiac output is high, the area under the thermodilution curve for a given applied energy, Q, will be relatively small in accordance with the well-known Stewart-Hamilton relationship. Conversely, if cardiac output is low, the area under the thermodilution curve for a given amount of applied energy, Q, will be relatively large. See in this regard:

Ganz, et al., "A New Technique for the Measurement of Cardiac Output by Thermodilution in Man," American Journal of Cardiology, Vol. 27, April, 1971, pp 392–396.

In a typical procedure, a cold bolus of saline at ice or room temperature in an amount of about 5–10 milliliters is injected through the catheter as a measurement procedure which will require about two minutes to complete. For purposes of gaining accuracy, this procedure is repeated three or four times and readings are averaged. Consequently, the procedure requires an elapsed time of 4–5 minutes. In general, the first measurement undertaken is discarded inasmuch as the catheter will have resided in the bloodstream of the body at a temperature of about 37° C. Accordingly, the first measurement procedure typically is employed for the purpose of cooling the dilution channel of the catheter, and the remaining measurements then are averaged to obtain a single cardiac output value. Thus, up to about 40 ml of fluid is injected into the pulmonary system of the patient with each measurement which is undertaken. As a consequence, this procedure is carried out typically only one to two times per hour over a period of 24 to 72 hours. While practitioners would prefer that the information be developed with much greater frequency, the procedure, while considered to be quite accurate, will add too much fluid to the cardiovascular system if carried out too often. Of course, the accuracy of the procedure is dependent upon an accurate knowledge of the temperature, volume, and rate of injection of the liquid bolus. Liquid volume measurements during manual infusions are difficult to make with substantial accuracy. For example, a syringe may be used for injecting through the catheter with the result that the volume may be identified only within several percent of its actual volume. Operator error associated with volume measurement and rate of injection also may be a problem. Because the pulmonary catheters employed are somewhat lengthy (approximately 30 to 40 inches), it is difficult to know precisely the temperature of the liquid injectate at the point at which it enters the bloodstream near the distal end of that catheter. Heat exchange of the liquid dispensing device such as a syringe with the catheter, and the blood and tissue surrounding the catheter upstream of the point at which the liquid is actually released into the blood may mean that the injectate temperature is known only to within about five percent of its actual temperature. Notwithstanding the slowness of measurement and labor intensity of the cold bolus technique, it is often referred to as the "gold standard" for cardiac output measurement by practitioners. In this regard, other techniques of determining cardiac output typically are evaluated by comparison with the cold bolus approach in order to determine their acceptability.

Another technique of thermodilution to measure cardiac output employs a pulse of temperature elevation as the indicator signal. In general, a heating coil is mounted upon the indwelling catheter so as to be located near the entrance of the heart. That coil is heated for an interval of about three seconds which, in turn, functions to heat the blood passing adjacent to it. As is apparent, the amount of heat which can be generated from a heater element is limited to avoid a thermocoagulation of the blood or damage to tissue in adjacency with the heater. This limits the extent of the signal which will be developed in the presence of what may be considered thermal noise within the human body. In this regard, measurement error will be a result of such noise phenomena because of the physiological blood temperature variation present in the body. Such variations are caused by respirations, coughing, and the effects of certain of the organs of the body itself. See in this regard:

Afonzo, S., et al., "Intravascular and Intracardiac Blood Temperatures in Man," *Journal of Applied Physiology*, Vol. 17, pp 706–708, 1962. See also, U.S. Pat. No. 4,595,015.

This thermal noise-based difficulty is not encountered in the cold bolus technique described above, inasmuch as the caloric content of a cold bolus measurement is on the order of about 300 calories. By contrast, because of the limitations on the amount of heat which is generated for the temperature approach, only 15 or 20 calories are available for the measurement. Investigators have attempted to correct for the thermal noise problem through the utilization of filtering techniques, for example, utilizing moving averages over 6 to 12 readings. However, where such corrective filtering approaches are utilized, a sudden downturn in the hemodynamic system of a patient will not be observed by the practitioner until it may be too late. The effective measurement frequency or interval for this technique is somewhat extended, for example about 10 minutes, because of the inaccuracies encountered. In this regard, a cardiac output value is achieved only as a consequence of a sequence of numerous measurements. In general, the approach does not achieve the accuracy of the above-discussed cold bolus technique. Thermodilution techniques involving the use of electrical resistance heaters are described, for example, in U.S. Pat. Nos. 3,359,974; 4,217,910; 4,240,441; and 5,435,308.

Other approaches to the elimination of an injectant in thermodilution procedures have been, for example, to introduce the thermal signal into the flowing blood by circulating a liquid within the catheter, such liquid preferably being cooler than the blood temperature. See in this regard, U.S. Pat. No. 4,819,655. While, advantageously, no injectant is utilized with such procedure, the method has the disadvantage that only a limited thermal signal is available as compared with the cold bolus approach, and, thus, the measurement is susceptible to error due to physiological temperature variations. As another example, a technique has been proposed wherein a stochastic excitation signal present as a series of thermal pulses of varying duration is asserted within the bloodstream, and the resultant output signal downstream, now present as blood temperature variation, is measured. The blood flow rate then is extracted by cross-correlating the excitation signal and measured output signal. See U.S. Pat. No. 4,507,974.

Dilution and conductivity dilution techniques, also involving injection of an auxiliary liquid such as a dye or saline solution into the bloodstream are known. See in this regard, U.S. Pat. Nos. 3,269,386; 3,304,413; 3,433,935; 3,820,530; 4,572,206; and 5,092,339. A resulting dilution or conductivity dilution curve will be seen to be similar to the above-discussed thermodilution curve. Dilution and conductivity dilution procedures exhibit certain of the deficiencies discussed in connection with the injected liquid bolus-based thermodilution approach, namely difficulty in precisely controlling the rate of manual injection and measuring the injectate volume as well as an unsuitability of the procedure for frequent or repeated use over long periods of time. The above-noted dye dilution procedures have been employed for a relatively extensive period of time. In general, a dye is injected into the bloodstream and then a blood sample is drawn, typically from a major artery, at various intervals of time. The technique is quite labor intensive and, because of the extensive amount of dye which is required to obtain an accurate measurement. The frequency of measurement is very low. In particular, if the frequency is attempted to be enhanced, then the signal-to-noise ratio encountered becomes unacceptable as the background color of the blood continues to change. The saline solution approach involves the injection of a hypertonic saline solution having a much higher salt content per unit volume than, for example, typical isotonic saline solution which is about 0.9% sodium chloride. Following injection of the hypertonic saline solution, the electrical resistivity of the blood is evaluated. The method has been criticized inasmuch as such an extensive amount of electrolyte is added to the blood for each measurement, the electrolyte balance in the body becomes adversely affected. Note that the technique looks at electrical charges in a direct fashion as they exist in the bloodstream. Another indicator-dilution method for determining cardiac output involves the utilization of a cation, preferably lithium, which is not already present in the blood. This cation is injected as a bolus into the blood. A cation selective electrode is used to measure concentration and subsequently develop a resulting cation dilution curve in a manner similar to a thermodilution measurement. Cation-dilution cardiac output measurement methods share certain of the same deficiencies as discussed above for liquid-bolus-based thermodilution methods. See U.S. Pat. No. 5,395,505.

Ultrasonic echocardiography has been employed for the instant purpose. With this invasive method, a plurality of microbubbles is introduced into the blood upstream of the measurement position. As described in U.S. Pat. No. 4,316,391, an ultrasonic pulse is generated from a position opposite and spaced from the region of the flowing microbubbles, for example, using an ultrasonic transducer/receiver located outside of the body. A reflective ultrasonic image, created by reflection of the ultrasonic pulse from the microbubble dispersions is measured and correlated with cardiac output, i.e. flow rate, using conventional dilution techniques. This method preferably employs microbubbles comprising a gelatin membrane-encased "inert" gas such as nitrogen or carbon dioxide to perform each measurement. As a consequence, the method is not suitable for performing clinical measurements continuously or even intermittently for an extended period of time due to the accumulation of bubble membrane material that must be cleared from the body by the body's own cleansing processes.

A derivation of cardiac output by simultaneously measuring blood velocity and vessel geometry has been described, for example, in U.S. Pat. Nos. 4,733,669 and 4,869,263. With this approach, a Doppler pulmonary artery catheter system is provided which develops instantaneous vessel diameter measurements and a mapping of instantaneous blood velocity profiles within the main pulmonary artery. From such data, an instantaneous cardiac output then is calculated. See in this regard the following publication:

"Instantaneous and Continuous Cardiac Output Obtained with a Doppler Pulmonary Artery Catheter," *Journal of the American College of Cardiology*, Vol. 13, No. 6, May, 1989, pp 1382–1392.

A similar approach has been described which involves a technique wherein a piezoelectric ultrasound transducer is placed in the trachea of a patient in proximity to the aorta or pulmonary artery. Ultrasound waves then are transmitted toward the path of flow of blood in the artery and are reflected and received. The cross-sectional size if the artery is measured, based upon the Doppler frequency difference between the transmitted and received waves. Imaging techniques such as X-ray or radioisotopic methods also have been used. See generally the following publication:

"Transtracheal Doppler: A New Procedure for Continuous Cardiac Output Measurement," *Anesthesiology*, Vol. 70, No. 1, January 1989, pp 134–138.

See additionally, U.S. Pat. Nos. 4,671,295 and 4,722,347.

A pulse contour technique for measuring blood velocity which requires a secondary calibration is described in the following publication:

"Continuous Cardiac Output Monitoring During Cardiac Surgery," *Update in Intensive Care and Emergency Medicine*, Berlin: Springer-Verlag, 1990, pp 413–417.

Another approach employs a so-called "hot wire" anemometer or heated thermistor as described in U.S. Pat. No. 4,841,981; EP 235811; U.S. Pat. No. 4,685,470, and WO88/06426.

Any of the velocity-based measurement techniques for deriving cardiac output confront a rather basic difficulty not present with indicator dilution approaches. That difficulty resides in the necessity for knowing the geometric cross section of the vessel through which blood is flowing. In this regard, the geometry and diametric extent of the pulmonary artery is not known and is dynamic, changing with the pulsation nature of blood flow. Of course, the velocity measurements themselves must account for the surface effect of the interior of the vessel, velocity varying from essentially a zero value at the interior surface or lumen of the vessel to a maximum value towards the interior of that vessel.

A non-invasive technique evaluating thorasic electrical bioimpedance to derive cardiac outputs has been studied, for example, using electrocardiographic signals (ECG). However, cross-correlation of the results with the well-accepted thermodilution technique have led to questions of reliability.

For a general discourse looking to alternatives to the current indicator dilution method of choice, reference is made to the following publication:

"Alternatives to Swan-Ganz Cardiac Output Monitoring" by Moore, et al., *Surgical Clinics of North America*, Vol. 71, No. 4, August 1991, pp 699–721.

What is called for in this hemodynamic field of endeavor is an approach to cardiac output measurement which permits the generation of a cardiac output value of accuracy at least commensurate with the cold bolus technique at a measurement frequency much higher than currently available, for example, at intervals of 1 to 3 minutes. The technique employed must not be labor intensive in view of the current cost constraints encountered by clinicians. Of corresponding importance, the technique cannot adversely alter the body stability of the patient, i.e., the blood component should not be adversely diluted or changed to the extent that the treatment evokes iatrogenesis.

BRIEF SUMMARY OF THE INVENTION

The present invention is addressed to apparatus, system, and method for determining the cardiac output (CO) of the cardiovascular system of the body of a patient. Utilizing a catheter-based indicator dilution approach, the system is capable of carrying out cardiac output measurements with a highly enhanced measurement rapidity, without adverse consequences to body hemostasis or stability. Enhanced CO measurement rates are achieved by the selection of an analyte containing fluid as the dilution injectate which is non-thermal, biocompatible, and importantly, metabolizable within the body of the patient. Such analyte selection is combined in the system with selection of an analyte concentration sensor which is catheter-mounted, having a rapidly evaluatable output response exhibiting substantial accuracy. That accuracy is achieved without call for a multiple measurement averaging regimen heretofore required, for example, in thermal dilution CO measurement techniques.

Implemented with a microprocessor-driven bedside controller, the approach of the invention avoids labor intensive CO measurement procedures, while making a variety of cardiovascular parameters available at a display and inconjunction with recorded media. The controller also monitors the concentration of analyte-containing fluid in the bloodstream to ascertain that concentration level which corresponds with hemostasis. That concentration level is one wherein there is an equilibriation of the analyte fluid concentration with the corresponding metabolic activity of the body. As cardiac output measurements continue under this stable equilibriated physiological state of the body, no discernable rise in blood indicator concentration in blood is evidenced. In practice, the intensivist inputs a homeostasis threshold value corresponding with an analyte-containing fluid concentration in blood for iatrogenesis. The controller then monitors the background concentration of analyte-containing fluid in the bloodstream which corresponds with hemostasis with respect to the threshold value and provides a perceptible output which may include an alarm in the event such threshold is exceeded.

The analyte concentration sensor mounted with a catheter and the analyte-containing fluid are selected having a capability for providing a concentration sensor output with rapidity effective to derive a cardiac output measurement as often as about 1 to 3 minutes in conjunction with an infusion interval wherein the analyte-containing fluid is injected into the bloodstream which is substantially less than the measurement frequency interval. In this regard, the infusion interval is elected as about 2 to 30 seconds. Analyte-containing fluids which may be employed with this approach are selected from the group consisting of ammoniacal fluid, heparin, ethanol, a carbon dioxide releasing fluid, glucose, and anesthesia agent. Of the above, ammoniacal fluids are preferred in combination with an analyte concentration sensor which senses ammonia gas ($NH_3$) through a fiberoptic assembly performing in conjunction with a membrane-covered reactor which is present as an ammonia sensitive dye. The membrane employed as one impervious to blood but pervious to ammonia ($NH_3$). A particular advantage in employing an ammoniacal fluid is the analyte-containing fluid resides in its mixture with both the hemoglobin and plasma components of blood. As a consequence, no accommodation is required in the controller analysis for corrections with respect to the latter parameter (viz, the blood hematocrit level).

As another aspect of the invention, a method is provided for determining the cardiac output of the cardiovascular system of the body of the patient comprising the steps of:

(a) providing a catheter having a proximal end region extending to a measurement region, an indicator channel within the catheter having a fluid input at the proximal end region and extending to an infusion outlet at the measurement region from which analyte-containing fluid may be expressed, an analyte concentration sensor mounted with the catheter having a forward assembly contactable with flowing blood at the measurement region at a location spaced from the infusion outlet a dilution measurement distance, the sensor being responsive to the concentration of an analyte to provide an output corresponding with the concentration of analyte in blood, and having a capability for providing the output within an infusion interval achieving a cardiac output measurement frequency interval of about one to three minutes;

(b) positioning the catheter within the bloodstream of the body locating the measurement region at the heart region of the patient in a cardiac output orientation wherein the analyte concentration sensor is downstream within the bloodstream from the infusion outlet;

(c) providing a source of analyte-containing fluid biocompatible with and metabolizable within the body such analyte being independent of the thermal energy content of the fluid and having a predetermined indicator concentration;

(d) deriving a baseline value corresponding with the concentration of analyte in the bloodstream from the concentration sensor output;

(e) delivering the analyte-containing fluid from the source into the indicator channel input at a predetermined mass flow rate for an infusion interval;

(f) deriving a subsequent value corresponding with the concentration of analyte in the bloodstream from the concentration sensor output during the infusion interval; and (g) deriving the value for the cardiac output of the heart of the body by correlating the baseline value, the subsequent value, the predetermined indicator concentration, and the predetermined mass flow rate.

Other objects of the invention will, in part, be obvious and will, in part, appear hereinafter. The invention, accordingly, comprises the method, system, and apparatus possessing the construction, combination of elements, arrangement of parts, and steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 10 is a partial sectional and developed view taken along the wedge-shaped plane 10—10 in FIG. 11;

FIG. 11 is a sectional view taken through the plane 11—11 in FIG. 10;

FIG. 13 is a sectional view taken through the plane 13—13 in FIG. 14;

FIG. 14 is a sectional view taken through the plane 14—14 in FIG. 13;

FIG. 20A is a schematic representation of the optical components within a module employed with the front end assembly of FIG. 18;

FIG. 20B is a schematic sectional view taken through the plane 20B—20B shown in FIG. 20A;

FIG. 23 is a partial sectional view taken through the plane 24—24 shown in FIG. 23;

FIG. 24 is a sectional view taken through the plane 24—24 in FIG. 23;

FIG. 25 is a partial sectional view taken through the plane 25—25 in FIG. 26;

FIG. 26 is a sectional view taken through the plane 26—26 in FIG. 25;

DETAILED DESCRIPTION OF THE INVENTION

Figure 1:
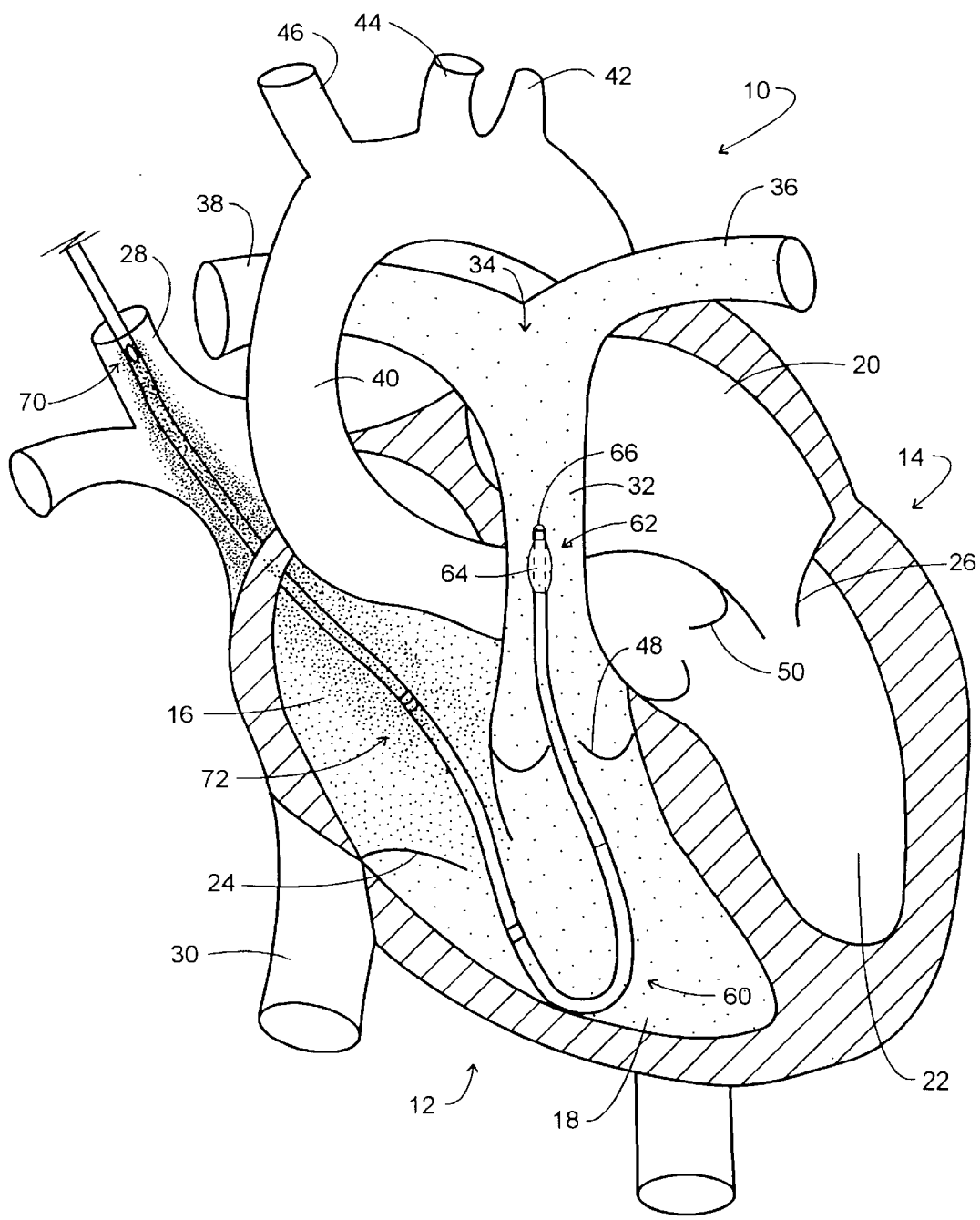
FIG. 1 is a schematic, partially sectional view of a heart showing the placement and illustrating the use of a cardiac output measuring catheter according to the invention.

Measurement of cardiac output has been the subject of substantial study and clinical practice since the 1970's. The approach now presented utilizes the technologies evolved from such studies and established sensing technology. In general, a dilution technique is performed utilizing catheters which are located in adjacency to and within the heart. The injectate employed with the dilution approach is an analyte-containing fluid which, of importance, is both biocompatible with and metabolizable within the body of the patient. The term "analyte" as employed herein is considered to be such a metabolizable substance which is undergoing analysis. The analyte-containing fluid may be essentially all analyte or a combination of a species of analyte or specific analyte with other components which are metabolized. The total concentration of the analyte within the source of analyte-containing fluid utilized, i.e. before injection, is referred to as the "indicator concentration". As the analyte-containing fluid is injected for an infusion interval of from about 2 to 30 seconds, sensing of the concentration in blood of the analyte or a component of the analyte commences to be undertaken. With frequent measurement intervals, for example between 1 and 3 minutes, the indicator concentration builds within the body. However, somewhat simultaneously, the body metabolizes the injectate and after an extended sequence of measurements, will reach a state of metabolic homeostasis or equilibrium wherein the indicator concentration remains constant and below a hemostasis threshold value corresponding with analyte-containing fluid indicator concentration for iatrogenesis. The latter is a level which would adversely affect the patient. An important complement to the success of the approach resides in the selection of an analyte concentration sensor which will respond to generate a concentration sensor output within the short infusion interval. In addition to being biocompatible with and metabolizable within the body of the patient, the analyte-containing fluids of the invention are non-thermal. In this regard, the analyte-containing fluid is not used with respect to its thermal characteristics. The analyte is independent of the thermal energy content of the analyte-containing fluid. The fluids are selected from the group consisting of ammoniacal fluid, heparin, ethanol, a carbon dioxide releasing fluid, glucose, and anesthesia agents. A variety of analyte concentration sensors employable within the system are described. Because of the complementing analyte and analyte concentration sensor approach utilized in conjunction with the metabolic process of the body, the system may be automated to perform under controller-based technology.

A preferred embodiment of the invention employs the well-established techniques associated with the placement of a pulmonary artery catheter, which is the delivery vehicle of choice with current thermodilution techniques. This preferred embodiment also employs the noted ammoniacal fluid as the analyte-containing fluid, for example, ammonium chloride. The indicator or analyte concentration of the analyte-containing fluid for this selection will be the combined content of ammonia gas and ammonium ion. In this regard, ammonia gas ($NH_3$) and ammonium ion ($NH_4^+$) are in the equilibrium ($NH_3 + H^+ \rightarrow NH_4^+$). The pKa of this reaction is 9.3, thus at physiological pH, the ammonium ion, $NH_4^+$ is mostly present. However, the preferred analyte component for concentration sensing in blood is ammonia gas ($NH_3$). A particular advantage accruing with the use of an ammoniacal fluid as the analyte-containing fluid or injectate of the procedure is a discovery made during animal experimentation that, when utilizing this analyte-containing fluid, the cardiac output method does not depend upon an evaluation of hematocrit (HCT). In this regard, the components of the analyte-containing fluid enter the red blood cells as well as plasma in a uniform way such that by sensing the amount of ammonia ($NH_3$), the system will obtain a dilution-based measurement output which is independent of the hematocrit component of the blood.

Looking to FIG. 1, a schematic representation of a human heart is identified generally at 10. In general, the heart 10 performs in two stages or sides, having a right side which receives venous-based blood returning from various tissues and vessels of the body. This right side of the heart is seen generally at 12 and functions to pump the oxygen depleted blood arriving from the venous system to the lungs to be oxygenated. Upon being oxygenated and cleared of excess carbon dioxide, the blood is returned from the lungs and pumped arterially against the vascular resistance of the entire body by the left side of the heart which is represented at 14. The pumping chambers of the heart are represented in FIG. 1 as a right atrium 16 and a right ventricle 18. Correspondingly, the left atrium is shown at 20 and the left ventricle at 22. The right atrioventricular valve is schematically portrayed at 24, correspondingly, the left atrioventricular (mitral) valve is represented at 26. Looking to input to the right side 12 of the heart 10, the superior vena cava is represented at 28, while the inferior vena cava is represented at 30. The output of the right ventricle is shown extending to the pulmonary artery 32 which, in turn, extends to a bifurcation represented generally at 34 to define a left pulmonary artery 36 and a right pulmonary artery 38. Left ventricle 22 is seen extending to the aorta 40 having an aortic arch from which the left subclavian artery extends as shown at 42, the left common carotid artery extends as shown at 44, and the brachiocophalic trunk extends as shown at 46. The pulmonary valve is seen at 48, while the aortic valve is represented at 50. The inferior vena cava 30 as well as the superior vena cava 28 both lead into the right atrium 16. Generally, venous blood introduced from the inferior vena cava 30 originates from the lower part of the body, i.e. the lower limbs, chest, and abdominal cavity. Correspondingly, venous blood entering from the superior vena cava 28 is conveyed from the upper anatomy, i.e. arms, head, and brain. Another drainage of venous flow not introduced from these two major veins evolves from blood draining from the sinuses onto the venous structure within the heart. These also mix at the right atrium 16 and the superior vena cava 28 as well as the inferior vena cava 30. In effect, then all of the blood passes through the right ventricle to the pulmonary artery 32. By measuring within this region, accuracy of caridac output measurement is achieved.

A pulmonary artery (PA) catheter adapted to carry out the system and method of the invention is represented generally at 60 at the indwelling location normally encountered for heart monitoring including cardiac output (CO) measurement purposes. In particular, the catheter 60 is located at the heart 10 in a fashion similar to that of the conventional Swan-Ganz flow directed thermodilution catheter. See in this regard, Daily, E, "Techniques in Bedside Hemodynamic Monitoring," C.B. Mosby Co., 1985. Note that the distal end or tip and measurement region represented generally at 62 and configured with a variety of components including a partially inflated balloon 64 is positioned in the pulmonary artery 32 upstream from the bifurcation 34. At this location, the tip region 62 will be immersed in flowing, mixed venous blood, and from this measurement location, as noted above, all of the blood of the body eventually will flow as it returns to the lungs for oxygenation. Catheters as at 60 conventionally are multi-channeled and formed of a soft or compliant material so as not to unduly interfere with the valve activities of the right side 12 of heart 10. Typically, the devices as at 60 will have a diameter of about 7.5 French (0.09 inch) and a length of about 40 inches extending from an externally disposed proximal end (not shown) to measurement region 62. The devices are introduced into the body percutaneously, normally being entered from the subclavian vein and the jugular vein at the shoulder/neck region or alternatively from a femoral vein in the leg. Devices 60 are termed as "flow directed", movement into position being achieved as a consequence of blood flow by virtue of the partially inflated balloon 64. Correspondingly, the proper positioning of the tip and measurement region 62 is confirmed, for example, by the pulmonary blood pressure waveforms developed by utilization of an open-ended fluid filled channel or lumen extending through catheter 60. This channel is open at the outer tip 66 of the catheter 60. In this regard, insertion of the catheter 60 is stopped when a pressure monitor employed with the blood pressure channel of the catheter exhibits an appropriate pressure profile. When appropriately positioned, the distal end will be located within the pulmonary artery 38 as illustrated. That same tip and measurement region 62 may also contain, for example, a temperature sensor and, in a preferred embodiment, the forward assemblies of optical fiber components of ammonia and pH optical sensors, the outputs of which, respectively, provide signals representing the concentration of the ammonia component of the analyte, and the pH of the blood at that measurement location. Located upstream in the sense of blood flow, an analyte-containing fluid injectate or infusion port of catheter 60, shown generally at 70, serves to infuse or express a known amount of solution into adjacent blood flow at a controlled mass flow rate, which infusion into the bloodstream occurs in the region shown, i.e., at the entrance to and within the right atrium. The region of the catheter 60 extending from the vicinity of the port 70 and the tip thereof at 66 represents a measurement region represented generally at 72. Within this measurement region, the forward assembly of analyte concentration sensor located at the tip region 62 will be at a location spaced from the infusion port or outlet 70, a dilution measurement distance downstream within the bloodstream. In the figure, a density of "dots" is used to represent the relative mix concentration of the analyte in the flowing bloodstream as that analyte is drawn while mixing from the superior vena cava 28 into the right atrium 16, thence through the right atrial ventricular valve 24, and into the right ventricle 18. Then, it is seen as being progressively diluted in correspondence with flow rate of blood through the pulmonary valve 48 to pass the analyte concentration sensor at the tip region 62 as it extends into pulmonary artery 32. As is apparent, at the commencement of the injection of analyte-containing fluid from port 70, a sensor at tip region 62 will not "see" the analyte resulting from the expression of analyte-containing fluid from port 70. The time delay before sensing of the injected analyte commences depends upon the cardiac output of the heart 10 as well as a need with the system at hand for good mixing of such analyte with the flowing blood. The resultant time delay typically will be on the order of about 2 to 4 seconds.

Figure 2:
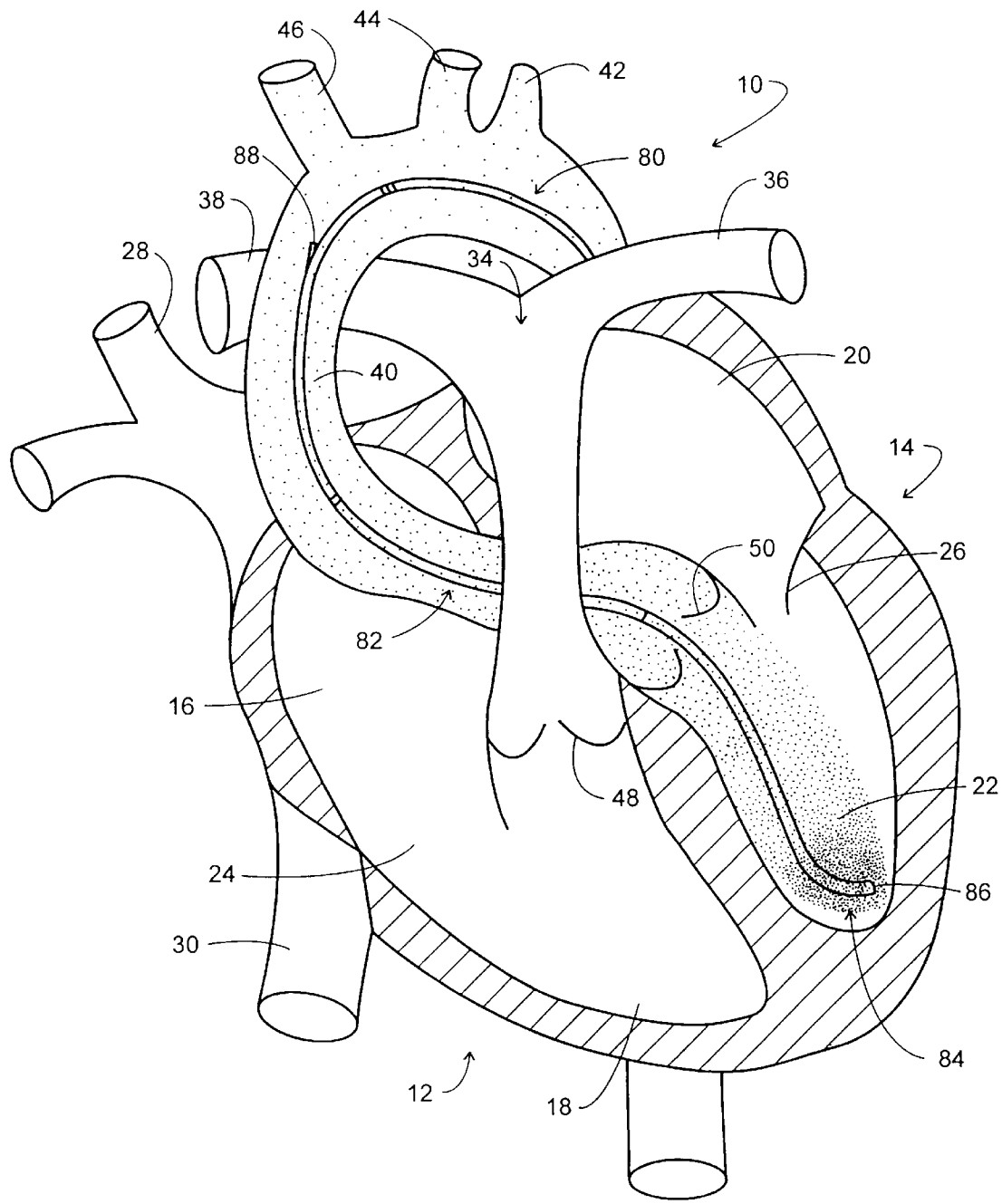
FIG. 2 is a schematic, partially sectional view of a heart showing the placement and illustrating the use of a cardiac output measuring catheter structured for arterial insertion.

While the preferred modality for utilizing the present system is with the right side of the heart, it can also be employed utilizing a catheter performing in conjunction with the left-side 14 of the heart 10. Referring to FIG. 2, the heart 10 is reproduced along with the associated components thereof employing the same identifying numeration as seen in FIG. 1. In the figure, a catheter represented generally at 80 is introduced through a major artery into the left half 14 of heart 10. The catheter 80 extends from an externally-disposed proximal end region (not shown) to an oppositely disposed measurement region represented generally at 82. The measurement region 82 extends from a distal or tip region represented generally at 84 inwardly from the tip 86. The tip 86, for this embodiment, is configured to provide an injectate or diffusion port or outlet from which analyte-containing fluid is expressed. The outlet or port at tip 86 is spaced a dilution measurement distance upstream from an analyte concentration sensor having a forward assembly contactable with flowing blood at 88. It may be noted that no partially inflated balloon as shown at 64 in FIG. 1 is employed in this modality. As before, however, a density of "dots" is used to represent the introduction and progressive mixing or dilution of the analyte in the flowing blood of the bloodstream, the diluted concentration of which is measured within the ascending aorta 40 with the sensor forward assembly 88.

Returning to FIG. 1, the general procedure for determining cardiac output (CO) involves, as a preliminary step, a baseline determination of the concentration of analyte-containing fluid in the blood. At the commencement of a procedure, the first baseline measurement will be of the analyte which is endogenous to the patient. Where the analyte component which is sensed is ammonia gas, the analyte concentration is represented by the total ammoniacal concentration in the blood, i.e. the combination of the concentration of ammonia gas ($NH_3$) and ammonium ion ($NH_4^+$). That baseline data or information having been obtained, then analyte-containing fluid biocompatible with and metabolizable within the body of the patient is injected into the bloodstream at a predetermined mass flow rate through ports as located at 70 in FIG. 1 or at the tip region 84 shown in FIG. 2 for an infusion interval. That interval will be determined by the rapidity of analyte sensing and the noted dilution of the distance from the injectate portal or outlet to the forward assembly of the sensor. During the infusion interval, a subsequent sensing of analyte or analyte component concentration level takes place which, as before, is converted to total analyte concentration level. By correlating the indicator concentration of the analyte-containing fluid source, the mass flow rate involved during the infusion interval, the baseline and subsequent analyte concentrations in blood and other factors which may be called for, cardiac output then is derived. For the preferred utilization of ammoniacal fluid as the analyte-containing fluid, the value of pH is utilized in the correlation. A particular advantage associated with the utilization of an ammoniacal fluid with the procedure is that no adjustment in analyte concentration values for hematocrit (HCT) content is required, the analyte being taken up both in the plasma and blood cell structure of the blood. Of additional importance to the procedure, only one measurement is required to achieve a value of cardiac output (CO), averaging of repetitive measurements not being required. The terms "mass flow rate" as used herein are meant to include any type of measured liquid, e.g. volumetric flow rate where temperature is known.

Figure 3:
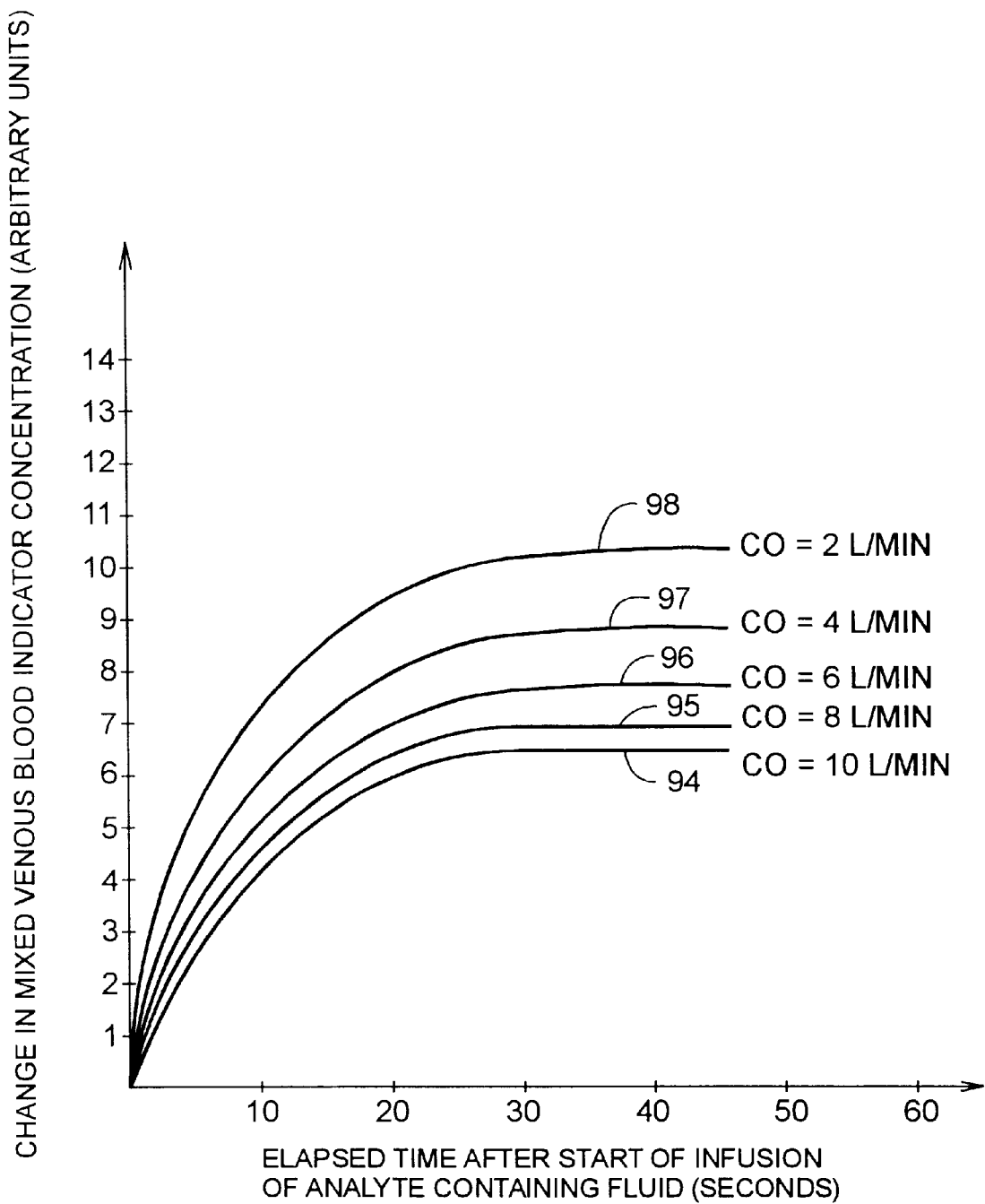
FIG. 3 illustrates a typical response relating blood indicator concentration with time from the start of an analyte-containing fluid infusion for five cardiac output values.

Looking to FIG. 3, curves 94 through 98 are plotted to reveal values for cardiac output (CO) with respect to elapsed time in seconds commencing with the injection of analyte containing fluid as further related to the observed change in the mixed venous blood indicator, i.e. analyte concentration in blood. Curves 94–98 correspond, respectively, with cardiac outputs of 10, 8, 6, 4, and 2 liters per minute. It may be observed from the figure that for a given injection rate, the lower the cardiac output rate, the larger the incremental increase in blood indicator concentration. This dependence of the incremental increase in analyte concentration in blood is due to the indicator-dilution effect in which the lower the blood flow rate (i.e., cardiac output), the less a given level of analyte-containing fluid injectate will be dispersed and diluted. In general, the measurement response time of an ammonia gas sensor employed with the preferred embodiment of the system allows reaching an equilibrium value as shown by the flattened portion of curves 94–98, or some fraction of the end-point equilibrium value, within about 2 to 30 seconds. In effect, the use of a biocompatible and metabolizable indicator and attendant data retrieval permits a measurement of CO to be carried out repetitiously over an extended period of time. The repetition or updating rate advantageously may be quite high, thus supplying the intensivist with substantially more current CO data.

In general, the indicator which is utilized under the precepts of the invention may be an anabolite or product of a constructive metabolic process, or a catabolite, or product which, by a destructive metabolic process, is converted into an excreted compound. In the latter metabolic category, the transformation which occurs represents a utility making energy available for organs in use. Desirably, enhanced measurement frequencies are made available with the procedure since there is no substantial hemodilution nor evoked body system instability. While relatively minor base line blood indicator concentration value shifting is encountered, the metabolic reaction to the introduced biocompatible analyte-containing fluid functions to maintain the patient in a stable condition.

Figure 4:
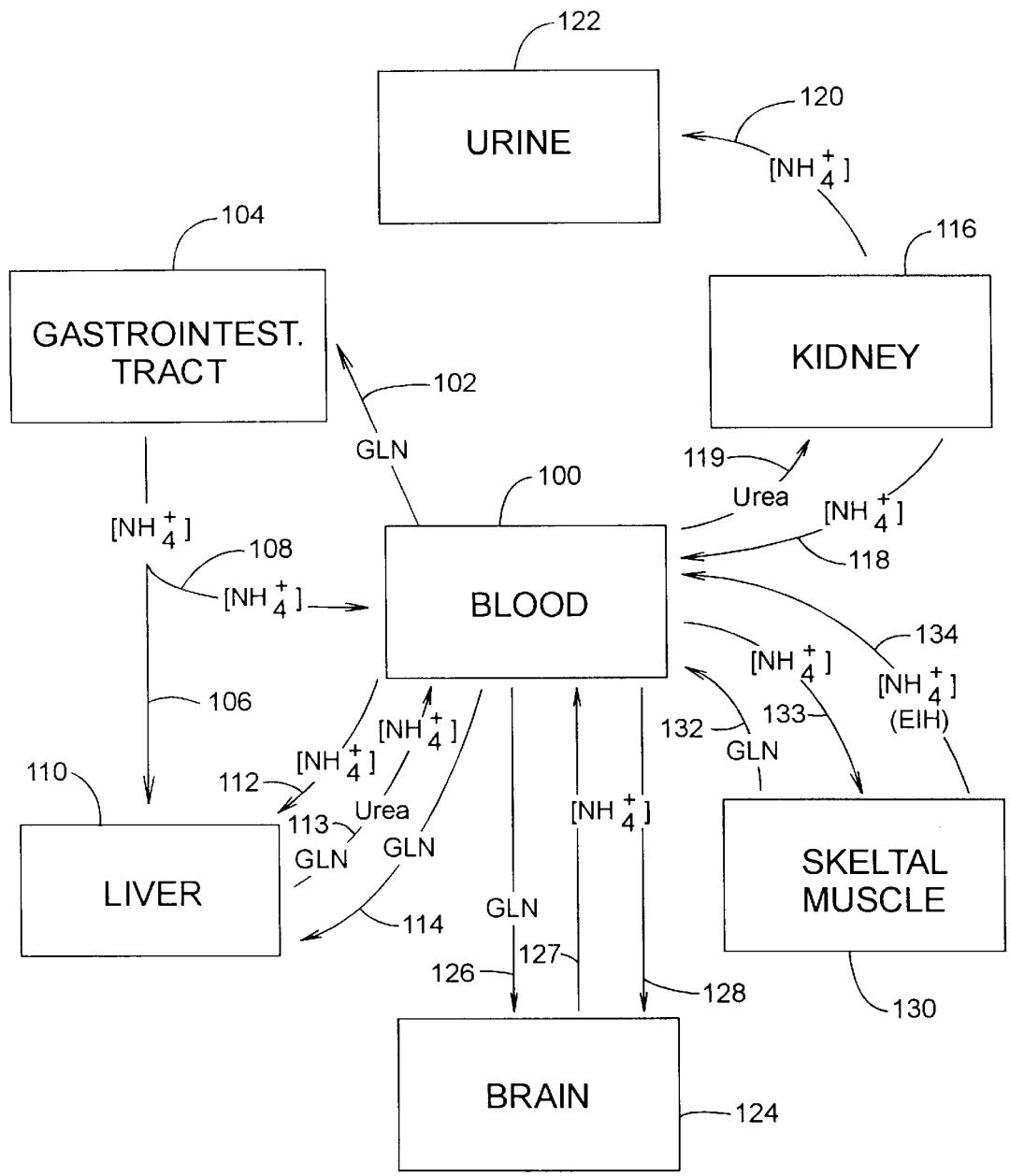
FIG. 4 is a block diagram illustrating the various sources, metabolism sites, and clearance pathways for ammoniacal products in the human body.

Ammoniacal fluid based indicators may be the subject of uptake by certain organs of the body for further catabolism and excretion, or they may remain in the body by anabolism or incorporation into other nitrogenous products. The amount of such indicator infused for each cardiac output measurement is based on the measurement precision of the sensor, the frequency of cardiac output measurements required per day, and the rate of metabolism. For the case of an ammoniacal fluid, the rate of metabolism or clearance of ammonia from the blood has been reported to increase with concentration. See in this regard: Lockwood, A. H., et al., "The Dynamics of Ammonia Metabolism in Man—Effects of Liver Disease and Hyperammonemia," *J. Clin. Invest.*, Vol. 63, pp 449–460, 1979). Under resting conditions, most blood ammonia/ammonium is of dietary origin. Normal digestive processes generate ammonia/ammonium from ingested protein, while bacteria in the gastrointestinal tract generate ammonia/ammonium by metabolizing protein products of dietary protein digestion and urea. An illustration of the major organs of ammonia/ammonium formation, utilization and circulation is presented in FIG. 4 including the various forms of nitrogenous compounds, e.g. ammonia gas ($NH_3$), ammonium ion ($NH_4^+$) or related nitrogenous by-products. Ammonia/ammonium metabolically formed in a given organ of the body is generally widely distributed. In FIG. 4, the blood pool or blood system is represented at block 100. Blood pool 100 is depicted supplying glutamine (GLN) to the gut or gastrointestinal tract as represented at arrow 102 and block 104. Ammonia generated in the gut as at 74 from protein digestion and deamination of glutamine (GLN) enters the portal venous circulation as represented at arrows 106 and 108 and is involved in the liver function as represented at block 110. The metabolic relationship of the blood pool or blood system 100 with the liver is represented by arrows 112–114. Metabolic interaction with the kidney as at block 116 is represented at arrows 118 and 119, while catabolic ammonium is excreted as represented at arrow 120 and block 122. Transport to and from the brain with respect to the blood pool is represented at block 124 and arrows 126–128. A similar metabolic interrelationship with respect to skeletal muscle is represented at block 130 and arrows 132 and 133. Exercise induced hyperammonemia will witness a transfer of ammonium ion into the blood supply as represented at arrow 134. It may be observed that such relatively short excursions thus are readily tolerated by the body. Short duration excursions occur with the present CO measurement system. See generally: "Exercise-Induced Hyperammonemia: Peripheral and Central Effects," Bannister, et al., *Int. J. of Sports Medicine*, 649 Vol. 11, pp 5129–5142 (1990). Under conditions typical of patients in an intensive care unit, resting muscles take up ammonia/ammonium from the circulating blood wherein the substance enters into protein synthesis via ketoglutaric and glutamic acid. When the muscle begins working again, ammonia/ammonium is once again released from the muscle into the bloodstream. If additional ammonia/ammonium (in the form of an ammonium salt solution) is injected into a peripheral vein, the added ammonia is brought directly to the tissue via the blood where it may be retained and eventually used for amino acid and protein synthesis. See: Furst, P., et al., "Nitrogen Balance After Intravenous and Oral Administration of Ammonia Salts in Man," *Journal of Applied Physiology*, Vol. 26, No. 1, pp 13–22 (1969).

Figure 5:
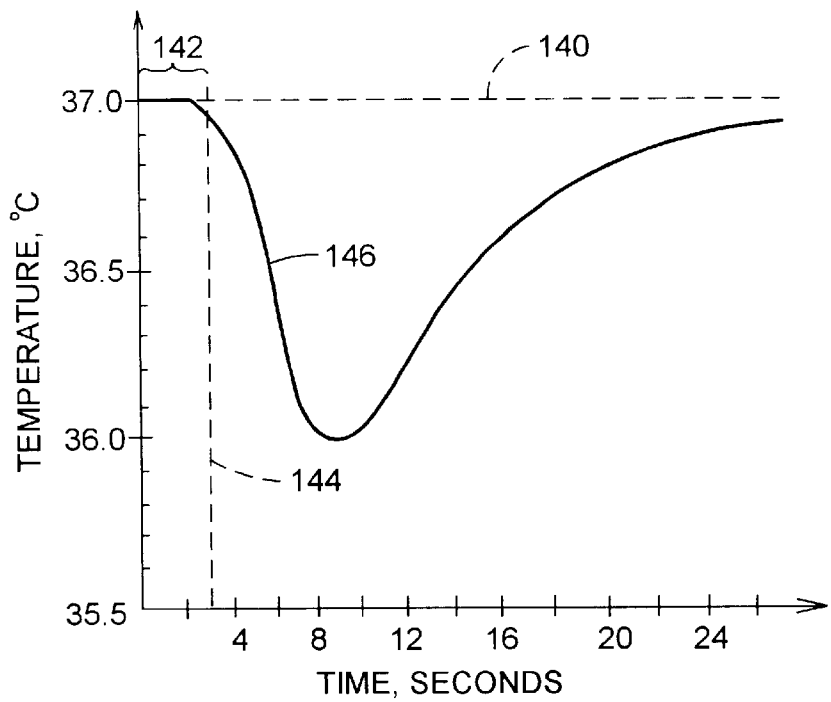
FIG. 5 is a curve illustrating the indicator dilution response of blood temperature to injection of a cold bolus of liquid in accordance with thermodilution techniques for measuring cardiac output.

The characteristic shapes of curves 94–98 as shown in FIG. 3 may be compared with a corresponding temperature/time response encountered in a conventional indicator-dilution approach for developing values of cardiac output, for example, procedures involving a brief injection of a cold saline indicator. In FIG. 5 a mixed venous blood baseline temperature is represented at dashed line 140 having a value, for example, of 37° C. A cold bolus then is injected in the manner discussed over a time interval represented within brackets 142 extending to the time line represented at dashed line 144. During the interval represented at 142, a 10 ml bolus of isotonic saline, for example, at a temperature of 5° C. may be injected at the entrance to the right atrium. Then, as represented by the temperature characteristic curve 146, a thermistor or thermocouple will respond at the region of the pulmonary artery to measure the relatively rapidly changing indicator value for temperature. By contrast, systems of measurement with the present approach may exhibit a relatively slower response time inasmuch as the indicator may be injected over a lengthier period and at a lower rate.

Figure 6:
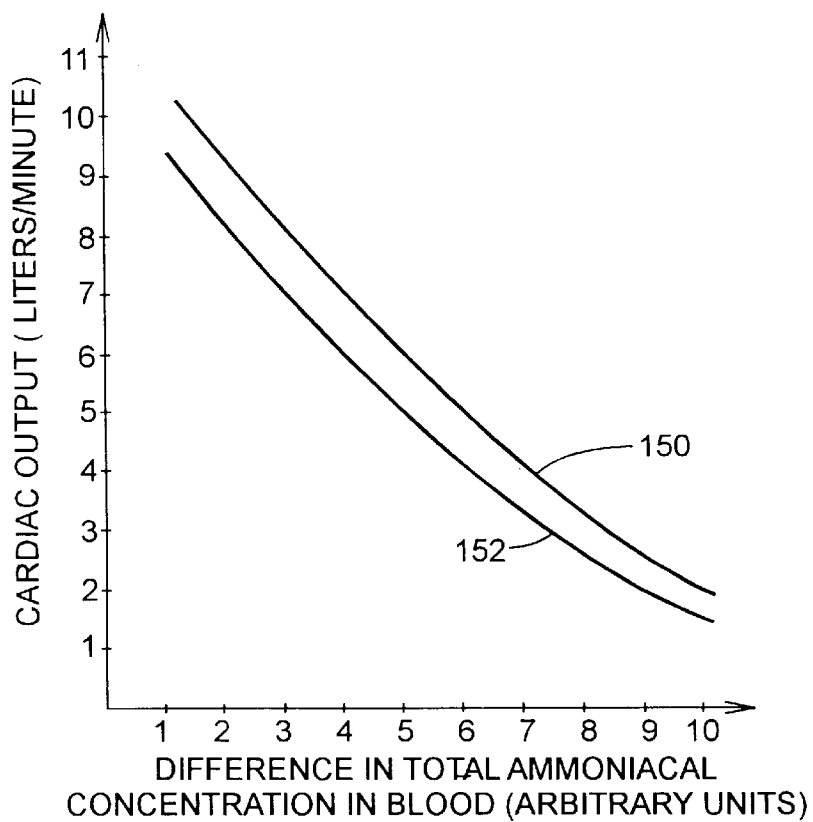
FIG. 6 illustrates the relationship between measured change in ammoniacal concentration in blood and cardiac output for known analyte-containing fluid injection rates.

Cardiac output, i.e., volumetric flow rate, is derived empirically as a function of the measured or controlled analyte-containing fluid injection rate, $m_I$, and the measured increase in blood indicator or analyte concentration. These relationships may be plotted. For example considering the preferred ammoniacal fluid as an analyte-containing fluid, looking to FIG. 6, the difference in the mixed total ammoniacal concentration in blood concentration, $C_a$ for a specific rate of analyte-containing fluid delivery is plotted with respect to cardiac output in liters per minute. Curve 150 plots the different values of cardiac output for a range of measured differences in blood indicator or analyte concentration with respect to an analyte-containing fluid injection mass flow rate of a predetermined value typically derived in milliliters per second. Lower curve 152 is at a lesser injection mass flow rate. As is apparent, a family of such curves will be evolved by a given system. This family of curves may be represented by the following expression where the analyte-containing fluid is ammoniacal fluid:

$$CO(t_i) = \frac{K * m_I * [IC_a - C_a(t'_i)]}{[C_a(t'_i) - C_a(t_i)]} \quad (1)$$

where

CO=cardiac output measured at time, $t_i$ (liters/minute);

K=constant;

$m_I$=mass flow rate of injection of ammoniacal fluid (liters/minute);

$IC_a$=total ammoniacal concentration of the analyte-containing fluid (predetermined indicator concentration) (micromol/liter);

$C_a(t'_i)$=total ammoniacal concentration of the analyte-containing fluid in blood measured during period of indicator infusion (blood indicator concentration) (micromol/liter);

$C_a(t_i)$=total ammoniacal concentration of analyte in blood measured prior to indicator infusion (baseline) (micromol/liter)

The measured volumetric output of the heart often is normalized to the size of the patient by dividing the measured cardiac output by the patient's "body surface area," BSA. (estimated in square meters), the latter parameter generally being derived based on the height and weight of the patient. This normalized cardiac output value is referred to as the cardiac index, CI, and is given by the expression:

$$CI(t_i) = \frac{CO(t_i)}{BSA} \quad (2)$$

Figure 7:
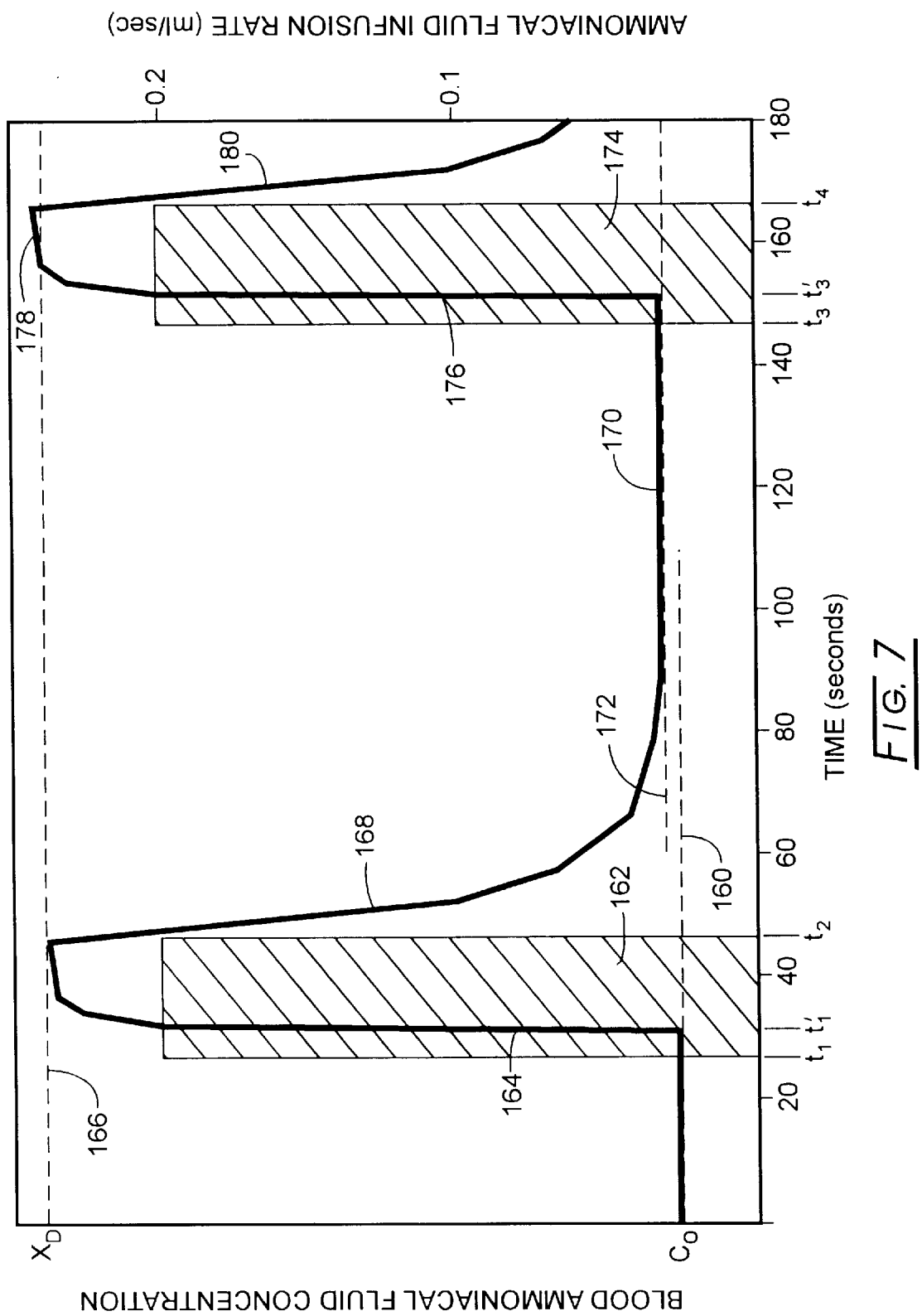
FIG. 7 is a graph schematically plotting blood ammoniacal fluid concentration with respect to a sequence of two cardiac output measurements carried out in accordance with the invention.

The procedure carried out with the system of the invention is one taking advantage of the complementary selection of analyte-containing fluid and analyte concentration sensor. That matching of system components and the selection of the analyte-containing fluid as being metabolizable within the body permits the carrying out of rapid measurement of cardiac output with substantial accuracy and without the need for averaging procedures. Using an ammoniacal fluid as the analyte-containing fluid for demonstration purposes, and referring to FIG. 7, the higher frequency measurement approach may be graphically illustrated. In the figure, two of a sequence of analyte-containing fluid infusion intervals are represented in conjunction with a time-related abscissa, a left-side ordinate representing blood ammoniacal fluid concentration and a right ordinate representing ammoniacal fluid or analyte-containing fluid infusion rate. With the procedure, following the positioning of a catheter within the bloodstream of the patient as discussed in connection with FIGS. 1 and 2, a baseline analyte concentration value in the bloodstream is measured with the analyte sensor. This value is converted to blood ammoniacal fluid concentration and represents a baseline value thereof shown as $C_0$ at dashed curve portion 160. The initial infusion of analyte-containing fluid or ammoniacal fluid for the instant demonstration then is carried out for an infusion interval represented at rectangle 162. The commencement of this infusion interval is represented additionally at $t_1$. As the ammoniacal fluid progresses in the bloodstream toward the analyte concentration sensor, there will be no elevation of the concentration sensor output. However, as the mixed analyte-containing fluid reaches the sensor as illustrated at time $t_1'$ in the figure, a very steep increase in blood indicator concentration is witnessed as is represented by the curve 164 rising from the baseline concentration at 160 to a peak concentration measured during the period of indicator infusion and identified by the dashed line level 166. A subsequent analyte concentration value is developed by the analyte concentration sensor from which the ammoniacal fluid concentration in blood is determined. From that value, then cardiac output (CO) may be derived as described in conjunction with expression (1) above. Note that the curve 164 then relatively rapidly falls as represented at curve region 168 following the cessation of infusion of analyte-containing fluid, and, further, as the infused ammoniacal fluid is, metabolized by the body. However, a new equilibrium level will be established at a baseline at the curve region 170, that new, slightly increased level being represented additionally by dashed line 172.

Two minutes later, the second infusion for cardiac output measurement is undertaken as represented at rectangle 174. Infusion interval 174 is shown to commence at time $t_3$. Following a short interval for permitting the mixed analyte-containing fluid to migrate to the sensor forward assembly, the concentration sensor will see a very steep increase in analyte concentration and, consequently, blood ammoniacal fluid concentration as represented by curve region 176 at time $t_3'$. As before, the curve region 176 will peak as shown at region 178. Note, however, that this peak will be slightly higher than the dashed peak line 166. This is occasioned by the slight increase in baseline as described at 172. The second infusion interval is seen to terminate at time $t_4$ and a rapid fall-off in ammoniacal fluid concentration in blood again is achieved as shown at curve region 180. This procedure reiterates over an extensive sequence of measurements. At the end of each infusion interval, the body again reaches a metabolic equilibrium level with respect to the analyte concentration at the newly-established baseline concentration level. This occurs over a sequence of measurements until a long-term equilibrium concentration level is reached with essentially no elevation as a final equilibrium of the metabolic activity and blood indicator concentration level is reached. Where the procedure employs ammoniacal fluid as the analyte-containing fluid, the peaks in concentration observed during the infusion intervals, as represented at dashed line 166 and curve region 178 will not have a detrimental affect on the body of the patient. In this regard, it may be recalled that the human body will experience ammonia/ammonium ion excursions in the course of exercise as discussed in connection with arrow 134 in FIG. 4. The system and method is capable of carrying out a cardiac output (CO) measurement as often as about 1 to 3 minutes in conjunction with an infusion interval of substantially less than that measurement frequency interval. The former infusion interval will be selected within about 2 to 30 seconds depending upon the determination of the clinician, the particular analyte employed, the concentration sensor utilized, and the mass flow rate of infusion of the analyte-containing fluid.

Figure 8:
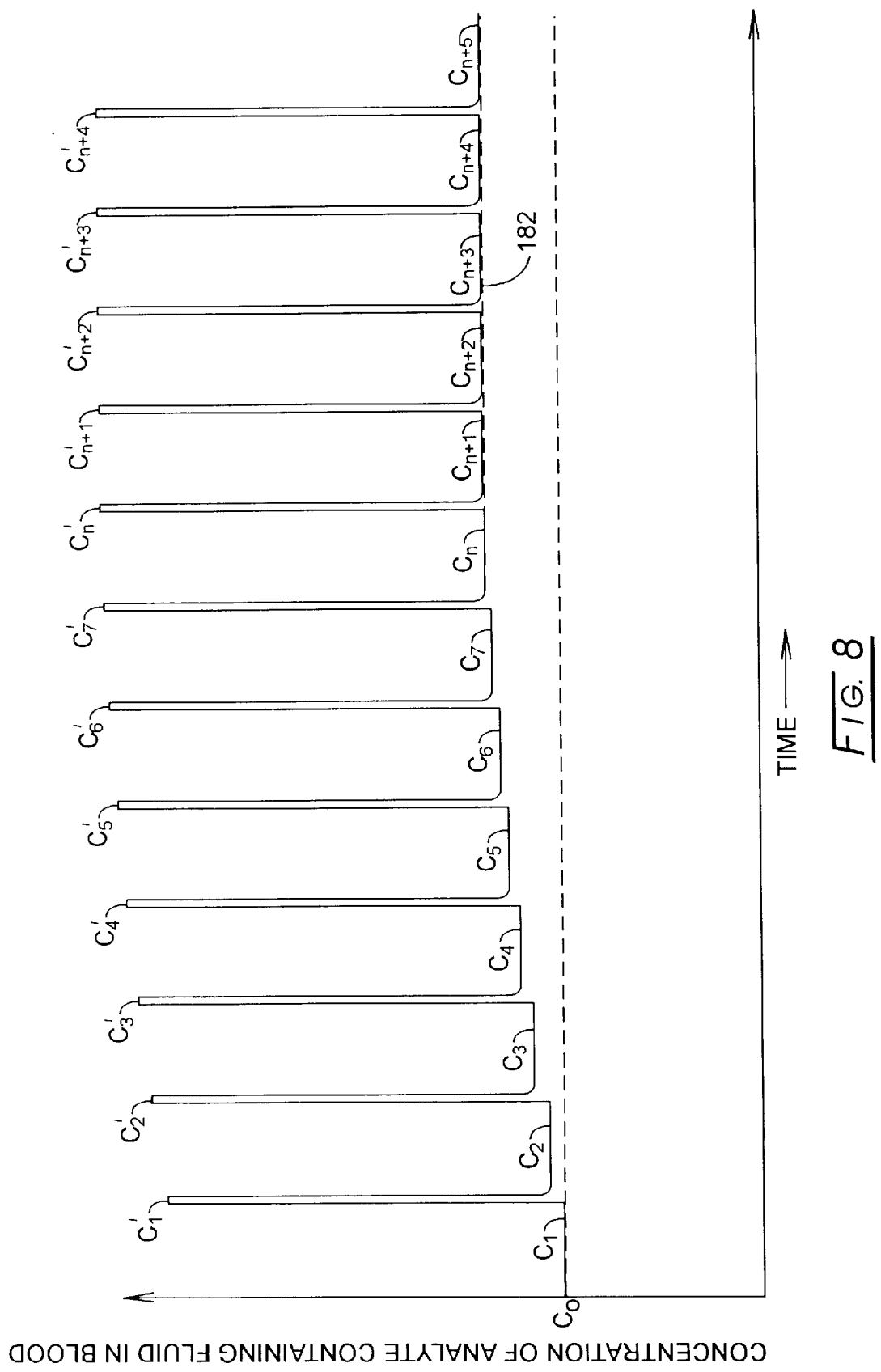
FIG. 8 is a graph schematically relating the concentration of analyte-containing fluid in blood with time and showing the development of a hemostatic level of analyte concentration in blood.

Turning to FIG. 8, a graphical representation of the equilibriation of the analyte in blood or blood indicator concentration with metabolic homeostasis of the body of the patient is provided. In the figure, the blood indicator concentration or concentration of analyte in the blood is represented along the ordinate, while time is represented along the abscissa, such time being associated with a sequence of cardiac output measurements. The figure shows a sequence of blood indicator concentration spikes, $C_1'-C_7'$ and $C_n'-C_{n+4}'$ which extend upwardly from respective baseline concentration levels $C_1-C_7$ and $C_{n+4}$. The width of each of the spikes corresponds schematically with the infusion interval of analyte-containing fluid into the bloodstream. Note that the baseline blood indicator concentrations increase with each cardiac output measurement as represented at baseline values C1 to about C7. During that period of the procedure, a metabolic equilibrium with the concentrations occurs and the concentration values elevate above the initial or initial baseline level $C_0$. However, as represented by the generally horizontal dashed concentration level line 182, a homeostatic level of blood indicator concentration will be reached following a sequence of CO measurements. At this point in the procedure, the average rate of infusion will be equal to the metabolic rate of the patient. This analyte concentration level corresponding with metabolic homeostasis of the body of the patient. As part of the system, the clinician may provide as an input to the controls of the system a homeostasis threshold value corresponding with a blood indicator concentration level or concentration level of the analyte representing a level below iatrogenesis (i.e., a safe concentration level). Where that threshold is exceeded, then the procedure is terminated, or a perceptible output, for example an alarm, is generated to alert the clinician.

For the preferred embodiment employing an ammoniacal fluid as the analyte-containing fluid, and, for example, employing a CO measurement frequency of 30 measurements per hour representing a measurement of cardiac output after two minutes, a preferred ammoniacal salt solution infusion rate is 0.5 to 5.0 ml per cardiac output measurement, while a more preferred infusion rate is 1.0 to 2.0 ml per cardiac output measurement. The indicator concentration or ammoniacal concentration of the analyte-containing fluid preferably is 10 mmol/liter to 250 mmol/liter, and more preferably is 30 mmol/liter to 120 mmol/liter. The rate of injection or infusion of the analyte-containing fluid for a given cardiac output measurement can be based on the previously measured cardiac output value. For example, at higher cardiac output levels, where the amount of dilution of the analyte-containing fluid is greater, the rate of the infusion can be greater in order to assure a more accurate cardiac output measurement. Conversely, at lower cardiac output levels, where the amount of dilution of the analyte-containing fluid is smaller, the rate of infusion can be smaller while still assuring an accurate cardiac output measurement.

By way of example, the following indicator injection rate may be programmed into the cardiac output monitoring system based on an infusion interval of 10 seconds:

TABLE I

| Previous Cardiac Output Measured Value (liter/minute) | Analyte-Containing Fluid Injection Rate (milliliter/second) | Measurement Interval (minute) |
|---|---|---|
| CO < 3.0 | 0.10 | 2.0 |
| 3.0 CO < 5.0 | 0.15 | 2.0 |
| 5.0 CO < 7.0 | 0.20 | 2.0 |
| 7.0 CO < 9.0 | 0.25 | 2.5 |
| CO 9.0 | 0.30 | 3.0 |

Using this cardiac output level dependent infusion rate, the amount of analyte-containing fluid infused per measurement can be selected to assure relatively uniform measurement accuracy over the entire range of physiologic cardiac output values, while minimizing the total amount of analyte-containing fluid infused into the body. The measurement interval can be adjusted according to the infusion rate such that during periods of high cardiac output, measurements are performed less frequently to assure that the total amount of analyte-containing fluid being infused over a period of time does not exceed predetermined limits. For instance, while the measured cardiac output level is above 9.0 liters/minute, the measurement interval is 3.0 minutes. At cardiac output levels of 7.0 and lower, the measurement interval is 2.0 minutes. This adjustment in the measurement interval assures that the infusion rate does not exceed the ability of the patient's body to metabolize the infused analyte-containing fluid. As is apparent, the continuing and frequent measurement of the analyte-containing fluid level in the blood and the selection of the noted threshold homeostasis will assure that such elected safe limits are not exceeded.

During the monitoring of a given patient, the number of cardiac output measurements carried out by the system range from less than 50 to greater than 2,000. After some number of measurements, the noted homeostatic level 182 is reached when the time-averaged rate of analyte component-containing fluid infusion matches the rate of metabolism and clearance of the injectate from the bloodstream. The body's natural homeostatic process within various organs and tissues serve to increase the rate of metabolism or clearance of the elevated analyte concentration which results from the infusions.

The selection of analyte-containing fluid for this indicator/dilution cardiac output measurement approach includes balancing the following optimal parameters:

(a) analyte measurement precision—increasing this parameter allows a smaller amount of analyte-containing fluid to be infused to achieve a target measurement accuracy for each measurement.

(b) background or baseline level of analyte-containing fluid—selecting an analyte-containing fluid whose baseline or background is low allows a greater fractional change in the analyte level for a given rate of analyte infusion.

(c) metabolism/clearance rate—selecting an analyte-containing fluid in which the body's rate of metabolism clearance is higher allows more frequent measurements of cardiac output without significant increase to the baseline concentration and, importantly, without exceeding safe concentration levels within the body.

(d) temporal stability of baseline level of analyte—the greater the short term stability of the baseline concentration of analyte in blood (i.e. during the period between measuring baseline analyte concentration and subsequent analyte concentration during the infusion interval which typically may range from several to tens of seconds), the greater the measurement accuracy for a given rate of analyte-containing solution injection (i.e. greater the ratio of signal to noise). This short-term stability of the baseline analyte concentration in the blood refers to the absence of significant baseline concentration changes due to such transients as: routine infusion of intravenous solutions and medicants; movements of the patient in bed; irregular breathing; and coughing.

(e) response time of sensor—the faster the response time of the sensor, the shorter the duration of infusion of the analyte-containing fluid. The shorter the duration of the infusion, the smaller the amount of analyte-containing fluid infused for each cardiac output measurement (for a target level of measurement accuracy) and the smaller amount of analyte-containing fluid infused for each cardiac output measurement (for a target level of measurement accuracy) and the smaller amount of analyte-containing solution must be metabolized or cleared by the body.

Now consider the instrumentation employed. As noted above, conventional catheter designs are utilized. However, the type of analyte concentration sensors employed will be seen to fall generally into two categories, optically-based, utilizing fiber optics, and ion selective electrode approaches. In the discourse to follow, the analyte concentration sensors are discussed in conjunction with a Swan-Ganz variety of pulmonary artery catheter as discussed in connection with FIG. 1.

Figure 9:
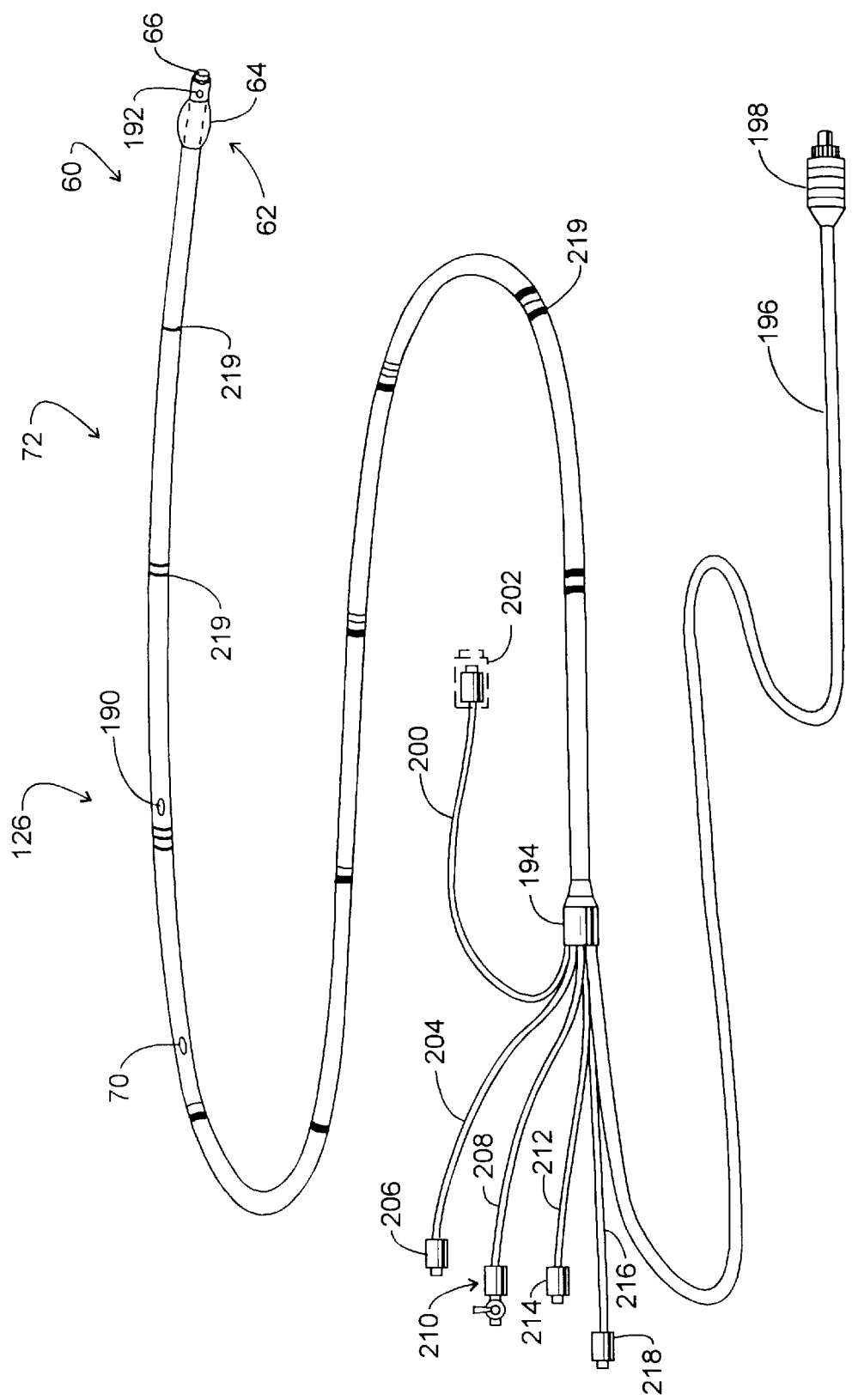
FIG. 9 is a pictorial view of a catheter employed in connection with a preferred embodiment of the invention.

Looking to FIG. 9, the catheter 60 described earlier in connection with FIG. 1 is illustrated at an enhanced level of detail. Catheter 60 incorporates an optically-based sensor forward assembly. Specific implementation of such assemblies are discussed in figures to follow. Accordingly, the catheter is again represented generally at 60 as including a tip region 62 incorporating a partially inflated balloon 64 and outer tip 66. A measurement region 72 extends from the tip 66 a dilution measurement distance to an infusion outlet or port 70 through which analyte-containing fluid is expressed. Typically, the infusion port 70 will be positioned about 30 cm behind the tip 66 and is positioned as discussed in connection with FIG. 1 such that the analyte-containing fluid is diffused or expressed into the bloodstream at a location near to and/or within the right atrium of the heart. Adjacent the infusion port 70, there is located an auxiliary port 190 which may be used in conventional fashion to introduce medicants into the bloodstream. The port 190 also may be employed to carry out a periodic cardiac output (CO) measurement utilizing the thermodilution technique with a cold bolus injection. Alternatively, a separate port may be provided for the cold bolus injections. Also located at the tip region 62 is a temperature sensor 192 which may be provided as a thermistor or the like and an open channel or lumen carrying a liquid which is utilized to monitor blood pressure at the pulmonary artery. For embodiments wherein an ammoniacal fluid is used as the analyte-containing fluid, the tip 66 will incorporate the forward assemblies of an analyte sensor, for example an ammonia sensor, and a pH sensor.

Catheter 60 terminates at a proximal end or end assembly represented generally at 194 wherein communication is made between its various channels, an analyte-containing fluid source, and associated control and monitoring features. As discussed above, an analyte-containing fluid is supplied at a controlled mass flow rate, $m_f$, from a conduit 196 terminating in a fluid transfer connector 198. Fiber optic assemblies, for example carrying fiber optics for analyte and for pH sensing extend from their forward assemblies at tip region 62 through an assembly 194 and cable 200 to an optical coupler 202. Optical coupler 202 connects to optical cable (not shown) which connects to photodetectors and light emitting diode type light sources as discussed later herein. Communication with the auxiliary port 190 is through tubing 204 which terminates in a fluid connector 206. Balloon 64 is inflated, for example, with carbon dioxide via a gas input at tubing 208 which terminates in a connector and valve assembly 210. The column of liquid channel opening at tip 66 and functioning to measure blood pressure extends from the end assembly 194 as tubing 212 which, in turn, terminates in a connector 214. Electrical leads which are coupled with the temperature sensor 192 extend from end assembly 194 via cable 216 which, in turn, is coupled with an electrical connector 218. Distance markers are provided on the catheter as represented, for example, at 219.

Referring to FIGS. 10 and 11, the structure of catheter 60 at the tip region 62 is revealed in sectional fashion. FIG. 10 is a developed view taken along the wedge-shaped section 10—10 shown in FIG. 11, while the latter figure is a sectional view taken along the plane 11—11 in FIG. 10. In FIG. 10, the tip 66 is shown to include a polymeric collar 220 which functions to block certain of the channels of the catheter 60 and to form the end component support for the optics and blood pressure related channels. In this regard, channel or lumen 222 extends through the catheter 60 and carries a saline solution for purposes of transmitting blood pressure witnessed at the tip 66. Balloon 64 is inflated from an internally disposed port 224 which, in turn, is in gas flow communication with a lumen or channel 226. Channel 226 is blocked at the collar 220 and receives an inflating gas such as carbon dioxide as earier-described. The two electrial leads 228 and 230 functioning in conjunction with thermistor or temperature sensor 192 extend through a channel such as that at 232 which also is blocked at tip 66 by the collar 220.

FIG. 11 reveals the presence of two channels at 234 and 236 respectively carrying fiberoptic assemblies represented generally at 238 and 240 which function in the measurement of analyte concentration and pH levels in the blood, respectively. For the preferred ammonia analyte measurement component, the pH level value is called for to compute the total ammoniacal content, i.e. total ammonium ion and ammonia gas. These optical assemblies 238 and 240 extend from forward assemblies of the concentration and pH sensors. FIG. 11 additionally reveals an analyte-containing fluid delivery channel 242 and an auxiliary IV channel 244. The latter two channels are blocked rearwardly adjacent their outlet ports.

Figure 12:
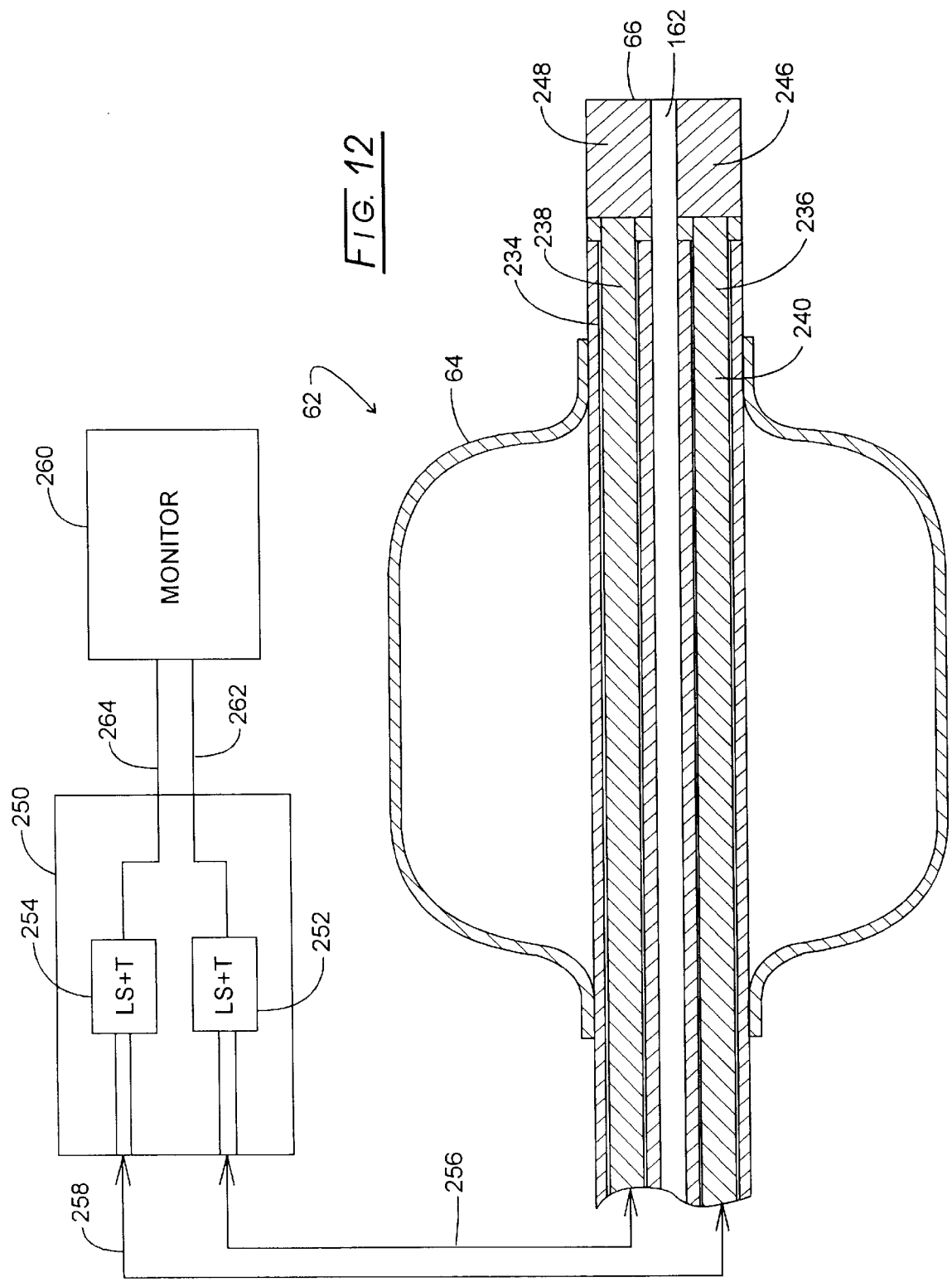
FIG. 12 is a partial sectional view taken through the plane 12—12 in FIG. 11 and showing concentration sensor front-end assemblies in schematic fashion as well as optical monitoring modules.

Referring to FIG. 12, the forward assemblies of the optical components at the tip region 62 are generally portrayed in block fashion in conjunction with a schematic representation of the components supporting them. A variety of adaptations for the optical determination of analyte or analyte component concentration and pH sensing are addressed in the discourse to follow. FIG. 12 shows that the fiber optic assemblies 236 and 238 extend to forward assemblies represented in block form, respectively, at 246 and 248, respectively having a pH sensor and analyte concentration sensor functions. Fiberoptic assembly 238 and its associated forward assembly 248 are operatively associated with a light source and transducer module represented generally at block 250. Module 250 includes two channels for providing a light source and transducing function as represented at interior blocks 252 and 254. The operative association between the analyte sensing fiberoptic assembly 238 and the module 250 is represented by dual arrow 256, while the corresponding association between the pH sensing assembly including fiberoptic assembly 236 and the module 250 is represented by dual arrow 258 seen communicating with light source and transducing block 254. Control over the light source and transducing functions represented at blocks 252 and 254 is shown asserted from a monitoring function represented at block 260 and respective lines 262 and 264. Optically-based monitoring systems as are associated with the module 250 and monitor 260 are marketed, for example, under the trade designation "ChemCard 2000" by Research International of Woodinville, Wash.

Referring to FIGS. 13 and 14, the infusion port or injectate outlet 70 is revealed as it is positioned in the analyte-containing fluid delivery channel 242. Note that the port 70 is located upstream from a channel plug or block 266, and is formed by locally removing a portion of the catheter wall adjacent the lumen or channel 242. The maximum widthwise dimension, represented in FIG. 13 at $L_1$, of the port 70 will range from 0.1 to 0.8 cm and preferably is within a range of 0.2 cm to 0.3 cm. The maximum widthwise extent of the port 70 is represented in FIG. 14 at $W_1$ and will range from 0.05 cm to 0.2 cm., and preferably will fall within a range from about 0.05 cm to 0.1 cm.

While not shown in the drawings, the catheter 60 may be configured to contain an additional channel which carries a third fiberoptic assembly which is coextensive in length with fiberoptic assemblies 238 and 240. This third channel may be employed to measure oxygen saturation level of the blood. Such measurements may be performed using reflectance oximetry methods as are described in the following publication:

Schweiss, J. F., "Continuous Measurement of Blood Oxygen Saturation in the High Risk Patient", Vol. 1, Beach International, Inc., San Diego, Calif., pp 1–12 (1983).

Additional description for such measurement is described in copending application for U.S. patent, Ser. No. 08/792,967, entitled "Method, System and Apparatus for Evaluating Hemodynamic Parameters" by Eggers, filed Jan. 24, 1997, now U.S. Pat. No. 5,788,647. Alternatively, one of the fiberoptic assemblies, for example assembly 238, may be employed for a dual purpose, including a determination of the oxygen saturation level of blood.

The type of sensor technology employed with the cardiac output monitoring catheters is selected in complement with the analyte-containing fluid utilized. Where optically-based techniques are employed, a variety of categories for the sensors are available. In all cases, however, the forward assemblies of the sensor systems must be within flowing blood as opposed to being located in cavities or the like where the blood may be captured and held quiescent. In general, the optical sensors include: direct spectrometric sensors; indirect spectrometric sensors; transmission spectrometric sensors; transmission/reflectance spectrometric sensors; colorimetric sensors; and fluorometric sensors. These sensors are described in conjunction with schematic representations of them in the figures to follow.

Figure 15A:
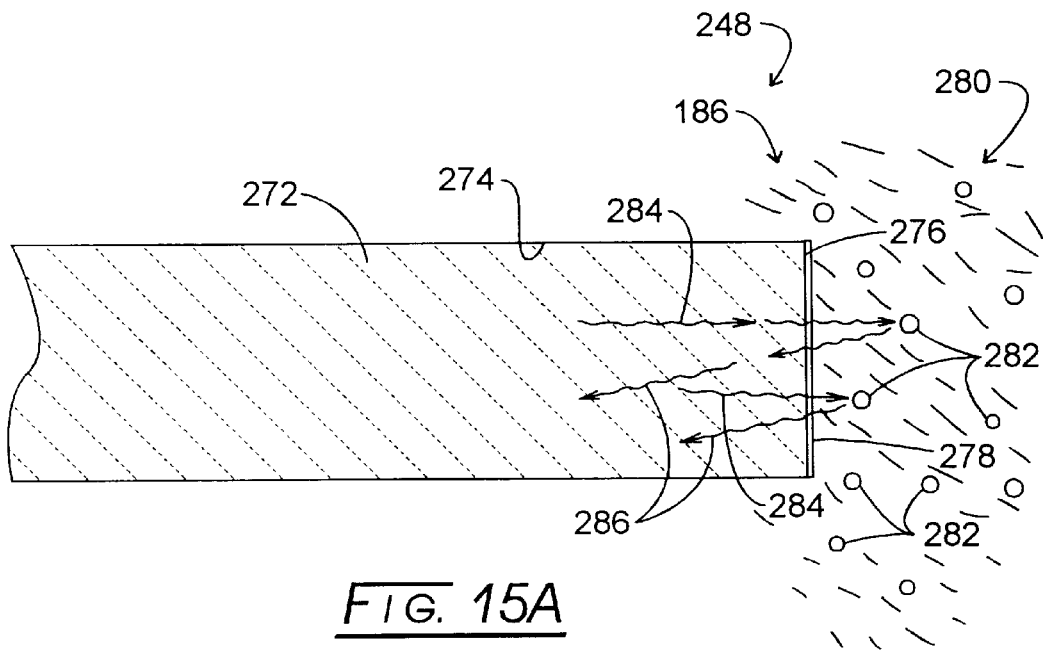
FIG. 15A is a schematic representation of a front-end assembly of a concentration sensor employed with the invention.
Figure 15B:
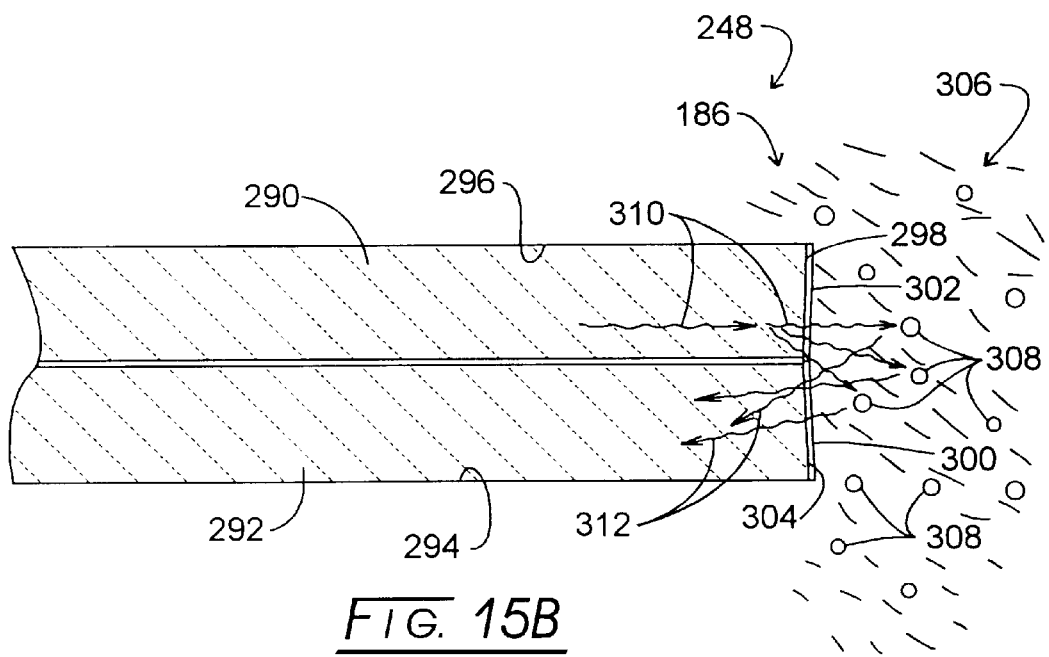
FIG. 15B is a schematic representation of the front-end assembly of a concentration sensor which may be employed with the invention.

Considering initially the direct spectrometric sensors, reference is made to FIGS. 15A and 15B. In the figure, the forward assembly 248 of the analyte concentration sensor is revealed. This sensor may, for example, directly measure ammonia gas as the analyte. With this arrangement, an optical fiber is shown as represented at 272. Fiber 272 is mounted within the sensor channel, for example, as represented at 234 in FIG. 11. The fiber 272 is surrounded along its lengthwise extent by a sheath 274. The tip of the fiber as represented at 276 is coated with a very thin, optically transparent coating 278. Coating 278 is an anti-coagulant such as heparin which functions to reduce the possibility of deposits such as fibrin or blood coatings over the tip 276. The embodiment of FIG. 15A is one wherein there is a simultaneous transmission of light at one or more predetermined wavelengths and reflectance reception of that light. In this regard, the bloodstream is schematically represented in general at 280. For the preferred embodiment, wherein ammonia gas ($NH_3$) is the analyte, analysis is made by light transmission to and reflectance from analyte component (ammonia gas) particles as represented at 280. Light transmission is schematically represented in the figure at 284 and its reflection is represented by the wave arrows 286. The reflected illumination as represented by the arrows 286 will exhibit a spectrum which is characteristic of the analyte component 282 and the intensity of the spectral portions thereof as related to the concentration of the analyte component 282 within the bloodstream 280. In general, the diameter of the fiberoptic component 272 is in a range from about 50 to 1,000 microns, and preferably falls in a range of about 100 to 500 microns. A typical diameter will be about 250 microns.

The transmission and reception of investigatory light at one or more predetermined wavelengths also may be carried out using two or more fiber components. In one approach, two fiber components are positioned in immediate adjacency. Alternately, one fiberoptic component may provide a transmission aspect while a group of such fiber components surmounting a central transmission fiber component carries out the opposite or reception function. In such an arrangement, the transmitted light and reflected or emitted light are advantageously separated during their transmission to and from the bloodstream. In FIG. 15B, the forward sensor assembly is again represented in general at 248. The fiberoptic assemblies employed with the optical sensor may be singular fibers which are typically formed of plastic or when formed of glass, typically are provided as bundles or multiple strands of glass. In the figure, two optical fibers are schematically represented at 290 and 292. The lengthwise extent of each of these fibers is enclosed within a sheath as represented, respectively, at 294 and 296. Tip surfaces 298 and 300 of respective fibers 290 and 292 are configured such that the tip surface 298 is slightly canted axially inwardly as is the opposite surface 300. Tip surfaces 298 and 300 additionally may be coated as respectively represented at 302 and 304, with an optically transparent anti-coagulant such as heparin. The overall diameter of the transmission/reflection separated assembly will be selected as the same as the overall diameter of the single fiber arrangement of FIG. 15A. In the figure, the bloodstream is represented in general at 306, and the measured analyte component, for example ammonia gas ($NH_3$) is represented at 308. With the arrangement shown, light of one or more wavelengths is transmitted through fiber assembly 290 as represented by the transmission arrows 310. Resultant reflection, as represented by transmission arrows 312 is collected and transmitted by fiberoptic assembly 292 for analysis. With this sensing forward structure, the transmitted light and reflected light are advantageously separated during their transmission to and from the bloodstream 306, and the analyte component 308 mixed therewith to enable the more accurate quantitative measures of spectral intensity and, in turn, more accurate measurement of the concentration of the analyte component 308. A concentration of more than one analyte or analyte component in the blood may be quantified by the use of appropriate light wavelengths for illumination and knowledge of the spectral characteristic of any other analytes of interest. By way of example, the direct measurement arrangement may be used to measure both ammonia ($NH_3$) concentration as well as oxygen saturation level of the blood. As before, the tip surfaces or forward assemblies and associated coatings 302 and 304 are immersed in flowing blood.

Figure 16:
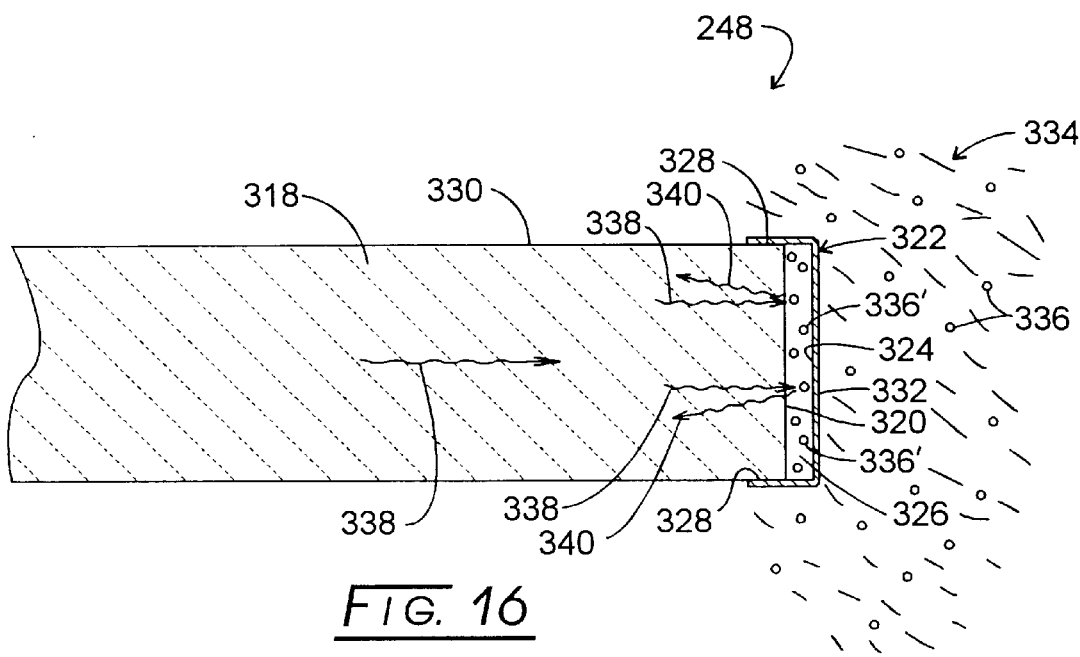
FIG. 16 is a schematic representation of a membrane containing front end assembly of a concentration sensor which may be employed with the invention.

Now considering indirect spectrometric sensor technology, reference is made to FIGS. 16, 17, 18A and 18B. In FIG. 16, the forward assembly of the sensor as represented generally at 248 includes a fiberoptic transmission/reception assembly 318 which extends to a tip surface 320. Positioned over the tip surface 320 is a cap-shaped membrane 322 having a forward inner surface portion 324 which is spaced from tip surface 320 to define a gap 326. A peripheral inner surface 328 of membrane 324 is sealed to the outer surface 330 of fiberoptic assembly 318 to assure the integrity of the gap 326. The outer surface 332 of the membrane 322 is in contact with flowing blood of the bloodstream represented generally at 334. As before, mixed with the blood of the bloodstream 334 is an analyte component, for example ammonia gas, particles of which are represented at 336. Membrane 322 is structured to contain microscopic pores and functions to minimize or block the ingress of water and other liquid components within the bloodstream 334 while permitting the analyte component of interest, for example ammonia gas, to rapidly diffuse across it due to a developed concentration gradient. In effect, a fluid space is developed at the gap 326 containing measured analyte component as represented at 336'. With the arrangement, an equilibrium develops between the analyte component 336' and analyte component 336. One or more wavelengths of light as represented by the transmission arrow 338 are transmitted into gap 326 and reflections from the analyte component 336' as are represented by transmission arrows 340 then may be analyzed. The intensity of the reflected light is represented by arrows 340, and the concentration of the analyte component is correlatable with the intensity of the light at one or more wavelengths. Light transmitted as represented at arrows 338 may be of specific wavelength or a spectrum of wavelengths may be measured. The advantage of this sensor structuring resides in the simplification of spectral analysis, inasmuch as the species of interest been separated from other blood-carrying species. The membrane 324 as well as the membrane employed with other embodiments of the invention may be provided as a Teflon® barrier, for example, manufactured by W.L. Gore & Associates, Inc. of Elkton, Md. These membranes contain microscopic pores whose size, for the ammonia analyte component, preferably is in the range from 0.02 to 3 microns. The overall thickness of the membrane 322 will be in the range of from 1 to 100 microns and, preferably, in the range of 10 to 50 microns. The hydrophobic nature of the Teflon® material serves to minimize ingress of water and other liquid components within surrounding blood.

Figure 17:
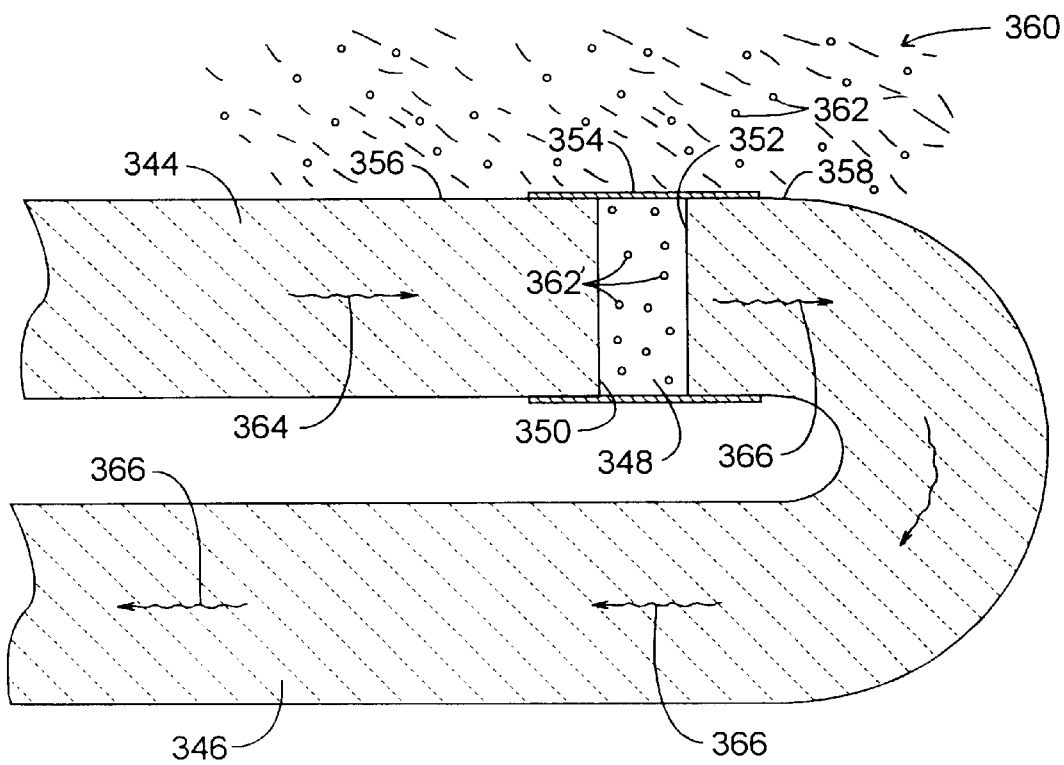
FIG. 17 is a schematic representation of a membrane-containing front end assembly of a transmission-type concentration sensor which may be employed with the invention.

A transmission spectrometric sensor, is illustrated in FIG. 17 where the optical sensor forward assembly 248 is schematically revealed for this adaptation. In the figure, the fiberoptic assembly is seen to have a general U-shaped configuration with a light transmission leg 344 and a return leg 346. Within the assemblage, there is, as in the case of the device of FIG. 16, a gap 348 defined between the end face 350 of leg 344 and end face 352 of return leg 346. A surmounting membrane 354 which may be of cylindrical shape is positioned across the gap 348 and sealed against the outer surfaces 356 and 358 of respective legs 344 and 346. As before, the membrane 354 is configured having microscopic pores which permit the ingress of analyte components from the bloodstream. In this regard, the bloodstream is represented, in general, at 360, and the analyte components, for example ammonia gas (NH$_3$) are represented at 362. With the arrangement, when the forward assembly 248 is immersed within the flowing bloodstream, the concentration gradient builds between the bloodstream 360 and the gap 348 to provide for the migration of analyte into the latter, such analyte being represented at 362'. Light having one or more wavelengths is transmitted toward the gap as represented by transmission arrow 364 to be selectively attenuated by the analyte 362'. The thus attenuated light then is returned for analysis as represented by transmission arrows 366 for analysis quantifying the concentration of analyte in the gap 348 and, hence, in the bloodstream 360. As in the case of FIG. 15, this arrangement has the advantage of isolating the analyte species of interest to simplify analysis.

Figure 18A:
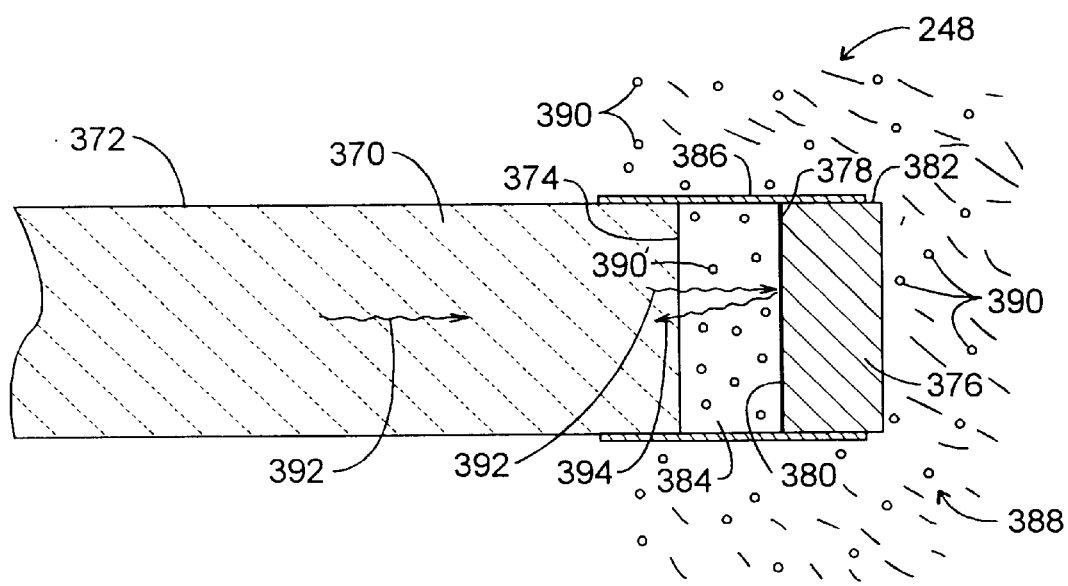
FIG. 18A is a schematic representation of a front end assembly of a concentration sensor which may be employed with the invention.
Figure 18B:
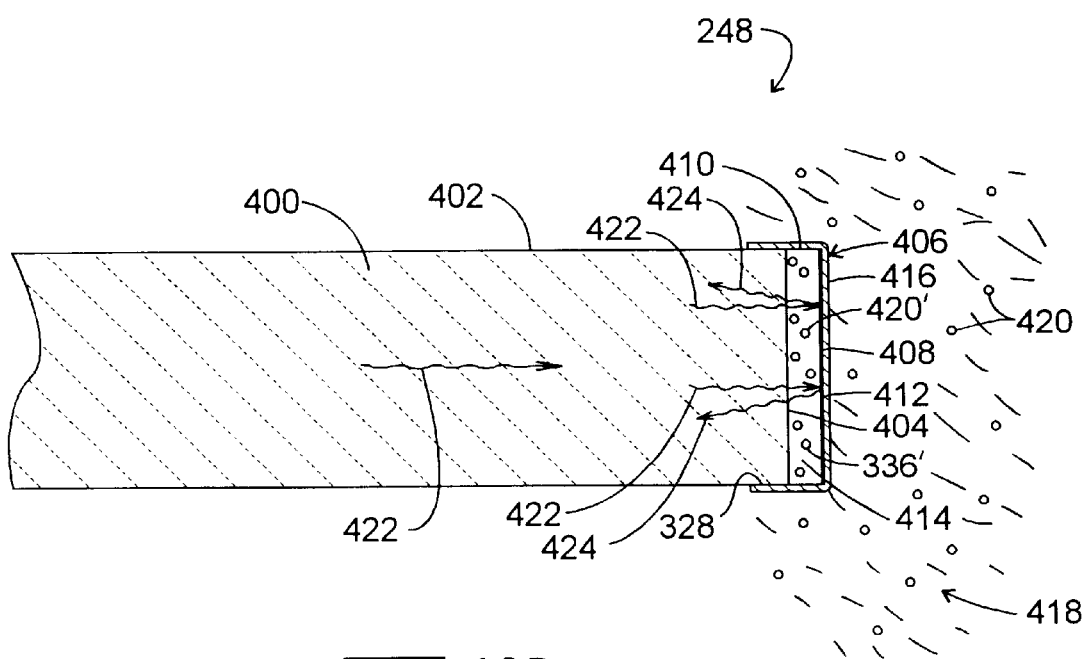
FIG. 18B is a schematic representation of the front end assembly of a concentration, sensor which may be employed with the invention.

Schematic representations of transmission/reflectance spectrometric sensors are provided in FIGS. 18A and 18B. Looking to FIG. 18A, the forward assembly 248 is seen to comprise an optical fiber assembly 370 having a side surface 372 and extending to a tip surface 374. Spaced from the tip surface 374 is a polymeric end piece 376 having an inwardly-disposed surface 378 which supports a light reflector provided as a coating or the like as seen at 380. The edge surface 382 of end piece 376 is dimensioned in correspondence with side surface 372 of the assembly 370.

Light reflecting surface 380 is spaced from tip surface 374 a distance defining a gap 384 and a cylindrical membrane 386 is seen to surround and further define the gap 384. In this regard, the membrane 386 is sealed to side surfaces 372 and 382. Forward assembly 248 is immersed in the flowing bloodstream represented, in general, at 388. Mixed with the bloodstream 388 is an analyte component as represented at 390. With the arrangement, a concentration gradient is developed between the bloodstream 388 and the gap 384, and the microstructure of the membrane 386 permits a migration of the analyte component into the gap as represented at 390'. Light is transmitted along the assembly as represented by transmission arrows 392, whereupon it is reflected from the light reflecting surface 380 and returns as represented by transmission arrow 394. The interaction of this light in crossing the gap 384 then is analyzed to develop values for the concentration of analyte component.

Referring to FIG. 18B, alternative structuring of the transmission/reflectance spectrometric sensor is revealed. The forward assembly 248 is seen to be structured incorporating a fiberoptic assembly 400 having a side surface 402 and extending to a tip surface 404. Positioned over the forward end of the fiberoptic assembly 400 is a cap configured membrane represented generally at 406 having an inwardly disposed surface 408 and a peripheral, cylindrically-shaped inward surface 410. Supported by the inwardly-disposed surface 408 is a light-reflecting component present as a coating and shown at 412. The peripheral inward surfaces 410 of the membrane 406 are sealed to the side surfaces 402 of fiberoptic assembly 400 to define a gap 414. Outwardly disposed surface 416 of membrane 406 is immersed in flowing blood of the bloodstream as represented in general at 418. Analyte component, as represented at 420 is mixed with the blood of the bloodstream 418. As before, the membrane 406 is configured having microscopic pores permitting the migration of the analyte component 420 into the gap 414 by virtue of the evolution of a concentration gradient between the gap and the bloodstream. Other components of the blood essentially are blocked from movement into the gap 414. Analyte component which has migrated into the gap 414 are represented at 420'. Analysis of the concentration of analyte component 420', which is equilibrated with the corresponding concentration of analyte component 420, is made by directing light at one or more wavelengths across the gap 414 as represented by transmission arrows 422. This light interacts with the analyte component 420' and is reflected from the reflector component 412 to return for analysis as represented by transmission arrows 424.

Figure 19:
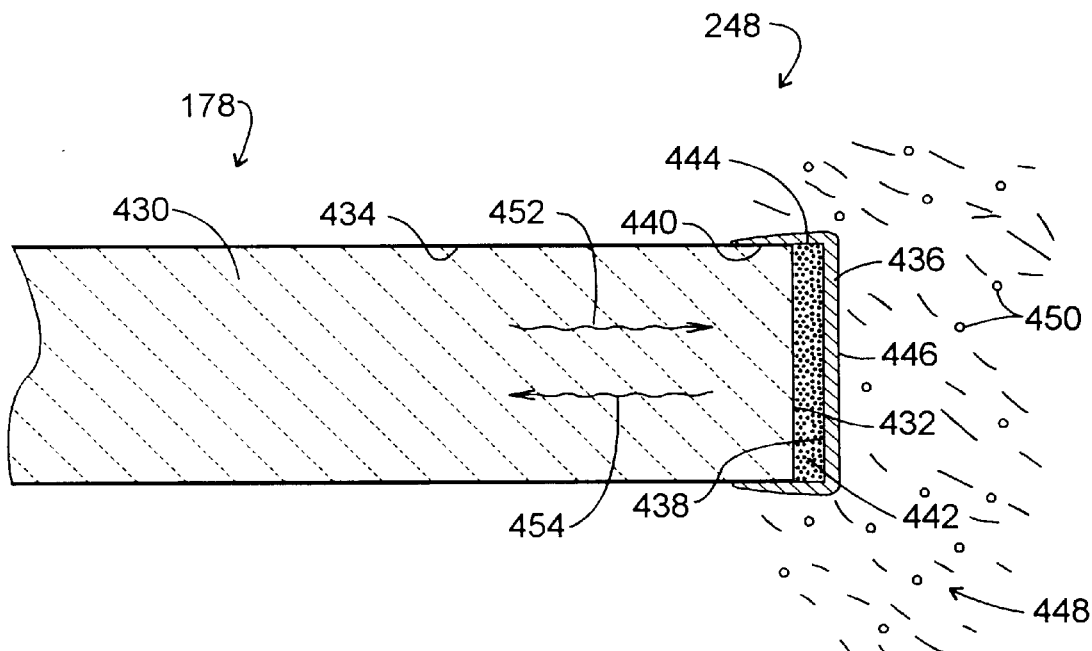
FIG. 19 is a schematic representation of a front end assembly for a concentration sensor which may be employed with the invention.

Referring to FIG. 19, a forward assembly is illustrated schematically which has a structure common to both colorimetric and fluorometric sensors. The sensor arrangement includes a fiberoptic assembly which extends to a tip surface 432 and is surrounded by a sheath 434. Mounted over the sheath and fiberoptic assembly is a cap-shaped membrane 436 having an inwardly-disposed surface 438 and an inwardly-peripherally disposed surface 440. Surface 440 is sealed to the outer surface of sheath 434 in a manner spacing the inward surface 438 from the tip surface 432 a distance defining a gap 442. Located within this gap is a reactor 444 which, for the structure shown, may be an analyte component responsive dye for the preferred colorimetric version of the sensor, or a reactor which fluoresces under light stimulation. The outward surface 446 of membrane 436 is immersed in flowing blood of the bloodstream as represented in general at 448 and containing analyte component as represented at 450. For the preferred embodiment of the invention, wherein ammonia ($NH_3$) is the analyte component and an analyte component-sensitive dye is employed for the reactor 444, the membrane 436 is configured having microscopic pores through which the analyte 450 may migrate and chemically react with the dye-defined reactor 444. This will result in a change in coloration of the dye which may be analyzed by colorimetric procedures. Accordingly, the reactor 444 is seen stimulated by light at one or more wavelengths as represented by light transmission arrow 452. The resultant light reflected from the reactor dye is represented at transmission arrow 454. A system utilizing ammonia as the analyte and an ammonia sensitive dye as the reactor 444 is a preferred embodiment of the invention. Of the ammonia dyes available for use as the reactor 444, bromocreosol green, excited at wavelengths in first band of 380 to 480 nm, in second band of 520 to 680 nm, and third band of 700 to 900 nm; chlorophenol red excited at wavelengths in first band of 380 to 420 nm, in a second band of 520 to 620 nm, and in a third band od 650 to 900 nm; bromophenol blue excited at wavelengths in first band of 380 to 440 nm, in second band of 520 to 640 nm, and third band of 700 to 900 nm; m-creosol purple; thymol blue; and congo red may also be considered. The light wavelengths for stimulation conventionally are generated by light emitting diodes (LEDs) and the wavelengths utilized are based upon the wavelengths corresponding to the peak absorption intensity and wavelengths which are insensitive to changes in the ammonia concentration. If a plastic fiberoptic assembly is used, the preferred third wavelength is about 700 nm. If a glass fiberoptic light transmitting assembly is used, the preferred third wavelength of those cited above is within the range specified. Dyes serving as reactor 444 quite rapidly reach an equilibrium with the analyte component 450. The intensity normalized reflectance of the responding wavelength of light 454 is utilized to quantitate the concentration of analyte component (e.g. ammonia).

Where the reactor 444 is provided as an analyte-sensitive fluorescent material, then upon excitation by light wavelengths as represented at arrow 452, the level or intensity of fluorescence or the rate of quenching when a stimulation source is extinguished is correlated with the concentration of analyte component 450.

Referring to FIGS. 20A and 20B, the light source and transducing function 254 described in conjunction with FIG. 12, representing a component of the optical coupler 202 described in conjunction with FIG. 9 is revealed in more detail. This particular assembly is utilized with the colorimetric embodiment of FIG. 19 wherein the reactor is an analyte component-sensitive dye, preferably sensitive to ammonia ($NH_3$). In FIG. 20A, the fiber assembly 430 is seen extending to a step-down chamber 460. A singular fiber optic assembly 430 is positioned in light exchange relationship with an assemblage of seven fiberoptic components or channels represented generally at 462. These discrete fiberoptic components include a component 464 which transmits light at a wavelength of 450 nm from an LED source 466; a transmitting component optical fiber component 468 which transmits light at a wavelength of 615 mm from an LED source 470; and a fiberoptic component 472 which carries light at a wavelength of 700 mm from an LED source 474. Reference fiberoptic components 476, 478, and 480 transmit light from respective sources 466, 470, and 474 to a photodiode reference function represented at block 482. Light returning from impingement upon the analyte component sensitive dye (arrow 454) is collected or gathered and transmitted by core gathering fiberoptic components 484–487. Optical components 484–487 are directed to a combining input at a photodiode sensor signal represented at block 488.

Figure 21:
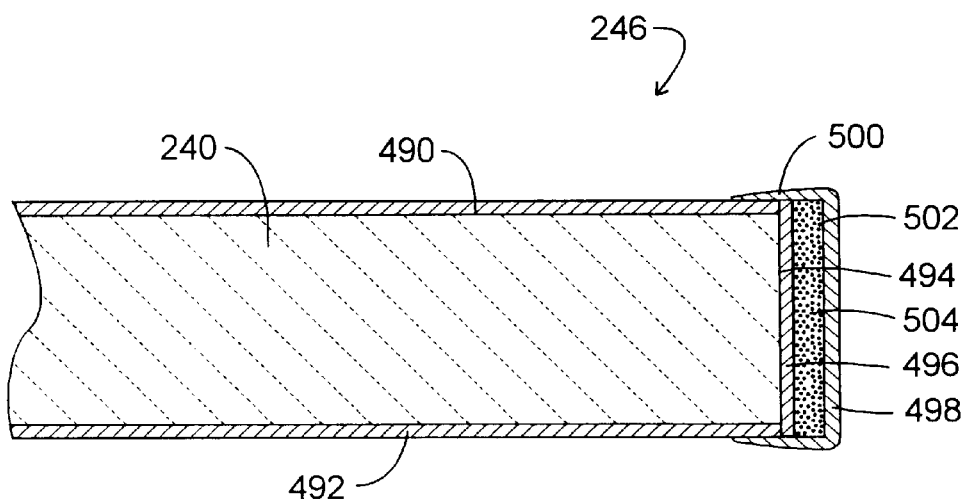
FIG. 21 is a schematic representation of the front end assembly of an optical pH sensor which may be employed with the invention.

Looking to FIG. 20B, a cross-section of the assemblage 462 is provided. The gathering component 484 is seen centrally disposed within the assemlage 462 while remaining gathering components 485–487 are disposed symmetrically about it. Transmitting fiberoptic components 464, 468, and 472 have the same diameters and are seen to be symmetrically disposed about the centrally disposed collecting component 484. With this arrangement, about 11% of the source light from sources 466, 470, and 478 is transmitted to the reactor 442 and about 44% if the light reflected from reactor 442 is transmitted to the photodiode detector 488.

Where the analyte component is, for example ammonia or carbon dioxide, in order to derive the value of total indicator concentration, i.e. the concentration of the analyte fluid in blood, the value of the pH of the blood may be utilized in a straightforward computation to find total concentration. pH may be measured with a variety of techniques using reactors which are chemical or ion selective electrode-based. A pH sensitive dye is employed in conjunction with the embodiment described in conjunction with FIGS. 11 and 12. Looking to FIG. 21, the front end assembly 246 represented generally in FIG. 12 is revealed in schematic fashion but at an enhanced level of detail. In the figure, the fiberoptic assembly 240 as it is present at the forward assembly 246 again is represented. The outer cylindrical surface 490 is covered with a sheath 492 and the tip surface 494 of the fiberoptic assembly 240 is coated with a pH sensitive dye which is applied as a porous coating and represented at 496. Sealingly positioned over the tip surface 494 and the dye 496 is a hydrogen ion permeable membrane 498 which is cap-shaped having a cylindrical side component 500 sealed to the assembly 240 and sheath 492. The inner forward surface 502 of the embrane 498 is spaced from the dye layer 496 to accommodate a medium 504 whose pH is in equilibrium with the pH of the blood within which this forward assembly 246 is immersed. The pH sensitive dye is interrogated by light at one or more wavelengths to determine the value of pH of the blood in the flowing bloodstream. For the present embodiment, the forward assembly of the pH sensor is at the tip of the catheter 60. It may perform at other locations, for example adjacent the injectate port 70 or behind the balloon 64.

Analyte concentration sensing systems can be configured using technologies other than those which are optically based. Where such alternate approaches are utilized, some modification of catheter design is undertaken.

Figure 22:
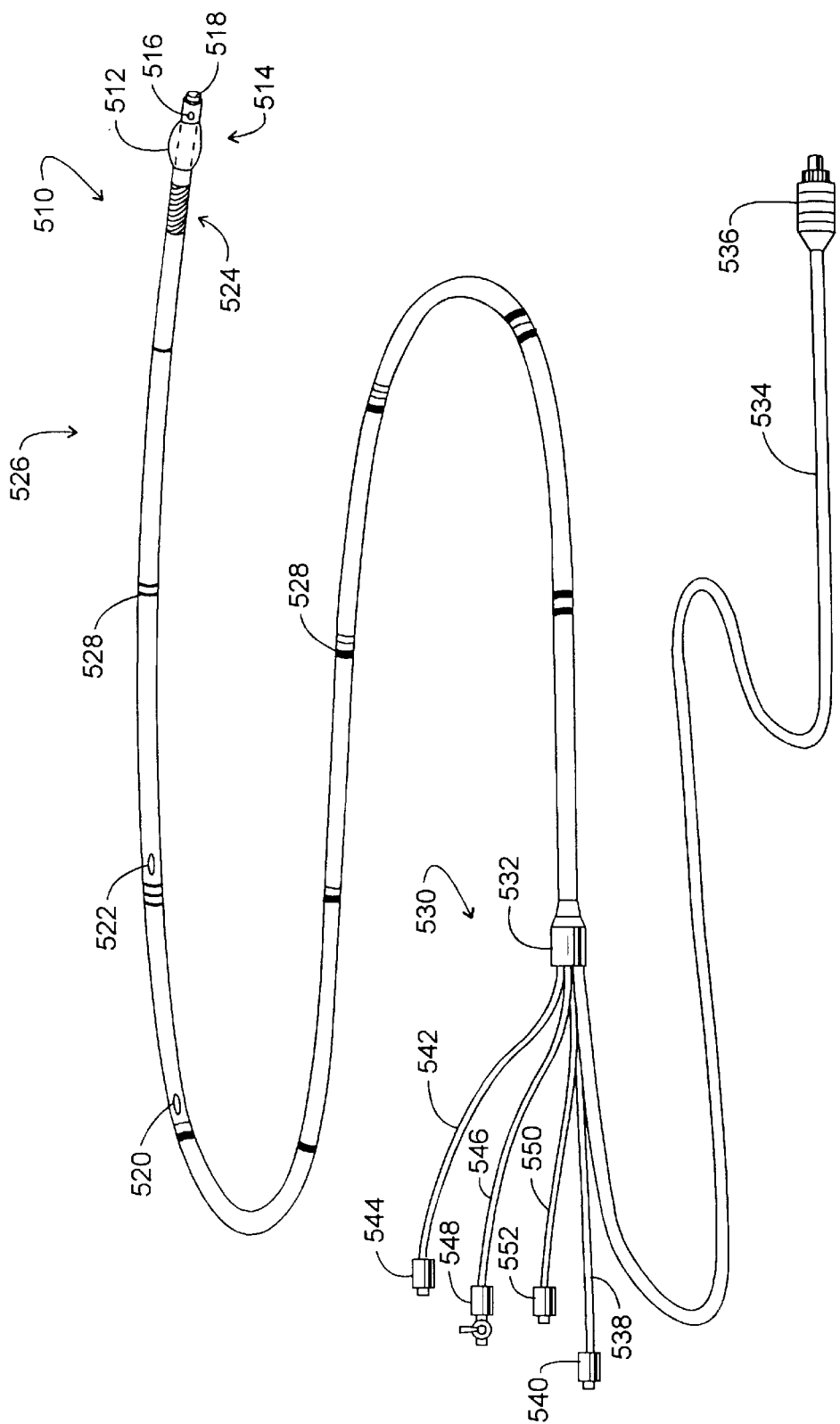
FIG. 22 is a pictorial view of a catheter incorporating a concentration sensor with non-optical technology.

Referring to FIG. 22, a catheter is shown at 510 being structured with a concentration sensor which is non-optical in design. As before, the concentration sensor design may be incorporated in those catheters suitable for carrying out dilution method cardiac output measurement, including the embodiments of FIGS. 1 and 2. Device 510, as before, generally is of a Swan-Ganz type having a partially inflated balloon 512 at its tip region 514. The catheter may employ a variety of analyte concentration sensor technologies, for example, sensors based upon amperometry and voltometry as well as Schottky diode-based technologies and acoustic-wave based technologies. Also located at the tip region 514 is a temperature sensor 516 which may be provided as a thermistor or the like and an open channel or lumen carrying a saline solution which is utilized to monitor blood pressure at the pulmonary artery. This blood pressure monitoring channel opens at the outward tip surface 518. Spaced rearwardly from the tip surface 518 a distance selected for dilution measurement is an infusion outlet or injectate port 520. Typically, the port 520 will be positioned about 20 to 30 cm behind the tip region 514 and will have a size selected for achieving a desired mass flow rate for the expression of the analyte-containing fluid injectate. In general, the port 520 is positioned such that analyte-containing fluid is injected into the bloodstream at a location near to and/or within the right atrium of the heart as discussed in connection with FIG. 1. Somewhat adjacent to port 520 there is located an auxiliary port 522 which may be used in conventional fashion to introduce medicants into the bloodstream. Port 522 also may be employed to carry a periodic cardiac output (CO) measurement utilizing the long recognized thermodilution technique with a cold bolus injection. The forward assembly of the concentration sensor is shown at 524 adjacent the balloon 512. For most implementations of this form of forward assembly, a membrane of the nature discussed above is employed. This sensor, the components within the tip region 514, and the ports 520 and 522 fall within a measurement region represented generally at 526 of catheter 510. Catheter 510 is dimensioned in correspondence with catheter 60 as described in connection with FIG. 1 and, in similar fashion, includes distance indicators, certain of which are represented at 528. The catheter extends to a proximal end region represented generally at 530 and incorporating an end assembly 532. From end assembly 532, connection is made with a variety of monitoring and control components as well as connection with the control source of analyte-containing fluid injectate. In this regard, the analyte-containing fluid injectate is supplied at a controlled mass flow rate, $m_f$, from a conduit 534 terminating in a connector 536. Electrical leads extending from thermistor 516 as well as from concentration sensor forward assembly 524 extend via cable 538 to a connector 540. Communication with the auxiliary port 522 is through tubing 542 which terminates in a fluid connector 544. Balloon 512 is inflated, for example, with carbon dioxide, via a gas input at tubing 546 which terminates in a connector and valve assembly 548. The column of liquid channel extending to tip surface 518 for purposes of blood pressure monitoring extends from end assembly 532 via tubing 550 which, in turn, terminates in a connector 552.

Referring to FIGS. 23 and 24, the structure of the catheter 510 at the forward assembly 524 of the concentration sensor is revealed. The outer end of the tip region 514 incorporating temperature sensor 516 is structured identically as the corresponding sensor 192 described in connection with FIG. 10. Seen in FIG. 23, in the region of balloon 512 is an inflation/deflation channel 554 which is blocked at a plug 556 to establish an ingress/egress port 558 for carrying out the selective inflation of the balloon 512. Extending along the channel at the centerline of the catheter 510 is a blood pressure channel 560, while directly opposite the inflation channel 554 is an electrical lead channel 562. Channel 562 appears in FIG. 24. At this location, the channel retains two electrical leads 564 and 566 extending from the temperature sensor 516 (FIG. 22). Concentration sensor 524 is structured as an ion-specific electrode-based device, and is formed having an outwardly-disposed, cylindrically-shaped membrane 568. Membrane 568 is provided as a microporous, hydrophobic polymer such as the earlier-described Teflon® or polytetrafluoroethylene. In effect, the membrane 568 is semi-permeable to the ion of interest. For the case of an ammoniacal fluid performing as the analyte-containing fluid, in general, the ammonium ion ($NH_4^+$) becomes the analyte component. FIG. 24 reveals the presence of an inwardly disposed cylindrical polymeric wall 570 spaced inwardly from the cylindrical membrane 568 to form a fluid retaining annular gap 572 which extends between a cylindrical end plug 574 and a corresponding fluid block provided as an outer wall 576. Within gap 572 is an electrolyte or electrically conducting liquid 578. Where the analyte-containing fluid is an ammoniacal fluid, the liquid 578 may be a solution containing 0.1 molor ammonium chloride. That liquid 578 reaches equilibrium with a blood carried ammonium ion flow across the membrane 568 to change or alter the pH of the solution of liquid 578. In effect, the device becomes a pH sensor. As is apparent, the liquid 578 must be related to the analyte which is being measured. For the ammonium ion analyte component considered, the higher the concentration of ammonium ion in the bloodstream, passing over the membrane 568, a corresponding effect will be observed in the ammonium ion concentration in liquid 578. Ion selective electrodes are employed to measure this ion concentration within liquid 578. In this regard, the outwardly-disposed surface of cylindrical wall 570 is coated at a forward region of the forward assembly 524 with a pH electrode which may be implemented as a glass electrode selective to the hydrogen ion. Such an electrode is shown at 580. Electrode 580 may be a glass comprising silicon dioxide, lithium oxide, and calcium oxide in the ratio 68:25:7. Note in FIG. 23 that electrode 580 extends from cylindrical end plug 574 to an edge or termination at 582, and is connected to an electrical lead 584 which extends into the electrical lead channel 562. A cylindrically-shaped reference electrode 586 completes the forward assembly 524 (FIG. 23). This second electrode 586 may be provided as a metallic coating, for example, silver/silver chloride. Electrode 586 is spaced from the glass electrode 580 but remains operationally associated therewith within the electrolyte containing cavity or gap 572. The electrode 586 is connected to a lead 588 which also is extended into the electrical lead cavity 562 as seen in conjunction with FIG. 26.

In operation, the electrical leads 584 and 588 are connected across a potentiometric based sensing system, where the analyte component is ammonia ($NH_3$). As blood within the bloodstream within which is mixed the analyte-containing fluid, moves across the hydrophobic membrane 568, ammonia gas vapor diffuses through the membrane and into the electrolyte 578. Changes in the measured potential between the glass electrode 580 and the reference electrode 586 are in correspondence with the change of pH within the electrolyte 578 and, are proportional to and correlatable with the blood ammonia concentration of the bloodstream adjacent the concentration sensor 524. The value of cardiac output (CO) may be computed in correspondence with expression (1) above. Sensor 524 may perform in either the above-noted potentiometric mode wherein voltage across the reference and glass electrode is determined, or may operate in amperometric mode wherein the current flow between these two electrodes is evaluated during the application of a small D.C. voltage difference.

Additionally seen in FIG. 24 is the auxiliary channel 586 communicating with port 522 (FIG. 22) and with connector 544 through tube 542. The figure also reveals the indicator or analyte-containing fluid delivery channel 592 which will have been blocked off just beyond the location of injectate port 520. Blood pressure channel 560 appears centrally in FIG. 24.

Referring to FIGS. 25 and 26, the commencement of the measurement region 526 at the infusion port or inlet 520 is revealed at a higher level of detail. Catheter 510 now is formed with the enlarged outer cylindrical wall 576 described in connection with FIG. 23. That cylindrical wall reappears in the instant figures. The structuring of the port 520 is the same as discussed in connection with FIG. 9. FIGS. 25 and 26 show that port 520 extends through the enlarged wall 576 and is in fluid transfer communication with the analyte-containing fluid delivery or infusion channel 592. That channel receives a controlled mass flow rate of analyte-containing fluid during an infusion interval. Note that the delivery channel 592 is plugged or blocked with a plug 594. FIG. 26 reveals that the electrical lead carrying channel 562 of the catheter 510, as it extends rearwardly from the electrode/electrolyte-based analyte concentration sensor forward assembly 524 (FIG. 24) incorporates four leads, to wit, 564, 566, 584, and 588, which terminate at the earlier-described cable 538 and connector 540.

Figure 27:
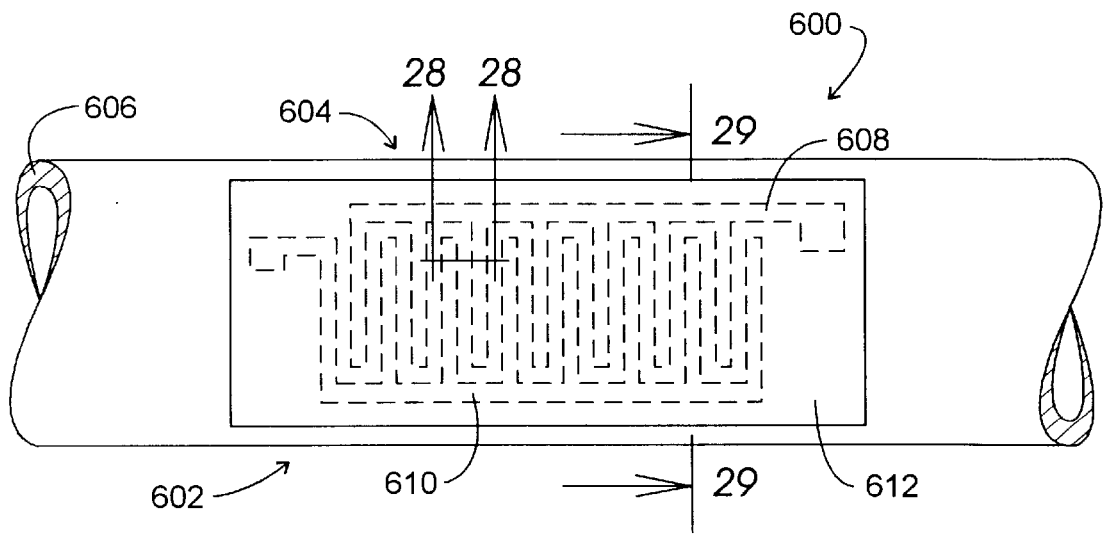
FIG. 27 is a schematic diagram of a Schottky diode-based analyte concentration sensor.
Figures 28, 29:
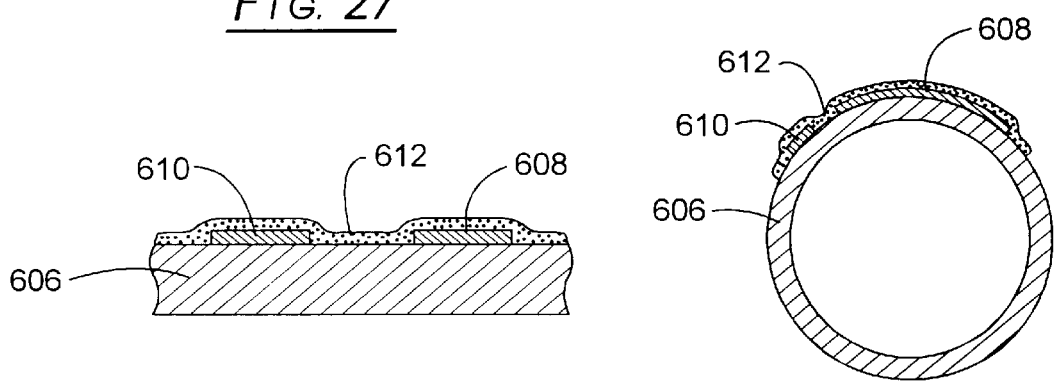
FIG. 28 is a side view of the sensor of FIG. 27.
FIG. 29 is a sectional view taken through the plane 29—29 in FIG. 27.

Now looking to the utilization of Schottky diode-based concentration sensors, reference is made to FIGS. 27–29. In these figures, the concentration sensor is represented in schematic fashion. Looking to FIG. 27 the measurement region 600 of a catheter 602 of a variety described in connection with FIGS. 1 and 2 is seen to incorporate the front-end assembly 604 which employs a technology based upon the interaction of planar Schottky barrier diodes with analytes or analyte components. In this embodiment, the sensor 604 is mounted upon, for example, a wall 606 corresponding with a wall as at 576 described in connection with FIG. 26. Sensor 604 is formed having two metal electrodes configured in spaced relationship and in interdigitated geometry. These electrodes are provided as a gold electrode 608 configured in conjunction with an aluminum electrode 610. Gold electrode 608 creates an ohmic contact and aluminum electrode 610 creates a Schottky barrier contact with oli(3-octylthiophene)(3POT). The conducting polymer 612 exhibits an electrical conductivity which is correlatable with the concentration of the analyte or analyte component being employed. Conducting polymer 612 may be substituted polypyrroles, polythiophenes, or polyanilines. Not shown in the drawing is an analyte or analyte component permeable membrane as discussed earlier herein which covers the active sensor components. These active components provide a noted reactor function. The outer surface of the membrane, as before, is in contact with flowing blood of the bloodstream. See generally Assadi, A. et al., "Interaction of Planar Polymer Schottky Barrier Diodes with Gaseous Substances", Sensors and Actuators, B, Vol. 20, pp 71–77 (1994).

Figure 30:
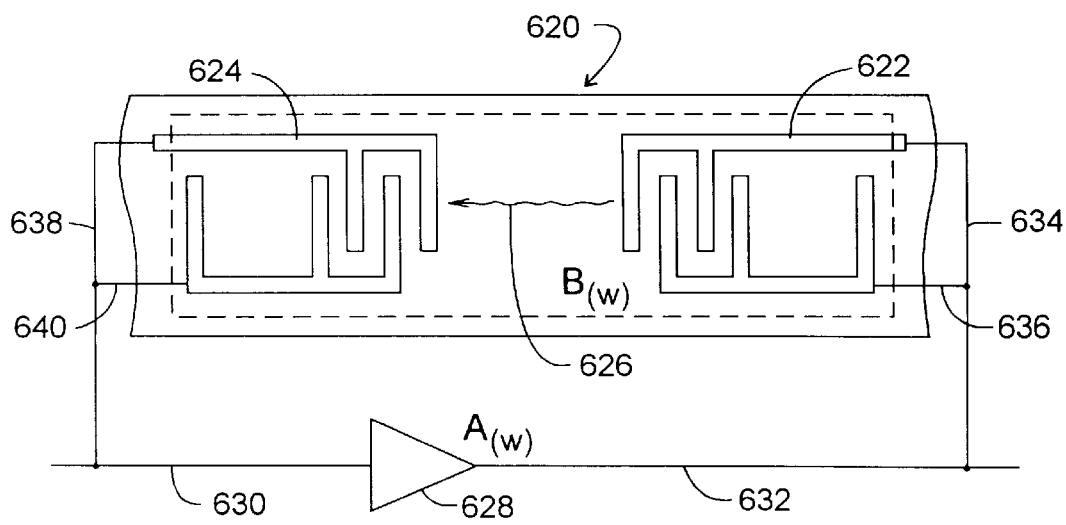
FIG. 30 is a schematic representation of an acoustic wave-based analyte concentration sensor.

Now considering analyte concentration sensors which are acoustic wave-based, reference is made to FIG. 30. In the figure, the concentration sensor forward assembly as it would be mounted in the manner of sensor 604 described in connection with FIGS. 27–29 is depicted schematically at 620. The sensing principle of such acoustic sensors is based upon the detection of changes of wave velocity and attenuation caused by perturbations at the surface of the material in which the wave propagates. If an acoustic wave delay line is placed in an oscillator loop as the frequency-determining element, velocity shift causes a shift in the delay time of the wave. This results in a shift of the oscillation frequency. In the figure, an interdigitated transmission transducer is shown at 622 spaced from a reception transducer 624. Sound reflectance from the analyte or analyte component being investigated is represented by the arrow 626. Transducers 622 and 624 are connected in a delay line oscillator circuit. The latter circuit includes an oscillator 628 having an input at line 630 and an output at line 632. Transducers 622 and 624 are incorporated within a feedback path or delay line, transducer 622 being coupled via lines 634 and 636 to line 632 and transducer 624 being coupled via lines 638 and 640 to line 630. Accordingly, the output of the amplifier 628 is fed back by the delay line incorporating the transducers where $A(\omega)$ represents amplifier gain and $B(\omega)$ represents delay line losses. The transducers as well as the oscillator circuit may be multi-layer devices constructed using conventional integrated circuit manufacturing methods employing a silicon (base), silicon dioxide, aluminum and zinc oxide (surface). See generally the following publications: Velekoop, et al., M. J., et al., "Integrated-Circuit-Compatible Design and Technology of Acoustic-Wave-Based Microsensors", Sensors and Actuators A., vol. 44, pp 249–263 (1994).

Figure 31:
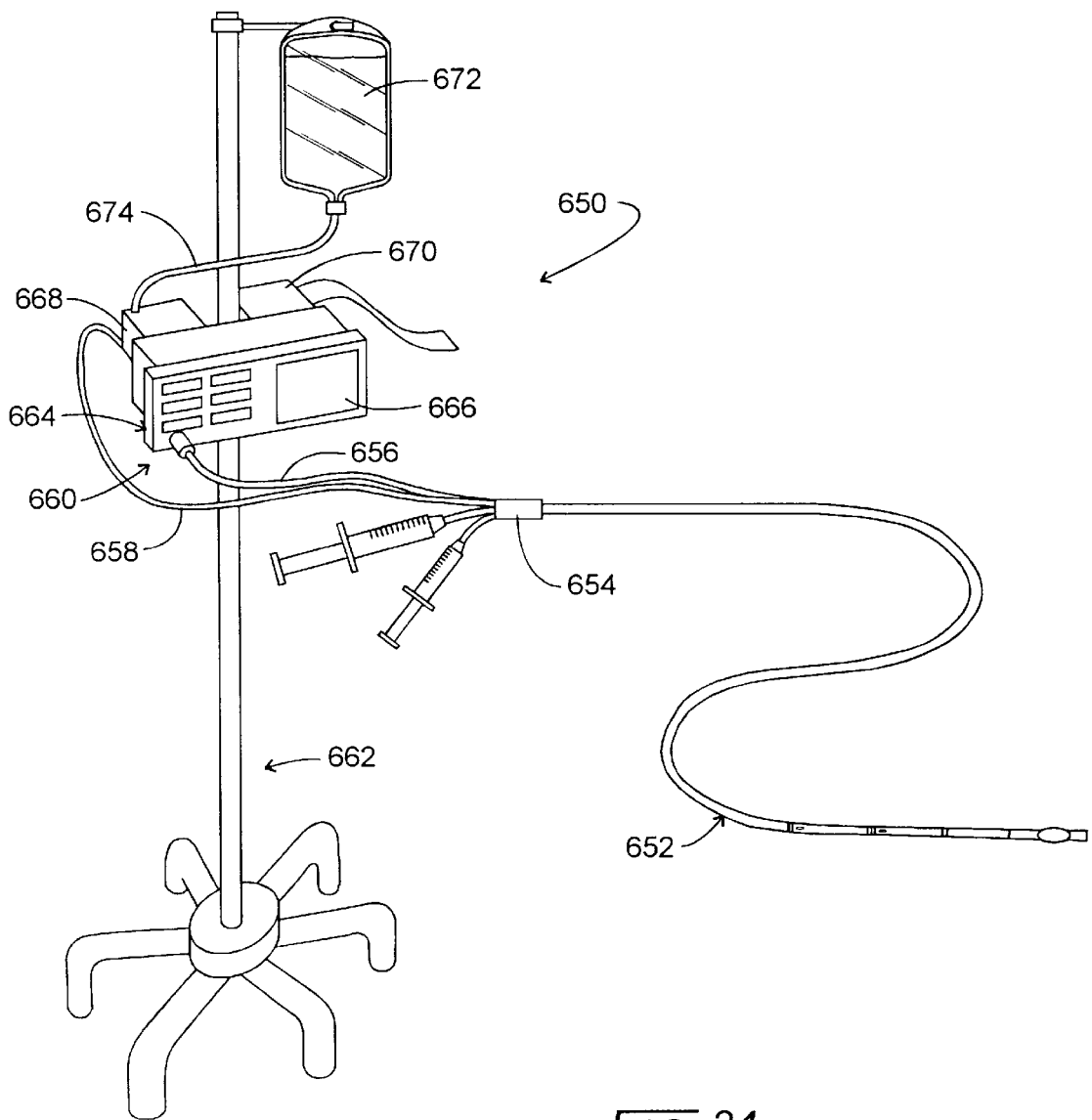
FIG. 31 is a pictorial representation of a system according to the invention.

Now considering the overall system for developing cardiac output measurement, reference is made to FIG. 31. In the figure, the system is shown in schematic pictorial fashion in general at 650 utilizing a pulmonary artery catheter as shown in general at 652. The implementation of this catheter is in correspondence with the pulmonary artery catheter described in connection with FIG. 1. At the input to the catheter, signal transfer output connections are shown to emanate from a module 654 and are directed as represented by multi-component cables 656 and 658 to operational coupling with a controller represented at 660. Controller 660 is mounted upon a conventional IV pole or stand represented generally at 662 and is seen to include an array of keys represented at 664 which are utilized for entering or inputting control parameters such as cardiac output or cardiac index limits, homeostatic threshold levels, and the like. A display 666 is provided adjacent the key array and an analyte-containing fluid pump 668 is mounted at the rear of the device along with a strip chart recorder 670. Analyte-containing fluid is supplied to the pump 668 from a disposable hanging bag source 672, and feed tube 674.

Figure 32:
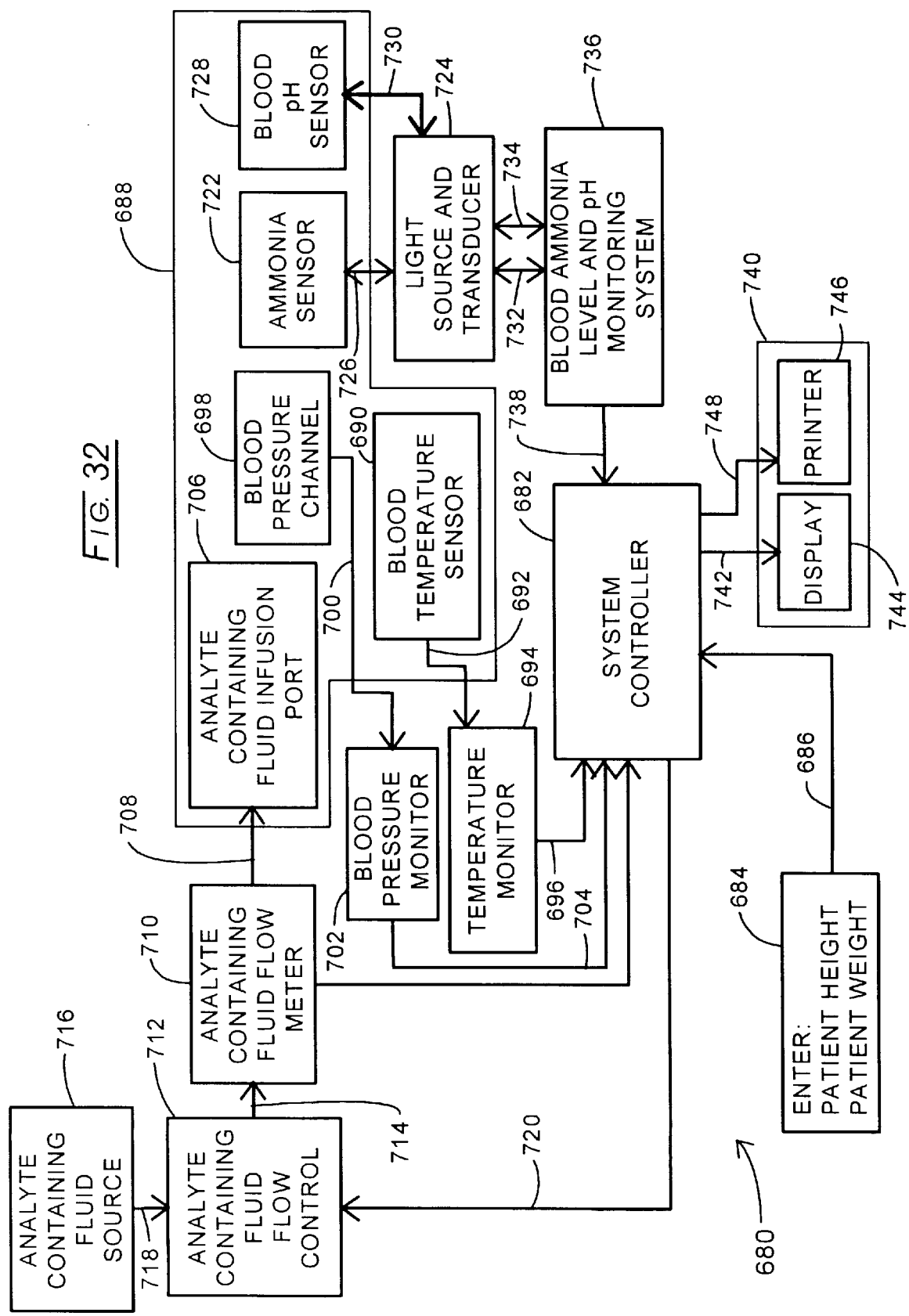
FIG. 32 is a block diagram of a control system configured according to the invention.

Referring to FIG. 32, a block diagram of the system within which the analyte-containing fluids and complementary sensors perform is represented. This system, as represented in general at 680 is operated in conjunction with a microprocessor-driven controller represented at block 682. The controller includes the conventional features for achieving control including read only memory (ROM), random access memory (RAM), as well as input/output components including programmable interface adapters which perform in conjunction with input devices such as a keyboard, and provide a display function which may include a printer. In the course of the use of system 680, a variety of parameters will be measured and entered into memory. For example, the patient's weight and height are entered as represented at block 684 and line 686. This information is utilized in deriving BSA, the body surface area, in meters$^2$ in order to ultimately compute cardiac index (CI) as described in conjunction with expression (2) above. The analyte component described in conjunction with FIG. 32 is ammonia gas ($NH_3$). For certain of the other analytes, it may be necessary to measure blood hematocrit and enter it on an intermittent basis or a continuous basis to provide a correction to achieve accurate cardiac output measurement. Two such analytes requiring this correction are carbon dioxide and ethanol.

The components of the catheter utilized are represented within a boundary 688. Such components include a blood temperature sensor such as described at 192 in FIG. 9 and represented at block 690. Data representing blood temperature is transmitted, as represented at line 692 to a temperature monitor represented at block 694 and the resultant data is inputted to the controller 682 as represented at line 696. Line 692 corresponds with earlier-described lines 228 and 230 (FIG. 11). Similarly, the blood pressure channel of the catheter is represented at block 698. The pressure output of die blood pressure channel is represented at line 700 as being directed to a blood pressure monitor function represented at block 702. This output from blood pressure monitor 702 is directed, as represented at line 704, to the system controller 682.

The infusion port or injectate outlet of the catheter within boundary 688 is represented at block 706. Analyte-containing fluid as represented at arrow 708 is introduced from an analyte-containing fluid flow meter represented at block 710. Input to the meter 710 is from an analyte-containing fluid flow control represented at block 712, the output of which is represented at line 714. Flow control 712 performs in conjunction with an analyte-containing fluid source represented at block 716 and line 718. Control over the fluid flow control function 712 is provided from the system controller 682 as represented at line 720. The control asserted from line 720 is one corresponding with the mass flow rate of injection of analyte-containing fluid represented as $m_I$ in expression (1) above.

The analyte component concentration sensor function within the catheter is represented at block 722. This sensor is represented as being operatively associated with a light source and transducer function represented at block 724 by a line 726. A blood pH sensor function within the catheter 688 is represented at block 728 as being associated through line 730 with the light source and transducer function at block 724. The output of the light source and transducer function 724 is represented by lines 732 and 734 as being operatively associated with a blood ammonia level and pH monitoring system represented at block 736. Outputs to the controller 682 from the monitoring system 736 are represented at line 738.

The measured value of blood pH is used in conjunction with the measured blood concentration of the analyte component, gaseous ammonia to compute the total ammoniacal concentration in the bloodstream at the measuring location. In particular, the analyte concentration sensor derives the measured concentration of ammonia gas in blood $Ca(NH_3)$. This measured value combined with the measured blood pH allows computation of the total ammoniacal concentration in blood, Ca, by applying the well known Henderson-Hasselbalch equation to the equilibriated ammonia gas ($NH_3$)-ammonium ion ($NH_4^+$) system. See generally in this regard: Hindfelt, D., "The Distribution of Ammonia Between Extracellular and Intracellular Compartments of the Rat Brain", Clinical Science and Molecular Medicine, vol. 48, pp 33–37, 1975. The relative distribution of ammonia gas ($NH_3$) and ammonium ion ($NH_4^+$) in solution is given by that Henderson-Hasselbalch equation as follows:

$$pH - pK_a = \log \frac{[C_a(NH_3)]}{[C_a(NH_4^+)]} \tag{3}$$

This equation can be restated in terms of the unknown, $C_a(NH_4^+)$ as follows:

$$Ca(NH_4^+) = C_a(NH_3)/[10 \exp (pH-pK_a)] \tag{4}$$

where
$Ca(NH_4^+)$ = concentration of ammonium ions ($NH_4^+$) in blood (micromole/liter)
$C_a(NH_3)$ = measured concentration of ammonia gas ($NH_3$) in blood (micromole/liter)
pH = measured blood pH pKa = pH level of solution above which all ammoniacal fluid exists as a gas ($NH_3$) where pKa=9.15 (Hindfelt, ibid).

The total ammoniacal content of the blood, $C_a$(total) can be calculated by controller 682 as follows:

$$C_a(\text{total}) = C_a(NH_3) + C_a(NH_4^+) \tag{5}$$

The values of total ammonia concentration of the blood, $C_a$(total) before and after the infusion of the analyte-containing fluid are then used in expression (1) to compute cardiac output (CO).

Parameters collected and derived by controller 682 are directed to the readout function represented by boundary 740. Function 740 includes two readouts including a dynamic display or screen as represented at line 742 and block 744. For permanent record purposes, as well as developing a cardiac output trendline with time, such information also is directed to a printer strip chart recorder represented at block 746 and line 748. Data which may be observed at display 744 include cardiac output (CO) displayed as computed in conjunction with expression (1) above; "baseline" ammoniacal concentration ($C_a$) prior to the commencement of an infusion interval. Next, cardiac index (CI) is displayed having been computed in conjunction with expression (2) above. Perceptible indications which may have an alarm status are published at the display and an audio signal also may be produced when the computed ammoniacal concentration represented by expression (5) exceeds an inputted homeostasis threshold value corresponding with an ammoniacal concentration in blood for iatrogenesis. Where desired, the analyte concentration developed with each measurement also may be published. Blood temperature data also may be published as a valuable parameter, the blood temperature measurement being carried out by, for example, temperature sensor 192 as described in connection with FIG. 9.

Figure 33A:
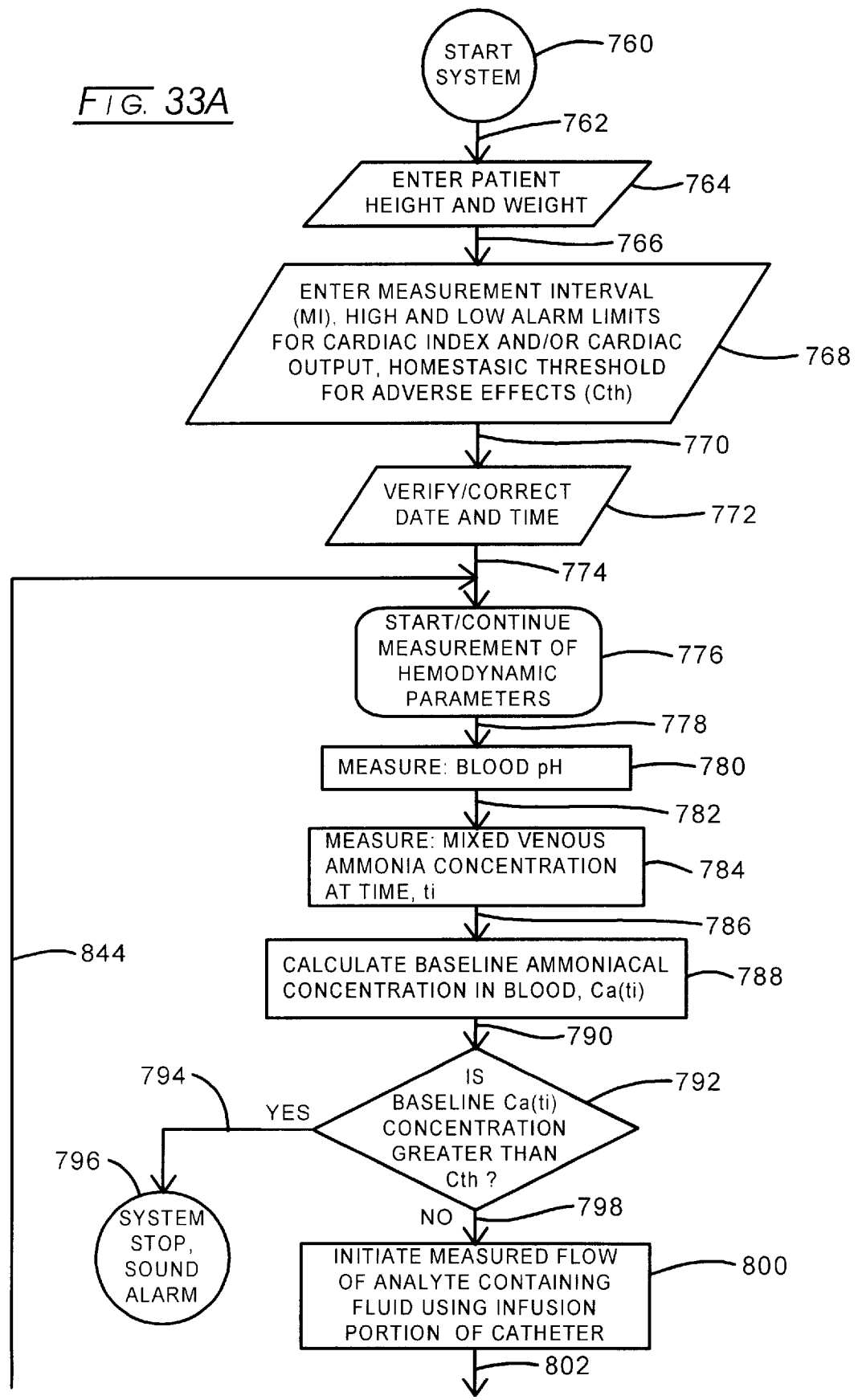
FIGS. 33A and 33B combine to show a flow chart describing the operation of a controller shown in FIG. 32.
Figure 33B:
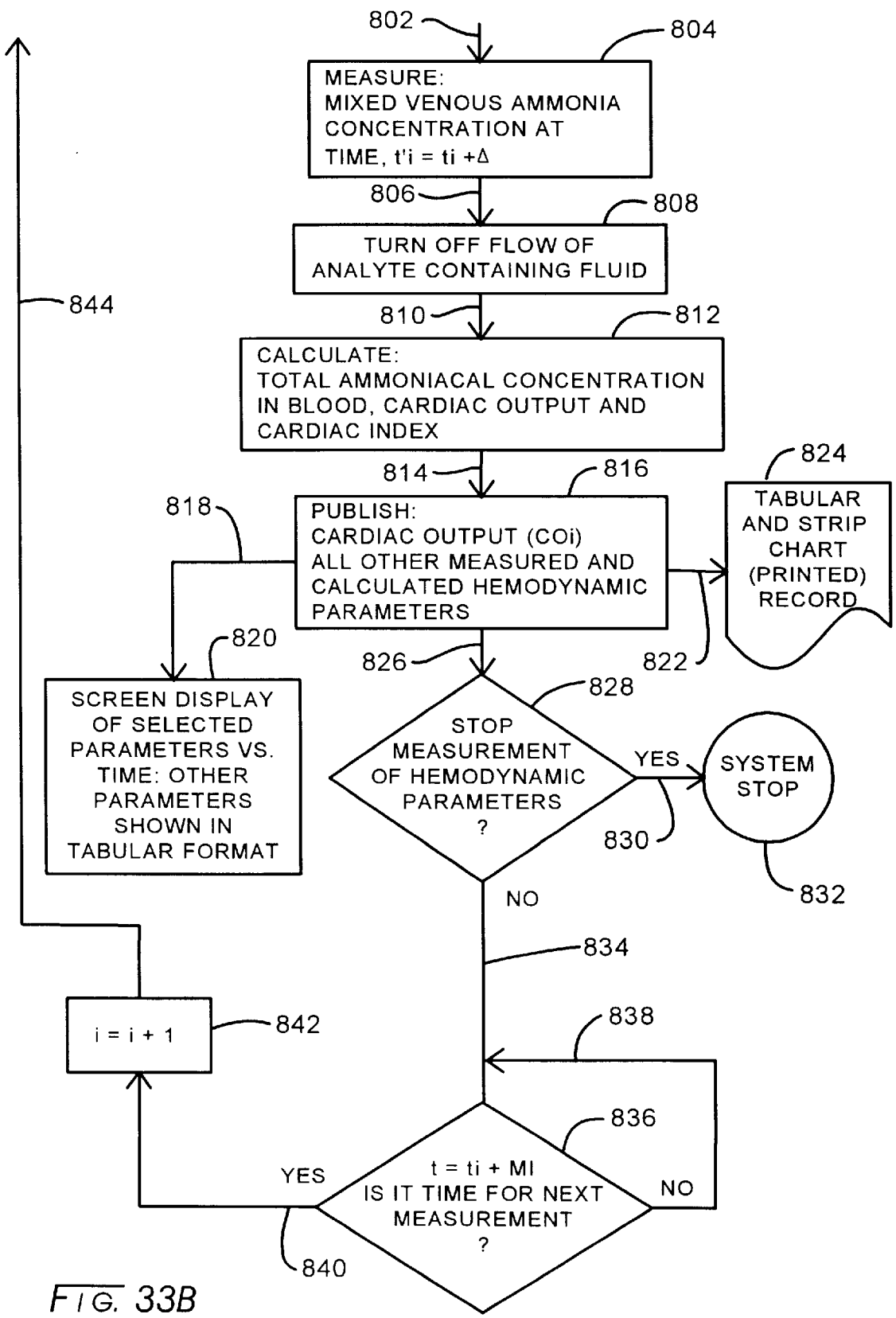

Referring to FIGS. 33A and 33B, a flow chart describing the operation of the system in conjunction with monitor-controller 682 is revealed. The system is started as represented at commencing node 760 and, as represented at line 762 and block 764, the patient height and weight is entered through the key array. As discussed in connection with block 684 in FIG. 32, this information is utilized for the purpose of computing cardiac index (CI) as set forth at expression (2). Next, as represented at line 766 and block 768, the operator elects an interval for carrying out successful measurement, that interval being designated, "MI". The above-described infusion interval is established in software by the manufacturer. The operator may select high and low alarm limits for cardiac index values, values falling below the lower limit indicating an inadequate cardiac output. Correspondingly, certain medical intervention may increase the cardiac index above a desired level, thus calling for an alarm condition. The limit, alternately, may be established for cardiac output values. However, the cardiac index is a normalized form evaluation which may be beneficial for this purpose. The operator also enters the noted homeostasis threshold value corresponding with ammoniacal fluid concentration for iatrogenesis or adverse effects ($C_{th}$). As discussed above, the metabolic system of the patient will gradually enter into the state of equilibrium or homeostasis with respect to the blood indicator or analye concentration in blood.

The program then continues as represented at line 770 and block 772, at which point the correct date and time are verified by the operator. This assures that data which is collected is correlated in time and date with manual records and manual interventions which may be carried out.

As represented at line 774 and block 776, the start or continuation of a sequence of measurements of hemodynamic parameters ensues. These parameters may have value in and of themselves or may be employed for the purpose of computing cardiac output and cardiac index. As noted earlier herein, a substantial number of additional parameters may be measured depending upon the type of concentration sensors employed and the number of sensors used. Fiberoptic-based sensor may serve such functions as additionally sensing blood oxygen levels and the like from which other parameters may be computed and displayed. Thus, in addition to the measurement of analyte concentration, pH, temperature and blood indicator or analyte concentration, other parameters may be developed based upon a supplementing blood oxygen measurement. Certain of these parameters are listed later herein in connection with a carbon dioxide analyte.

Blood pH is measured as represented by line 778 and block 780, and the baseline concentration of ammonia in blood is measured as represented at line 782 and block 784. At the commencement of the procedure, this will be carried out before the introduction of ammoniacal fluid injectate. Thereafter, the baseline values will be developed as described in conjunction with FIGS. 7 and 8. Then, as represented at line 786 and block 788, the controller calculates the baseline ammoniacal concentration in blood, $Ca(t_i)$. As represented at line 790, the program proceeds to the query posed at block 792 wherein a determination is made as to whether the baseline ammoniacal concentration in blood is greater than a threshold value, $C_{th}$. In the event that it is, then as represented at line 794 and node 796, the system is stopped and an alarm output is made.

Where the baseline concentration of analyte is not greater than the threshold value, then as represented at line 798 and block 800, a measured flow of analyte-containing fluid, i.e. ammoniacal fluid, is delivered utilizing the infusion outlet or port of the catheter.

The program continues as represented at line 802 which reappears in conjunction with FIG. 33B. Line 802 leads to the procedure represented at block 804 which provides for the measurement of mixed venous ammonia or ammonia in blood during the infusion interval at a time, $t'_i$, which is the earlier-noted $t_i$ plus a $\Delta$ interval of time. At the termination of the infusion interval, as represented at line 806 and block 808, the analyte-containing fluid flow is terminated. Then, as represented at line 810 and block 812, the controller calculates the ammoniacal concentration in blood, cardiac output, and cardiac index as described in conjunction with expressions (1)–(5).

The program then continues as represented at line 814 and block 816. At that block, the cardiac output and all other measured parameters are computed for publication. In this regard, as represented at line 818 and block 820, a screen display is made of selected parameters in conjunction with time and tabulations of parameters are made. Additionally, as represented at line 822 and symbol 824, a tabular and strip chart record can be provided.

The program then continues as represented at line 826 and block 828. At block 828, a determination is made as to whether the procedure should be terminated. In the event of an affirmative response to that inquiry, then as represented at line 830 and node 832, the system is stopped. In the event of a negative determination with respect to the query posed at block 828, then as represented at line 834 and block 836, a determination is made as to whether the time for a next measurement is at hand. If that interval, for example two or three minutes, has not expired, the program loops as represented at loop line 838. In the event that it is time for a next measurement, then as represented at line 840 and block 842, the index, i, is incremented by 1, and as represented at line 844, the program reverts to line 774 to commence the measurement procedure again.

In the course of carrying out pig experimentation with a pulmonary artery catheter utilizing ammoniacal fluid as the analyte-containing fluid, comparisons were carried out with respect to a standard represented as the cold bolus technique of thermal dilution. Pharmacological agents were utilized to raise and lower cardiac output of the pig and, in conventional practice, the cold bolus measurements were carried out four times and the last three measurements were averaged. On the other hand, utilizing the ammoniacal fluid injected, only one measurement was taken. Resulting cardiac output measurements over the interval of the experiment are plotted in FIG. 34. In the figure, the cold bolus average measurements are represented by dots and the measurements utilizing an ammoniacal fluid injectate are represented by triangles. A resulting curve is shown at 850 linking the thermodilution dots. Dashed curves 852 and 854, respectively, represent the upper bound of a 15% envelope and the lower bounds of such an envelope, such a range being commonly accepted as an appropriate accuracy range for any cold bolus thermodilution triplicate average measurements.

Figure 34:
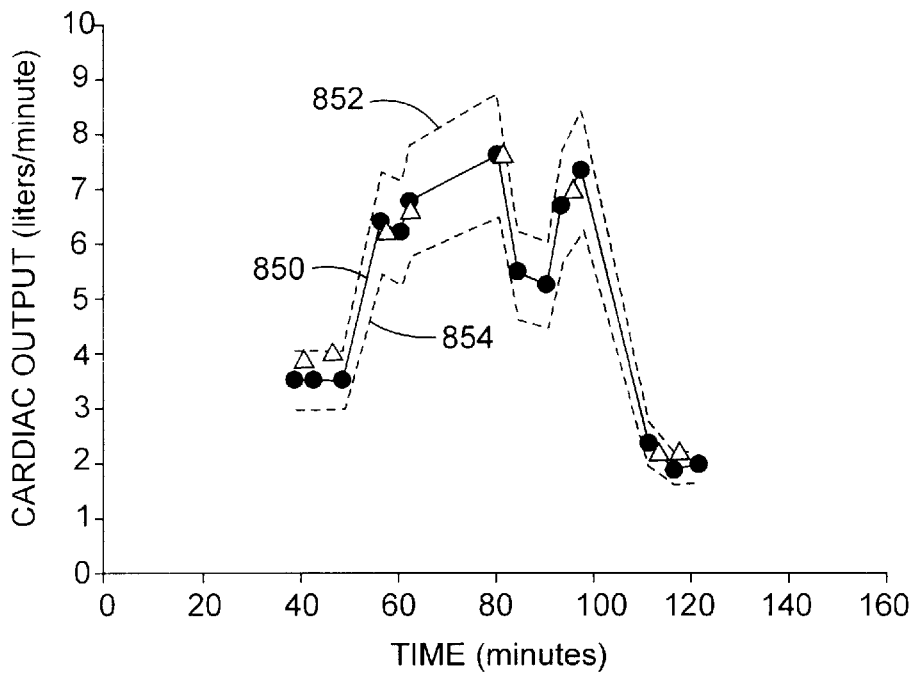
FIG. 34 is a graph showing cardiac output measurements performed on a pig in accordance with the invention and in accordance with a thermodilution method.
Figure 35:
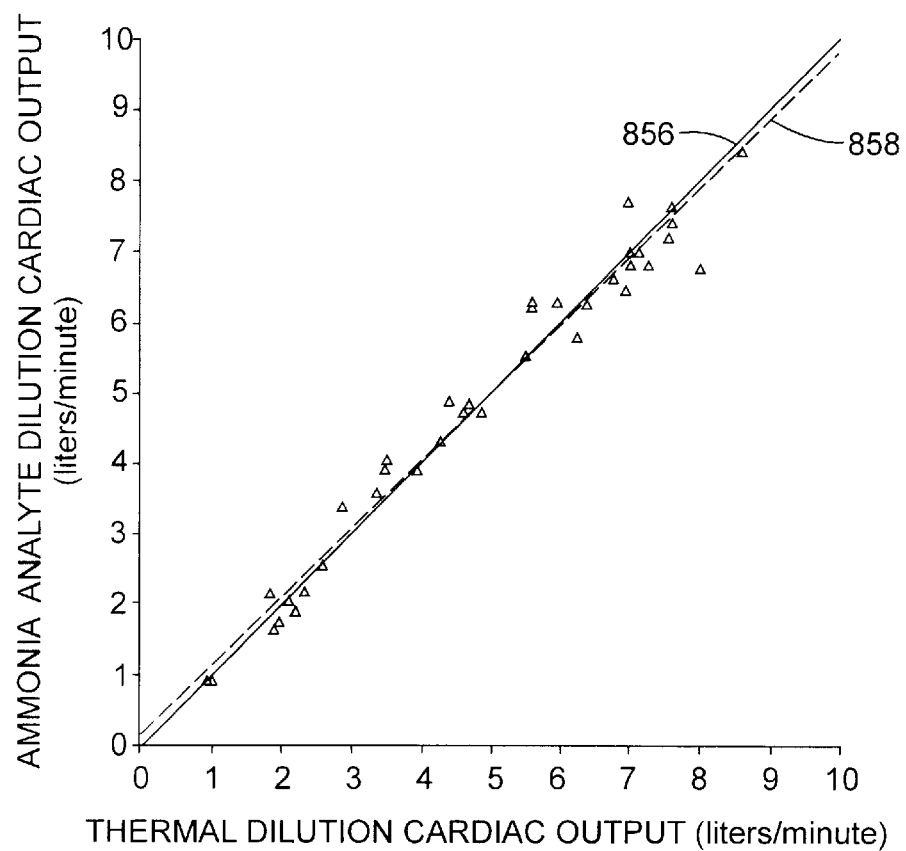
FIG. 35 is a scatter graph compiling data collected in conjunction with the experiment of FIG. 34.

FIG. 35 is a scatter graph configured utilizing the data developed in conjunction with FIG. 34. In the scatter graph, the ordinant represents an ammoniacal fluid-based measurement and the abscissa represents the corresponding averaged thermodilution measurement. Perfect correspondance is represented by the 45° curve 856. A plot of the averaging of the data is represented by the dashed curve 858.

As noted earlier herein, a carbon dioxide releasing fluid may be employed as an analyte-containing fluid. When so employed, the concentration of the carbon dioxide analyte is measured by the analyte sensor. While the corresponding concentration carbonates or the like may be measured, the former analyte component lends itself more readily to concentration analysis. Accordingly, where carbon dioxide releasing fluid is employed as the injectate, then cardiac output (CO) is computed in accordance with the following expression:

$$CO = \frac{K * \dot{m}CO_2}{10 * [C\bar{v}CO_2'(t'_i) - C\bar{v}C)_2(t_i)]} \tag{6}$$

where CO is cardiac output in liters per minute; K is a constant; $\dot{m}CO_2$ is the rate of injection of carbon dioxide in grams per second; $C\bar{v}CO_2(t_i)'$ is mixed venous carbon dioxide releasing fluid concentration in milliliters of such fluid per decaliter of blood at a baseline defining time, $t_i$ and $C\bar{v}CO_2(t'_i)$ is the corresponding mixed venous carbon dioxide releasing fluid concentration at subsequent time, $t'_i$, during the infusion interval.

To derive cardiac output (CO) in accordance with expression (6), the system requires the measurement of the following five parameters:

(a) $P_{plasma}CO_2$, the partial pressure of carbon dioxide in the plasma measured utilizing an indwelling $CO_2$ sensor;

(b) the pH of blood in the bloodstream is measured using an indwelling pH sensor preferably in the vicinity of the measurement made at (a);

(c) the temperature of blood, T, within the bloodstream will be measured using a temperature sensor mounted on the catheter employed.

(d) hematocrit (Hct) which may be used to calculate hemoglobin (Hgb); and (e) $S\bar{v}O_2$, the mixed venous oxygen saturation of the blood in the bloodstream, as probably measured using an indwelling catheter oximeter or calculated from knowledge of above parameters.

In the process of deriving cardiac output (CO) in accordance with expression (6), the controller carries out solution of supporting expressions. In this regard, the concentration of carbon dioxide in plasma is computed in accordance with the following expression:

$$C_{plasma}CO_2 = 2.226 * s * P_{plasma}CO_2 * [1 + 10^{pH-pK}], \quad (7)$$

where pH is the pH value of the blood.

The term, pK is coupled in accordance with the following expression:

$$pK' = 6.086 + [0.042*(7.4-pH)] + [(38-T)*[0.00472 + [0.00139*(7.4-pH)]]] \quad (8)$$

where T is the temperature of the blood.

The term s, is computed as follows:L $$s = 0.0307 + [0.007*(37-T)] + [0.00002*(37-T)^2] \quad (9)$$

The controller derives a value for mixed venous carbon dioxide content, $CvCO_2$ in accordance with the following expression:

$$C\bar{v}CO_2 = [C_{plasma}CO_2]*[1 - 0.0899*Hgb[3.352 - 0.456*S\bar{v}O_2)*(8.142 - pH)] \quad (10)$$

where Hgb is hemoglobin level and $S\bar{v}O_2$ is a value corresponding with mixed venous oxygen saturation output.

Where carbon dioxide is selected as the analyte, the system may derive a variety of parameters as are listed below. These parameters also may be developed or utilized with other analytes:

| | | |
|---|---|---|
| CO | = measured cardiac output in liters/minute | |
| BSA | = body surface area in $m^2$ (calculated based on patient's height and weight) | |
| pH | = measured blood pH | |
| CI | = cardiac index = CO/BSA (liters/minute $m^2$) | |
| T | = measured patient temperature in °C. | |
| $SvO_2$ | = measured mixed venous oxygen saturation in % | |
| $SaO_2$ | = measured oxygen saturation in arterial plasma in % | |
| $PaO_2$ | = dissolved oxygen in arterial plasma (mm Hg) | |
| | = 10 exp [log $P_{50}$ + (log $(SaO_2/(1 - SaO_2)))/2.7$] | (11) |
| | = where $P_{50}$ = 27 mmHg based on normal oxygen dissociation curve | |
| $P\bar{v}O_2$ | = dissolved oxygen in mixed venous plasma (mmHg) | |
| | = 10 exp [log $P_{50}$ + (log $(S\bar{v}O_2/(1 - S\bar{v}O_2))$)2.7] | (12) |
| α | = solubility coefficient of oxygen (ml[$O_2$]/dl [blood] * mmHg) | |
| | = 0.0031/[(10 exp (0.024 * (38.0 - T))) * (10 exp (-0.50(7.40 - pH)))] | (13) |
| Hct | = measured blood hematocrit in percent | |
| DysHgb | = measured blood dyshemoglobin concentration in gm/dl | |
| Hgb | = 0.3718 (Hct) - 1.30 - DysHgb (gm/dl) | (14) |
| $CaO_2$ | = arterial oxygen content (ml[$O_2$]/dl [blood]) | |
| | = [Hgb * 1.34 * $SaO_2$] + [$PaO_2$ * α] where 1.34 has units of ml[$O_2$]/gm[Hgb] | (15) |
| | = oxygen transport (ml/min) | |
| $DO_2$ | = $CaO_2$ * CO * 10 | (16) |
| MAP | = measured mean arterial pressure in mmHg | |
| MPAP | = measured mean pulmonary arterial pressure in in mmHg | |
| CVP | = measured central venous pressure in mmHg | |
| WP | = measured wedge pressure in mmHg | |
| HR | = measured heart rate in beats/minute | |

-continued

| | | |
|---|---|---|
| SVRI | = systemic vascular resistance index [(mnHg * $m^2$)/(l/min)] | |
| | = (MAP - CVP)/CI | (17) |
| PVRI | = pulmonary vascular resistance index [(minHg * $m^2$)/(l/min)] | |
| | = (MPAP - WP)/CI | (18) |
| SI | = stroke index (ml/beat/$m^2$) | |
| | = CI/(HR * 1000) | (19) |
| LVSWI | = left ventricular stroke work index (gm · m/$m^2$) | |
| | = (MAP - WP) * SI * 0.0136 | (20) |
| RVSWI | = right ventricular stroke work index (gm · m/$m^2$) | |
| | (MPAP - CVP) * SI * 0.0136 | (21) |

Other analyte or analyte component sensors may be provided as follows:

A glucose sensor may be constructed using well-known enzyme-based methods (e,g., involving glucose oxidase in conjunction with an oxygen senso). In such a devices, an immobilized biological/biochemical component interacts with the analyte to produce, via an appropriate transducer, a signal proportional to the quantity or activity of analyte. The recognition interaction may entail either a binding process (e.g. for antibodies) or a biochemical reaction (e.g. enzyme catalysis). Transduction can be achieved by any of several detection approaches: optical (e.g. absorbance, fluorescence, chemiluminescence and bioluminescence, mass measurement (e.g. piezoelectric and surface acoustic wave), heat and electromechanical-based measurement. By way of example, the sensor may be constructed based on the principles first described by Clark and Lyons (Clark, L. C. and Lyons, C., "Electrode System for Continuous Monitoring in Cardiovascular Surgery," Ann. N.Y. Acad. Science, Vol. 102, p. 29ff [1962]). The concentration of glucose in the blood is achieved by means of a dissolved oxygen ($pO_2$) sensor used in conjunction with the glucose oxidase-catalyzed reaction:

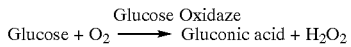

$$\text{Glucose} + O_2 \xrightarrow{\text{Glucose Oxidaze}} \text{Gluconic acid} + H_2O_2$$

The rate of decrease in $pO_2$ can be used as a measure of the glucose concentration.

Yet another approach involves the use of an amperometric glucose electrode which uses a ferrocene derivative as the mediator. In this sensor, dimethyl ferrocene is incorporated into a graphite electrode to which glucose oxidase is immobilized. During operation, the glucose oxidase that is reduced in the enzymatic reaction is reoxidized by electrogenerated ferricinium ions. The current flowing in this regeneration process is proportional to the glucose concentration. (See Cass, A. E. G., et al., "Ferrocene-Mediated Enzyme Electrode for Amperometric Determination of Glucose," Anal. Chem., Vol. 56, p 667ff [1984]. With the use of an appropriate membrane (e.g. polyurethane), glucose may be measured at concentrations up to 50 mmol/liter.

One preferred approach for measuring heparin level in blood involves the use of an ion-selective electrode in conjunction with a polymer membrane (e.g., polyvinyl chloride) doped with tridodecylmethylammonium chloride as the heparin complexing agent. The measured potential between a reference electrode and the heparin-selective electrode is correlatable with the concentration of heparin in the blood. In this regard, see Yang, V., et al., "A Novel Electrochemical Heparin Sensor," ASAIO Journal, Vol. 39, No., 3, pp M195–M201 (1993).

An ethanol sensor may be constructed based on principles similar to those described for glucose sensors. Hydrogen peroxide is a product of the enzymatic oxidation of glucose or alcohol. Hence, an electrode responsive to hydrogen peroxide can be used to quantitate the concentration of the analyte of interest. A peroxide electrode that is covered by an enzyme membrane can be used to detect ethanol concentration in the blood using an oxygen oxido-reductase enzyme appropriate for ethanol (e.g. alcohol oxidase). The analyte diffuses to the enzyme layer where it is dehydrogenated, thereby producing hydrogen peroxide. The hydrogen peroxide diffuses to the anode and causes a current proportional to the rate of hydrogen peroxide formation. In this regard, see Clark, L. C., "A Family of Polarographic Enzyme Electrodes and the Measurement of Alcohol," Biotechnology Bioengineering, Vol. 3, p 337ff (1972).

Since certain changes may be made in the above-described system, apparatus, and method, without departing from the scope of the invention herein involved, it is intended that all matter contained in the above description or shown in the accompanying drawings shall be interpreted as illustrative and not in a limiting sense.

We claim:

1. Apparatus for determining the cardiac output of the cardiovascular system of the body of a patient, comprising:
   a catheter, having an externally disposed proximal end region and an oppositely disposed measurement region position able within the bloodstream of the body;
   an indicator channel within said catheter having a fluid input at said proximal end region connected with a controlled source of analyte containing fluid biocompatible with and metabolizable within said body and selected from the group consisting of: ammoniacal fluid, heparin, ethanol, a carbon dioxide releasing fluid, glucose, anesthesia agent, and excluding oxygen, said indicator dilution channel extending to an infusion outlet at said measurement region from which said analyte containing fluid may be expressed; and
   an analyte concentration sensor, responsive to said analyte, having a forward assembly configured for flowing blood contact mounted with said catheter at said measurement region at a location spaced downstream from said infusion outlet when positioned within said bloodstream and having an analyte sensor or concentration sensor output transmissible to said proximal end region corresponding with a concentration level of said analyte within said bloodstream which is correlatable with said cardiac output.

2. The apparatus of claim 1 in which:
   said analyte concentration sensor forward assembly comprises an analyte concentration reactor having an output condition in response to the concentration of said analyte; and
   a membrane covering said reactor impermeable to blood and permeable to said analyte having an outer surface contactable with said flowing blood; and
   said analyte concentration sensor includes:
      a transmission assembly for conveying a signal corresponding with said output condition to said catheter proximal end region as said analyte output.

3. The apparatus of claim 2 including:
   a sensor channel within said catheter extending from said proximal end region to said analyte concentration sensor forward assembly;
   a pH sensor mounted with said catheter at a location for positioning within the bloodstream of said body and wherein;
   said analyte-containing fluid is ammoniacal fluid;

said membrane is permeable to gaseous ammonia ($NH_3$);
said reactor is a gaseous ammonia sensitive dye; and
said transmission assembly is a fiber optic colorimetric measurement assembly which quantitates a change in color of the dye and is mounted within said sensor channel.

4. The apparatus of claim 2 in which:
said analyte containing fluid is an ammonium compound;
said membrane is permeable to ammonium ion ($NH_4^+$);
said reactor comprises first and second electrodes immersed within an electrolyte sensitive to said ammonium ion; and
said transmission component comprises a potentiometric assembly coupled with said first and second electrodes.

5. The apparatus of claim 2 in which:
said analyte containing fluid is an ammonium compound;
said membrane is permeable to ammonium ion ($NH_4^+$);
said reactor comprises first and second electrodes immersed within an electrolyte sensitive to said ammonium ion; and
said transmission component comprises an amperometric assembly coupled with said first and second electrodes.

6. The apparatus of claim 2 including:
a sensor channel within said catheter extending from said proximal end region to said analyte concentration sensor forward assembly;
said reactor comprises an analyte-sensitive fluorescent material having a fluorescence intensity as said output condition;
said transmission component is a fiber optic assembly for stimulating said reactor and conveying said fluorescence intensity as said output condition.

7. The apparatus of claim 2 including:
a sensor channel within said catheter extending to said analyte concentration sensor forward assembly;
said reactor comprises an analyte-sensitive fluorescent material stimulatable into fluorescence, the rate of quenching of said fluorescence being said output condition; and
said transmission component is a fiber optic assembly for stimulating said reactor and conveying resultant generated light.

8. The apparatus of claim 2 in which said analyte concentration reactor is configured as a Schottky diode array having a conductive polymer responsive to said analyte to effect a forward bias alteration as said analyte sensor output.

9. The apparatus of claim 1 including:
a sensor channel within said catheter extending to said analyte concentration sensor forward assembly;
a pH sensor mounted with said catheter at a location for positioning within the bloodstream of the body;
said analyte is ammonia;
said concentration sensor is a fiber optic assembly within said indicator sensor channel having as said forward assembly a tip adapted for direct light exchange communication with the bloodstream of the body, said fiber optic assembly being extensible to a light source and photoresponsive assembly for measuring the concentration of ammonia gas ($NH_3$) in the bloodstream.

10. The apparatus of claim 1 including:
a sensor channel within said catheter extending to said analyte concentration sensor forward assembly;
said analyte is ammonium ion ($NH_4^+$);

said analyte concentration sensor is an electrode pair immersed in an electrolyte which is ammonium ion sensitive for measuring the concentration of ammonium in the bloodstream.

11. The apparatus of claim 1 in which said analyte concentration sensor comprises:

a fiberoptic assembly extending from said catheter proximal end region to a fiberoptic tip located at and forming a component of said forward assembly;

a membrane forming a component of said forward assembly, impermeable to blood and permeable to said analyte, having an outer surface contactable with said flowing blood and an inner surface spaced from said fiberoptic tip to define an analyte equilibration cavity; and including a light transmission and reception assembly optically coupled with said fiberoptic assembly at said proximal end region and actuable to derive said analyte sensor output with respect to analyte at said equilibriation cavity.

12. The apparatus of claim 11, in which said membrane inner surface is light reflecting.

13. The apparatus of claim 1 in which said analyte concentration sensor comprises:

a fiberoptic assembly extending from said catheter proximal region to a fiberoptic tip at said forward assembly, including an outer surface extending inwardly from said fiberoptic tip;

an end plug impervious to blood having an inwardly disposed surface spaced from said fiberoptic tip to define the length of an equilibriation cavity;

a membrane impermeable to blood and permeable to said analyte, having an outer surface contactable with said flowing blood, said membrane extending sealingly about said outer surface and said end plug to define the sides of said equilibration cavity.

14. The apparatus of claim 1 in which said analyte concentration sensor comprises:

a fiberoptic assembly extending from said catheter proximal end region to said forward assembly and having a forward light transmission leg and a return transmission leg spaced from said forward light transmission leg to define a gap situated at said outer assembly; and a membrane impermeable to blood and permeable to said analyte, having an outer surface contactable with said flowing blood, said membrane sealingly extending about said gap to define an equilibration cavity.

15. The apparatus of claim 1 in which said analyte concentration sensor forward assembly is configured as a Schottky diode array having a conductive polymer responsive to said analyte to effect a forward bias alteration as said analyte output.

16. The apparatus of claim 1 in which said analyte concentration sensor forward assembly comprises an acoustic-wave sensor having an acoustic wave delay line within an oscillator loop to derive said analyte output as a frequency shift.

17. The apparatus of claim 1 including:

a temperature sensor mounted upon said catheter in the vicinity of said analyte concentration sensor and having a temperature value output at said proximal end region corresponding with the temperature of blood within said bloodstream;

an auxiliary port within said catheter in the vicinity of said infusion outlet; and an auxiliary channel within said catheter extending in fluid transfer communication from said auxiliary port to said proximal end region for delivering fluid through said auxiliary port.

18. A system for determining the cardiac output of the cardiovascular system of the body of a patient, comprising:

a source of analyte-containing fluid biocompatible with and metabolizable within said body and having a predetermined indicator concentration, said analyte being independent of the thermal energy content of said fluid;

fluid flow control apparatus coupled with said source of analyte-containing fluid and controllable to provide a flow of said analyte-containing fluid at a mass flow rate for an infusion interval at a fluid output;

a catheter having an externally disposed proximal end region and an oppositely disposed measurement region positionable within the bloodstream of said body;

an indicator channel within said catheter having a fluid input at said proximal end region connected in fluid transmission relationship with said fluid flow control apparatus fluid output and extending to an infusion outlet at said measurement region from which said analyte-containing fluid may be expressed into the bloodstream of said body;

an analyte concentration sensor, responsive to analyte within said bloodstream to provide a concentration sensor output, having a forward assembly contactable with flowing blood mounted with said catheter at said measurement region at a location spaced from said infusion outlet a dilution measurement distance downstream when positioned within said bloodstream and having a capability for providing said concentration sensor output with a rapidity effective to derive a cardiac output measurement as often as about every one to three minutes and in conjunction with said infusion interval substantially less than said measurement frequency interval;

a controller for controlling said fluid flow control apparatus and said analyte concentration sensor and responsive to each said concentration sensor output for deriving the value of the analyte concentration level within said bloodstream adjacent said forward assembly, responsive to effect control of said analyte concentration sensor to derive a baseline analyte concentration level output, then responsive to effect said flow of said analyte-containing fluid at a predetermined mass flow rate for said infusion interval and for simultaneously controlling said sensor during said infusion interval to derive a subsequent analyte concentration level output, responsive to correlate said baseline analyte concentration level output, said subsequent value for analyte concentration level output, and said predetermined mass flow rate to derive a first output signal representing a value corresponding with cardiac output; and a display responsive to said first output signal for providing a perceptible output corresponding therewith.

19. The system of claim 18 in which said controller is responsive to a sequence of said baseline analyte concentration level outputs to derive a comparison analyte concentration level in blood corresponding with metabolic homeostasis of said body, and responsive to compare an inputted homeostasis threshold value corresponding with analyte concentration in blood for iatrogenesis with said comparison analyte concentration level in blood to derive a second output signal when said comparison analyte concentration level in blood represents a value greater than said inputted homeostasis threshold value.

20. The system of claim 18 in which said controller controls said fluid flow control apparatus to provide said infusion interval of about two to thirty seconds.

21. The system of claim 18 including:
a pH sensor mounted with said catheter at a location for positioning within the bloodstream of said body and controllable to provide a pH sensor output corresponding with the pH value of blood with which it is in contact;
said controller effects control of said pH sensor to derive said pH sensor output and is responsive to correlate said pH sensor output, said baseline analyte concentration level output, said subsequent analyte concentration level output, and said predetermined mass flow rate to derive said first output signal.

22. The system of claim 21 in which:
said analyte-containing fluid analyte is an ammoniacal fluid;
said analyte concentration sensor output is provided in correspondence with the concentration of ammonia gas ($NH_3$) in said bloodstream; and
said controller derives a total ammoniacal concentration in blood in correspondence with the expressions:

$Ca(NH_4^+)=Ca(NH_3)/[10\ exp\ (pH-pKa)]$ $Ca=Ca(NH_3)+Ca(NH_4^+)$ where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists only as a gas, and Ca is the total ammoniacal concentration in blood.

23. The system of claim 22 in which said controller derives said first output signal in correspondence with the expression:

$$CO(t_i) = \frac{K*m_I*[IC_a - C_a(t'_I)]}{[C_a(t'_I) - C_a(t_i)]}$$

where, $CO(t_i)$ is cardiac output measured at time $(t_i)$, K is a constant, $m_I$ is the said mass flow rate of ammoniacal fluid for said infusion interval, ICa is the total ammoniacal concentration of the analyte-containing fluid, $Ca(t'_i)$ is the total ammoniacal concentration of the analyte-containing fluid in blood based upon said subsequent level analyte concentration level output measured during said infusion interval, and $Ca(t_i)$ is the total ammoniacal concentration in blood based upon said baseline analyte concentration level output.

24. The system of claim 22 in which said analyte concentration sensor is configured to derive said concentration sensor output by optical colorimetry.

25. The system of claim 22 in which said analyte concentration sensor is configured to derive said concentration sensor output as an amperometry signal.

26. The system of claim 22 in which said analyte concentration sensor is configured to derive said concentration output as a potentiometric signal.

27. The system of claim 22 in which said analyte concentration sensor is configured to derive said concentration sensor output employing optical fluorescence.

28. The system of claim 21 in which:
said analyte is carbon dioxide; and
said analyte concentration sensor output is provided in correspondence with the concentration of carbon dioxide in said bloodstream.

29. The system of claim 18 in which said controller is responsive to inputted values representing the height and weight of said body to derive a value for body surface area, and is responsive to a derived value of cardiac output and said value for body surface area to derive an output signal representing a value of cardiac index; and
said display is responsive to said output signal for displaying said derived value representing cardiac index.

30. The system of claim 29, in which said controller is responsive to an inputted lower threshold limit for cardiac index retained in memory and to said derived value of cardiac index to derive a third output signal when said derived value of cardiac index is below said threshold limit value for cardiac index; and
said display is responsive to said third output signal for displaying alarm information with respect to said derived value of cardiac index.

31. The system of claim 29, in which said controller is responsive to an inputted upper limit value for cardiac index retained in memory and to said derived value of cardiac index to derive a fourth output signal when said derived value of cardiac index is above said upper limit value for cardiac index; and
said display is responsive to said fourth output signal for displaying alarm information with respect to said derived value of cardiac index.

32. The system of claim 18 in which:
said controller is responsive to derive a fifth output signal corresponding with the most recently derived analyte concentration level in blood; and
said display is responsive to said fifth output signal for displaying said analyte concentration level in blood.

33. The system of claim 18 in which said source of analyte-containing fluid is selected from the group consisting of ammoniacal fluid, heparin, ethanol, carbon dioxide releasing fluid, glucose, anesthesia agent, and excluding oxygen.

34. The system of claim 18 including:
a pH sensor mounted with said catheter at a location for positioning within the bloodstream of said body and controllable to provide a pH sensor output corresponding with the pH value of the blood;
a blood oxygen saturation sensor mounted with said catheter at a location for positioning within the bloodstream of said body and controllable to provide a mixed venous oxygen saturation output;
a temperature sensor mounted upon said catheter in the vicinity of said analyte concentration sensor and having a temperature value output at said proximal end region corresponding with the temperature of blood within said bloodstream;
said analyte-containing fluid is a carbon dioxide releasing fluid;
said analyte is carbon dioxide; and
said controller effects control of said pH sensor to derive said pH sensor output, effects control of said blood oxygen sensor to derive said mixed venous oxygen saturation output, effects control of said temperature sensor to derive said temperature value output, and is responsive to correlate said pH sensor output, said mixed venous oxygen saturation output, said temperature value output, said baseline analyte concentration level output, an inputted value corresponding with hemoglobin level, and said subsequent analyte concentration level output to derive said first output signal.

35. The system of claim 34 in which:

said concentration sensor output corresponds with the partial pressure of carbon dioxide in plasma ($P_{plasma}CO_2$);

said controller derives the concentration of carbon dioxide in plasma ($C_{plasma}CO_2$) in accordance with the expression:

$$C_{plasma}\ CO_2 = 2.226 * s * P_{plasma}\ CO_2 * [1 + 10^{pH-pK}],$$

where pH is said pH value of the blood;

said controller derives the value, pK' in accordance with the expression:

$$pK' = 6.086 + [0.042*(7.4-pH)] + [(38-T)*[0.00472 + [0.00139*(7.4-pH)]]],$$

where:

T is said temperature of the blood; and said controller derives the value, s, in accordance with the following expression:

$$s = 0.0307 + [0.00057*(37-T)] + [0.00002*(37-T)^2].$$

36. The system of claim 35 in which:

said controller derives a value for mixed venous carbon dioxide content, $\bar{CvCO_2}$, in accordance with the expression:

$$\bar{CvCO_2} = [C_{plasma}\ CO_2]*[1 - 0.0289*Hgb/[(3.352 - 0.456*S\bar{v}O_2)*(8.142-pH)]],$$

where Hgb is said hemoglobin level, and $\bar{SvO_2}$ is a value corresponding with said mixed venous oxygen saturation output.

37. The system of claim 36 in which:

said controller derives said value for cardiac output, CO, in accordance with the expression:

$$CO(t_i) = \frac{K * \dot{m}CO_2}{10 * [\bar{CvCO_2}(t'_i) - \bar{CvCO_2}(t_i)]}$$

where ($CO(t_i)$) is cardiac output measured at time ($t_i$), K is a constant, $\dot{m}\ CO_2$ is said mass flow rate of carbon dioxide within said carbon dioxide releasing fluid, $\bar{CvCO_2}(t'_i)$ is mixed venous carbon dioxide content of blood corresponding with said subsequent analyte concentration level output measured during said infusion interval, and $\bar{CvCO_2}(t_i)$ is mixed venous carbon dioxide content of blood corresponding with said baseline analyte concentration level output.

38. The method for determining the cardiac output of the cardiovascular system of the body of a patient, comprising the steps of:

(a) providing a catheter having a proximal end region and extending to a measurement region, an indicator channel within said catheter having a fluid input at said proximal end region and extending to an infusion outlet at said measurement region from which analyte-containing fluid may be expressed, an analyte concentration sensor mounted with said catheter having a forward assembly contactable with flowing blood at said measurement region at a location spaced from said infusion outlet a dilution measurement distance, responsive to the presence of an analyte to provide an output corresponding with the concentration of analyte in blood and having a capability for providing said output within an infusion interval achieving a cardiac output measurement frequency interval of about one to three minutes;

(b) positioning said catheter within the bloodstream of said body, locating said measurement region at the heart region of the patient in a cardiac output measurement orientation wherein said analyte concentration sensor is downstream within said bloodstream from said infusion outlet;

(c) providing a source of analyte-containing fluid biocompatible with and metabolizable within said body and having a predetermined indicator concentration, said analyte being independent of the thermal energy content of said fluid;

(d) deriving a baseline value corresponding with the concentration of said analyte in said bloodstream from said concentration sensor output;

(e) delivering said analyte-containing fluid from said source into said indicator channel input at a predetermined mass flow rate for said infusion interval;

(f) deriving a subsequent value corresponding with the concentration of said analyte in said bloodstream from said concentration sensor concentration output during said infusion interval; and (g) deriving a value for the cardiac output of the heart of the body by correlating said baseline value, said subsequent value, said indicator concentration, and said predetermined mass flow rate.

39. The method of claim 38 in which said steps (d) through (f) are carried out within a measurement interval frequency of about one to three minutes.

40. The method of claim 38 including the steps of:

(h) selecting a homeostasis threshold value corresponding with an analyte concentration level in blood for iatrogenesis;

(i) determining a baseline concentration of analyte in said bloodstream corresponding with metabolic homeostasis of said body; and (j) determining whether said concentration of said analyte determined at step (i) exceeds the threshold value selected at step (h).

41. The method of claim 38 in which said analyte-containing fluid is selected from the group consisting of: ammoniacal fluid, heparin, ethanol, carbon dioxide releasing fluid, glucose, anesthesia agent, and excluding oxygen.

42. The method of claim 38 in which:

said step (a) includes the provision of a pH sensor mounted with said catheter and having a pH sensor output corresponding with the pH value of blood with which it is in contact;

said analyte-containing fluid is an ammoniacal fluid;

said step (d) includes the step:

(d1) obtaining said pH sensor output and deriving the pH value of the blood of said body; and said step (g) is carried out by correlating the said pH value, said baseline value, said subsequent value, said predetermined indicator concentration and said predetermined mass flow rate.

43. The method of claim 38 in which:

said analyte-containing fluid is an ammoniacal fluid;

said analyte concentration sensor is responsive to ammonia gas;

said step (d) includes the steps:
 (d1) obtaining the value of pH of the blood of said body;
 (d2) deriving said baseline value in correspondence with the concentration of ammonia gas ($NH_3$) in said bloodstream;
 (d3) deriving from said baseline value the total ammoniacal concentration in blood, in correspondence with the expressions:

$Ca(NH_4^+)=Ca(NH_3)/[10 \exp (pH-pKa)]$ $Ca=Ca(NH_3)+Ca(NH_4^+)$ where $Ca(NH_4^+)$ is the concentration of ammonium ions in blood, $Ca(NH_3)$ is the measured concentration of ammonia gas in blood, pH is measured blood pH, pKa is the pH level of solution above which ammonia exists as a gas, and Ca is the total ammoniacal concentration in blood.

44. The method of claim 43 in which:
 said step (g) derives said value for cardiac output in correspondence with the expression:

$$CO(t_i) = \frac{K * m_I * [IC_a - C_a(t'_i)]}{[C_a(t'_i) - C_a(t_i)]}$$

where, $CO(t_i)$ is cardiac output measured at time ($t_i$), K is a constant, $m_I$ is the fluid mass flow rate of ammoniacal fluid, ICa is total ammoniacal concentration of the analyte-containing fluid, $Ca(t'_I)$ is the total ammoniacal concentration in blood based upon said subsequent value measured during said infusion interval, and $Ca(t_i)$ is the total ammoniacal concentration in blood based upon said baseline value.

45. The method for determining the cardiac output of the cardiovascular system of the body of a patient, comprising the steps of:
 (a) providing a catheter having a proximal end region and extending to a measurement region, an indicator channel within said catheter having a fluid input at said proximal end region and extending to an infusion outlet at said measurement region from which analyte-containing fluid may be expressed, an analyte concentration sensor mounted with said catheter having a forward assembly contactable with flowing blood at said measurement region at a location spaced from said infusion outlet a dilution measurement distance, responsive to the presence of an analyte to provide an output corresponding with the concentration of analyte in blood;
 (b) positioning said catheter within the bloodstream of said body, locating said measurement region at the heart region of the patient in a cardiac output measurement orientation wherein said analyte concentration sensor is downstream within said bloodstream from said infusion outlet;
 (c) providing an analyte-containing fluid selected from the group consisting of: ammoniacal fluid, heparin, ethanol, carbon dioxide releasing fluid, glucose, anesthesia agent, and excluding oxygen;
 (d) deriving a baseline analyte concentration value in said bloodstream from said concentration sensor concentration output;
 (e) delivering said analyte-containing fluid from said source into said indicator channel input at a predetermined mass flow rate for an infusion interval;
 (f) deriving a subsequent analyte concentration value during said infusion interval from said concentration sensor output; and
 (g) deriving a value for the cardiac output of the heart of the body by correlating said baseline analyte concentration value, said subsequent analyte concentration value and said predetermined mass flow rate.

46. The method of claim 45 in which said analyte-containing fluid and said analyte concentration sensor are selected to carry out steps (d) through (f) with said infusion interval achieving a cardiac output measurement frequency of about one measurement each one to three minutes.

47. The method of claim 45 including the steps of:
 (h) selecting a homeostasis threshold value corresponding with an analyte concentration level in blood for iatrogenesis;
 (i) determining a baseline of analyte in said bloodstream concentration corresponding with metabolic homeostasis of said body; and
 (j) determining whether said concentration of analyte determined at step (i) exceeds the threshold value selected at step (h).

48. The method of claim 45 in which:
 said analyte-containing fluid is an ammoniacal fluid;
 said step (d) includes the steps:
 (d1) obtaining the value of pH of the blood of said body;
 (d2) deriving said baseline concentration value in correspondence with the concentration of ammonia gas ($NH_3$) in said bloodstream;
 (d3) deriving said baseline analyte concentration value as representing the total ammoniacal concentration in blood in correspondence with the expressions:

$Ca(NH_4^+)=Ca(NH_3)/[10 \exp (pH-pKa)]$ $Ca=Ca(NH_3)+Ca(NH_4^+)$ where $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists as a gas, and Ca is the total ammoniacal concentration in blood; and said step (f) includes the steps of:
 (f1) deriving said subsequent analyte concentration value in correspondence with the concentration of ammonia gas ($NH_3$) in said bloodstream,
 (f2) deriving said subsequent analyte concentration value as representing the total ammoniacal concentration in blood in correspondence with the expressions:

$Ca(NH_4^+)=Ca(NH_3)/[10 \exp (pH-pKa)]$ $Ca=Ca(NH_3)+Ca(NH_4^+)$ where $Ca(NH_4^+)$ is the concentration of ammonium ions in blood, $Ca(NH_3)$ is the measured concentration of ammonia gas in blood, pH is measured blood pH, pKa is the pH level of solution above which ammonia exists as a gas, and Ca is the total ammoniacal concentration in blood.

49. The method of claim 48 in which:
 said step (g) derives said value for cardiac output in correspondence with the expression:

$$CO(t_i) = \frac{K * m_I * [IC_a - C_a(t'_i)]}{[C_a(t'_i) - C_a(t_i)]}$$

where, $CO(t_i)$ is cardiac output measured at time $(t_i)$, K is a constant, $m_I$ is the mass flow rate of ammoniacal fluid, ICa is total ammoniacal concentration of the analyte-containing fluid, $Ca(t'_i)$ is the total ammoniacal concentration in blood based upon said subsequent value for analyte concentration of ammonia measured during said infusion interval, and $Ca(t_i)$ is the total ammoniacal concentration in blood based upon said baseline analyte concentration.

50. A system for determining the cardiac output of the cardiovascular system of the body of a patient, comprising:
   a source of analyte-containing fluid biocompatible with and metabolizable within said body and selected from the group consisting of: ammoniacal fluid, heparin, ethanol, carbon dioxide releasing fluid, glucose, anesthesia agent, and excluding oxygen;
   fluid flow control apparatus coupled with said source of analyte-containing fluid and controllable to provide a flow of said fluid at a mass flow rate for an infusion interval at a fluid output;
   a catheter having an externally disposed proximal end region and an oppositely disposed measurement region positionable within the bloodstream of said body;
   an indicator channel within said catheter having a fluid input at said proximal end region connected in fluid transfer relationship with said fluid flow control apparatus fluid output and extending to an infusion outlet at said measurement region from which said analyte-containing fluid may be expressed into the bloodstream of said body;
   an analyte concentration sensor responsive to said analyte within said bloodstream to provide a concentration sensor output, having a forward assembly contactable with flowing blood mounted with said catheter at said measurement region at a location spaced from said infusion outlet a dilution measurement distance downstream within said bloodstream;
   a controller for controlling said fluid flow control apparatus and said analyte concentration sensor, responsive to derive a baseline analyte concentration level in blood, then responsive to effect a flow of said analyte-containing fluid into said catheter fluid input at a predetermined mass flow rate for said infusion interval, responsive to derive a subsequent value for analyte concentration level in blood during said infusion interval, and responsive to correlate said baseline analyte concentration level in blood, said subsequent analyte concentration level in blood and said predetermined mass flow rate to derive a first output signal representing a value corresponding with cardiac output; and
   a display responsive to said first output signal for providing a perceptible output corresponding therewith.

51. The system of claim 50 in which said controller controls said fluid flow control apparatus to provide said infusion interval of about two to thirty seconds.

52. The system of claim 50 including:
   a pH sensor mounted with said catheter at a location for positioning within the bloodstream of said body and controllable to provide a pH sensor output corresponding with the pH value of blood with which it is in contact;
   said controller effects control of said pH sensor to derive said pH sensor output and is responsive to correlate said pH sensor output, said baseline analyte concentration level in blood, said subsequent value for analyte concentration level in blood, and said predetermined mass flow rate to derive said first output signal.

53. The system of claim 52 in which:
   said analyte containing fluid is an ammoniacal fluid;
   said analyte concentration sensor output is provided in correspondence with the concentration of ammonia gas $(NH_3)$ in said bloodstream; and
   said controller derives a total ammoniacal concentration in blood in correspondence with the expressions:

$Ca(NH_4^+) = Ca(NH_3)/[10 \exp (pH-pKa)]$ $Ca = Ca(NH_3) + Ca(NH_4^+)$ where: $Ca(NH_4^+)$ is the concentration of ammonium ions in blood, $Ca(NH_3)$ is the measured concentration of ammonia gas in blood, pH is measured blood pH, pKa is the pH level of solution above which ammoniacal fluid exists as a gas, and Ca is the total ammoniacal concentration in blood.

54. The system of claim 53 in which said controller derives said first output signal in correspondence with the expression:

$$CO(t_i) = \frac{K * m_I * [IC_a - C_a(t'_i)]}{[C_a(t'_i) - C_a(t_i)]}$$

where, $CO(t_i)$ is cardiac output measured at time $(t_i)$, K is a constant, $m_I$ is the said mass flow rate of ammoniacal fluid for said infusion interval, ICa is the total ammoniacal concentration of the analyte-containing fluid, $Ca(t'_i)$ is the total ammoniacal concentration in blood based upon said subsequent level for analyte concentration measured during said infusion interval, and $Ca(t_i)$ is the total ammoniacal concentration in blood based upon said baseline analyte concentration.

55. The system of claim 53 in which said analyte concentration sensor is configured to derive said concentration sensor output by optical colorimetry.

56. The system of claim 53 in which said analyte concentration sensor is configured to derive said concentration sensor output as an amperometry signal.

57. The system of claim 53 in which said analyte concentration sensor is configured to derive said concentration sensor output as a potentiometry signal.

58. The system of claim 53 in which said analyte concentration sensor is configured to derive said concentration sensor output employing optical fluorescence.

59. The system of claim 50 in which said controller is responsive to inputted values representing the height and weight of said body to derive a value for body surface area, and is responsive to a derived value of cardiac output and said value for body surface area to derive a second output signal representing a value of cardiac index; and
   said display is responsive to said second output signal for displaying said derived value representing cardiac index.

60. The system of claim 59 in which said controller is responsive to an inputted lower threshold limit for cardiac index retained in memory and to said derived value of cardiac index to derive a third output signal when said derived value of cardiac index is below said threshold limit value for cardiac index; and
   said display is responsive to said third output signal for displaying alarm information with respect to said derived value of cardiac index.

61. The system of claim 59 in which said controller is responsive to an inputted upper limit value for cardiac index retained in memory and to said derived value of cardiac index to derive a fourth output signal when said derived value of cardiac index is above said upper limit value for cardiac index; and said display is responsive to said fourth output signal for displaying alarm information with respect to said derived value of cardiac index.

62. The system of claim 50 in which:

said controller is responsive to derive a fifth output signal corresponding with instantaneous blood analyte concentration level; and said display is responsive to said fifth output signal for displaying said blood analyte concentration level.

\* \* \* \* \*